(12) United States Patent
Sokolsky et al.

(10) Patent No.: US 12,331,063 B2
(45) Date of Patent: Jun. 17, 2025

(54) HETERO-BICYCLIC INHIBITORS OF KRAS

(71) Applicant: Incyte Corporation, Wilmington, DE (US)

(72) Inventors: Alexander Sokolsky, Wilmington, DE (US); Chang Min, Newark, DE (US); Xiaozhao Wang, Mt. Laurel, NJ (US); Wenqing Yao, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/661,182

(22) Filed: Apr. 28, 2022

(65) Prior Publication Data

US 2022/0389033 A1   Dec. 8, 2022

Related U.S. Application Data

(60) Provisional application No. 63/240,467, filed on Sep. 3, 2021, provisional application No. 63/181,692, filed on Apr. 29, 2021.

(51) Int. Cl.
*C07D 519/00* (2006.01)
*A61P 35/00* (2006.01)

(52) U.S. Cl.
CPC .......... *C07D 519/00* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 9,315,505 B2 | 4/2016 | Ren et al. | |
| 9,751,884 B2 | 9/2017 | Xie et al. | |
| 9,868,707 B2 | 1/2018 | Pinkerton et al. | |
| 10,011,600 B2 | 7/2018 | Li et al. | |
| 10,130,625 B2 | 11/2018 | Sintim et al. | |
| 10,736,897 B2 | 8/2020 | Li et al. | |
| 10,822,312 B2 | 11/2020 | Li et al. | |
| 2021/0230162 A1 | 7/2021 | Zhao et al. | |
| 2021/0269434 A1 | 9/2021 | Wang et al. | |
| 2021/0355121 A1 | 11/2021 | Zhu et al. | |
| 2021/0355141 A1 | 11/2021 | Hoang et al. | |
| 2022/0064188 A1 | 3/2022 | Carlsen et al. | |
| 2022/0106309 A1 | 4/2022 | Huang et al. | |

FOREIGN PATENT DOCUMENTS

| | | |
|---|---|---|
| WO | WO 2005/030130 A2 | 4/2005 |
| WO | WO 2006/127329 A1 | 11/2006 |
| WO | WO 2009/064959 A1 | 5/2009 |
| WO | WO 2009/103966 A1 | 8/2009 |
| WO | WO 2011/082337 A1 | 7/2011 |
| WO | WO 2011/156626 A1 | 12/2011 |
| WO | WO 2015/054572 A1 | 4/2015 |
| WO | WO 2016/123627 A1 | 8/2016 |
| WO | WO 2018/119183 A2 | 6/2018 |
| WO | WO 2018/140512 A1 | 8/2018 |
| WO | WO 2020/156445 A1 | 8/2020 |

OTHER PUBLICATIONS

Chemical Abstract Registry No. 1368066-45-8, indexed in the Registry File on STN CAS Online Apr. 15, 2012.*
Chen et al., "Small-Molecule Inhibitors Directly Targeting KRAS as Anticancer Therapeutics", *Journal of Medicinal Chemistry* 63(3):14404-14424 (2020).
Cox et al., "Drugging the undruggable Ras: mission impossible?", *Nature Reviews Drug Discory* 13(11):828-851 (2014).
Fernandez-Merdarde et al., "Ras in Cancer and Developmental Diseases", *Genes & Cancer* 2(3):344-358 (2011).

* cited by examiner

*Primary Examiner* — Po-Chih Chen
(74) *Attorney, Agent, or Firm* — Lathrop GPM LLP; Brian C. Trinque; Nicole Sassu

(57) ABSTRACT

Disclosed are compounds of Formula I, methods of using the compounds for inhibiting KRAS activity and pharmaceutical compositions comprising such compounds. The compounds are useful in treating, preventing or ameliorating diseases or disorders associated with KRAS activity such as cancer.

36 Claims, No Drawings

HETERO-BICYCLIC INHIBITORS OF KRAS

RELATED APPLICATIONS

This application claims priority to U.S. Provisional Application No. 63/181,692, filed Apr. 29, 2021, and U.S. Provisional Application No. 63/240,467, filed on Sep. 3, 2021, the entire contents of which are incorporated by reference in their entirety.

FIELD OF THE INVENTION

The disclosure provides compounds as well as their compositions and methods of use. The compounds modulate KRAS activity and are useful in the treatment of various diseases including cancer.

BACKGROUND OF THE INVENTION

Ras proteins are part of the family of small GTPases that are activated by growth factors and various extracellular stimuli. The Ras family regulates intracellular signaling pathways responsible for growth, migration, survival and differentiation of cells. Activation of RAS proteins at the cell membrane results in the binding of key effectors and initiation of a cascade of intracellular signaling pathways within the cell, including the RAF and PI3K kinase pathways. Somatic mutations in RAS may result in uncontrolled cell growth and malignant transformation while the activation of RAS proteins is tightly regulated in normal cells (Simanshu, D. et al. Cell 170.1 (2017):17-33).

The Ras family is comprised of three members: KRAS, NRAS and HRAS. RAS mutant cancers account for about 25% of human cancers. KRAS is the most frequently mutated isoform accounting for 85% of all RAS mutations whereas NRAS and HRAS are found mutated in 12% and 3% of all Ras mutant cancers respectively (Simanshu, D. et al. Cell 170.1 (2017):17-33). KRAS mutations are prevalent amongst the top three most deadly cancer types: pancreatic (97%), colorectal (44%), and lung (30%) (Cox, A. D. et al. Nat Rev Drug Discov (2014) 13:828-51). The majority of RAS mutations occur at amino acid residue 12, 13, and 61. The frequency of specific mutations varies between RAS gene isoforms and while G12 and Q61 mutations are predominant in KRAS and NRAS respectively, G12, G13 and Q61 mutations are most frequent in HRAS. Furthermore, the spectrum of mutations in a RAS isoform differs between cancer types. For example, KRAS G12D mutations predominate in pancreatic cancers (51%), followed by colorectal adenocarcinomas (45%) and lung cancers (17%) while KRAS G12 V mutations are associated with pancreatic cancers (30%), followed by colorectal adenocarcinomas (27%) and lung adenocarcinomas (23%) (Cox, A. D. et al. Nat Rev Drug Discov (2014) 13:828-51). In contrast, KRAS G12C mutations predominate in non-small cell lung cancer (NSCLC) comprising 11-16% of lung adenocarcinomas, and 2-5% of pancreatic and colorectal adenocarcinomas (Cox, A. D. et al. Nat. Rev. Drug Discov. (2014) 13:828-51). Genomic studies across hundreds of cancer cell lines have demonstrated that cancer cells harboring KRAS mutations are highly dependent on KRAS function for cell growth and survival (McDonald, R. et al. Cell 170 (2017): 577-592). The role of mutant KRAS as an oncogenic driver is further supported by extensive in vivo experimental evidence showing mutant KRAS is required for early tumour onset and maintenance in animal models (Cox, A. D. et al. Nat Rev Drug Discov (2014) 13:828-51).

Taken together, these findings suggest that KRAS mutations play a critical role in human cancers; development of inhibitors targeting mutant KRAS may therefore be useful in the clinical treatment of diseases that are characterized by a KRAS mutation.

SUMMARY

The present disclosure provides, inter alia, a compound of Formula I:

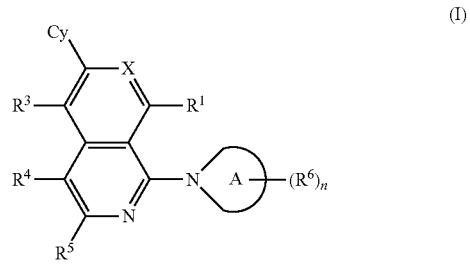

(I)

or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier or excipient.

The present disclosure further provides methods of inhibiting KRAS activity, which comprises administering to an individual a compound of the disclosure, or a pharmaceutically acceptable salt thereof. The present disclosure also provides uses of the compounds described herein in the manufacture of a medicament for use in therapy. The present disclosure also provides the compounds described herein for use in therapy.

The present disclosure further provides methods of treating a disease or disorder in a patient comprising administering to the patient a therapeutically effective amount of a compound of the disclosure, or a pharmaceutically acceptable salt thereof.

DETAILED DESCRIPTION

Compounds

In an aspect, provided herein is a compound of Formula I:

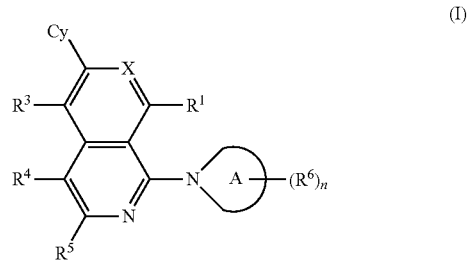

(I)

or a pharmaceutically acceptable salt thereof,
wherein:
$R^1$ is selected from H, D, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, OR$^{a1}$, SR$^{a1}$, C(O)R$^{b1}$, C(O)NR$^{c1}$R$^{d1}$, C(O) OR$^{a1}$, OC(O)R$^{b1}$, OC(O)NR$^{c1}$R$^{d1}$, NR$^{c1}$R$^{d1}$, NR$^{c1}$C (O)R$^{b1}$, NR$^{c1}$C(O)OR$^{a1}$, NR$^{c1}$C(O)NR$^{c1}$R$^{d1}$, NR$^{c1}$S (O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, S(O)$_2$NR$^{c1}$R$^{d1}$, and BR$^{h1}$R$^{i1}$; wherein said C$_{1-6}$ alkyl, C$_{2-6}$ alkenyl, C$_{2-6}$ alkynyl, C$_{3-6}$ cycloalkyl, phenyl, 5-6 membered heteroaryl, and 4-7 membered heterocycloalkyl, are each optionally substituted with 1, 2, 3, or 4 substituents independently selected from R$^g$;

X is N or CR$^2$;

R$^2$ is selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$alkylene, C$_{6-10}$ aryl-C$_{1-3}$alkylene, 5-10 membered heteroaryl-C$_{1-3}$alkylene, halo, D, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NOR$^{a2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$C(=NR$^{e2}$)R$^{b2}$, NR$^{c2}$S (O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, S(O)$_2$NR$^{c2}$R$^{d2}$, and BR$^{h2}$R$^{i2}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$alkylene, C$_{6-10}$ aryl-C$_{1-3}$alkylene and 5-10 membered heteroaryl-C$_{1-3}$ alkylene are each optionally substituted with 1, 2, 3, or 4 substituents independently selected from R$^{20}$;

Cy is selected from C$_{3-10}$ cycloalkyl, 4-10 membered heterocycloalkyl, C$_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the C$_{3-10}$ cycloalkyl, 4-10 membered heterocycloalkyl, C$_{6-10}$ aryl and 5-10 membered heteroaryl are each optionally substituted with 1, 2, 3 or 4 substituents independently selected from R$^{10}$;

R$^3$ is selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$alkylene, C$_{6-10}$ aryl-C$_{1-3}$alkylene, 5-10 membered heteroaryl-C$_{1-3}$alkylene, halo, D, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NOR$^{a3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$C(=NR$^{e3}$)R$^{b3}$, NR$^{c3}$S (O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, S(O)$_2$NR$^{c3}$R$^{d3}$, and BR$^{h3}$R$^{i3}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$alkylene and 5-10 membered heteroaryl-C$_{1-3}$alkylene are each optionally substituted with 1, 2, 3, or 4 substituents independently selected from R$^{30}$;

R$^4$ is selected from C$_{1-6}$alkyl, C$_{2-6}$alkenyl, C$_{2-6}$alkynyl, C$_{1-6}$haloalkyl, C$_{3-10}$cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$alkylene, C$_{6-10}$ aryl-C$_{1-3}$alkylene, 5-10 membered heteroaryl-C$_{1-3}$alkylene, halo, D, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NOR$^{a4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$C(=NR$^{e4}$)R$^{b4}$, NR$^{c4}$S(O) R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, S(O)$_2$NR$^{c4}$R$^{d4}$, and BR$^{h4}$R$^{i4}$; wherein said C$_{1-6}$alkyl, C$_{2-6}$alkenyl, C$_{2-6}$alkynyl, C$_{3-10}$cycloalkyl, 4-10 membered heterocycloalkyl, C$_{6-10}$ aryl, 5-10 membered heteroaryl, C$_{3-10}$cycloalkyl-C$_{1-3}$alkylene, 4-10 membered heterocycloalkyl-C$_{1-3}$alkylene, C$_{6-10}$ aryl-C$_{1-3}$alkylene and 5-10 membered heteroaryl-C$_{1-3}$alkylene are each optionally substituted with 1, 2, 3, or 4 substituents independently selected from R$^{40}$;

R$^5$ is selected from C$_{1-6}$alkyl, C$_{2-6}$alkenyl, C$_{2-6}$ alkynyl, C$_{1-6}$ haloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$alkylene, C$_{6-10}$ aryl-C$_{1-3}$alkylene, 5-10 membered heteroaryl-C$_{1-3}$alkylene, halo, D, NO$_2$, OR$^{a5}$, SR$^{a5}$, C(O) R$^{b5}$, C(O)NR$^{c5}$R$^{d5}$, C(O)OR$^{a5}$, OC(O)R$^{b5}$, OC(O) NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NOR$^{a5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$C (=NR$^{e5}$)R$^{b5}$, NR$^{c5}$S(O)R$^{b5}$, NR$^{c5}$S(O)$_2$R$^{b5}$, NR$^{c5}$S (O)$_2$NR$^{c5}$R$^{d5}$, S(O)R$^{b5}$, S(O)NR$^{c5}$R$^{d5}$, S(O)$_2$R$^{b5}$, S(O)$_2$NR$^{c5}$R$^{d5}$, and BR$^{h5}$R$^{i5}$; wherein said C$_{1-6}$alkyl, C$_{2-6}$alkenyl, C$_{2-6}$alkynyl, 4-10 membered heterocycloalkyl, C$_{6-10}$ aryl, 5-10 membered heteroaryl, C$_{3-10}$ cycloalkyl-C$_{1-3}$alkylene, 4-10 membered heterocycloalkyl-C$_{1-3}$ alkylene, C$_{6-10}$ alkylene and 5-10 membered heteroaryl-C$_{1-3}$ alkylene are each optionally substituted with 1, 2, 3, or 4 substituents independently selected from R$^{50}$;

ring A is selected from 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group;

R$^6$ is selected from C$_{1-6}$alkyl, C$_{2-6}$alkenyl, C$_{2-6}$alkynyl, C$_{1-6}$haloalkyl, C$_{3-10}$ cycloalkyl, 4-10 membered heterocycloalkyl, C$_{6-10}$ aryl, 5-10 membered heteroaryl, C$_{3-10}$cycloalkyl-C$_{1-3}$alkylene, 4-10 membered heterocycloalkyl-C$_{1-3}$alkylene, C$_{6-10}$ aryl-C$_{1-3}$alkylene, 5-10 membered heteroaryl-C$_{1-3}$alkylene, halo, D, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, C(=NR$^{e6}$)R$^{b6}$, C(=NOR$^{a6}$)R$^{b6}$, C(=NR$^{e6}$)NR$^{c6}$R$^{d6}$, NR$^{c6}$C (=NR$^{e6}$)NR$^{c6}$R$^{d6}$, NR$^{c6}$C(=NR$^{e6}$)R$^{b6}$, NR$^{c6}$S(O) R$^{b6}$, NR$^{c6}$S(O)$_2$R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, S(O)$_2$NR$^{c6}$R$^{d6}$, and BR$^{h6}$R$^{i6}$; wherein said C$_{1-6}$alkyl, C$_{2-6}$alkenyl, C$_{2-6}$alkynyl, C$_{3-10}$cycloalkyl, 4-10 membered heterocycloalkyl, C$_{6-10}$ aryl, 5-10 membered heteroaryl, C$_{3-10}$cycloalkyl-C$_{1-3}$alkylene, 4-10 membered heterocycloalkyl-C$_{1-3}$alkylene, C$_{6-10}$alkylene and 5-10 membered heteroaryl- $C_{1-3}$alkylene are each optionally substituted with 1, 2, 3, or 4 substituents independently selected from $R^{60}$;

n is 0, 1, 2, 3, or 4;

each $R^{10}$ is independently selected from $C_{1-6}$alkyl, $C_{2-6}$alkenyl, $C_{2-6}$alkynyl, $C_{1-6}$haloalkyl, $C_{3-10}$cycloalkyl, 4-10 membered heterocycloalkyl, $C_{6-10}$ aryl, 5-10 membered heteroaryl, $C_{3-10}$cycloalkyl-$C_{1-3}$alkylene, 4-10 membered heterocycloalkyl-$C_{1-3}$alkylene, $C_{6-10}$alkylene, 5-10 membered heteroaryl-$C_{1-3}$alkylene, halo, D, CN, $NO_2$, $OR^{a10}$, $SR^{a10}$, $C(O)R^{b10}$, $C(O)NR^{c10}R^{d10}$, $C(O)OR^{a10}$, $OC(O)R^{b10}$, $OC(O)NR^{c10}R^{d10}$, $NR^{c10}R^{d10}$, $NR^{c10}C(O)R^{b10}$, $NR^{c10}C(O)OR^{a10}$, $NR^{c10}C(O)NR^{c10}R^{d10}$, $C(=NR^{e10})R^{b10}$, $C(=NOR^{a10})R^{b10}$, $C(=NR^{e10})NR^{c10}R^{d10}$, $NR^{c10}C(=NR^{e10})NR^{c10}R^{d10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, $S(O)_2NR^{c10}R^{d10}$, and $BR^{h10}R^{i10}$; wherein said $C_{1-6}$ alkyl, $C_{2-6}$ alkenyl, $C_{2-6}$ alkynyl, $C_{3-10}$cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene, 5-10 membered heteroaryl-$C_{1-3}$ alkylene, halo, D, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)^2R^{b11}$, $S(O)_2NR^{c11}R^{d11}$, and $BR^{h11}R^{i11}$; wherein said $C_{1-6}$ alkyl, $C_{2-6}$alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, and $BR^{h12}R^{i12}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a20}$, $SR^{a20}$, $C(O)R^{b20}$, $C(O)NR^{c20}R^{d20}$, $C(O)OR^{a20}$, $OC(O)R^{b20}$, $OC(O)NR^{c20}R^{d20}$, $NR^{c20}R^{d20}$, $NR^{c20}C(O)R^{b20}$, $NR^{c20}C(O)OR^{a20}$, $NR^{c20}C(O)NR^{c20}R^{d20}$, $NR^{c20}S(O)R^{b20}$, $NR^{c20}S(O)_2R^{b20}$, $NR^{c20}S(O)_2NR^{c20}R^{d20}$ $S(O)R^{b20}$, $S(O)NR^{c20}R^{d20}$, $S(O)_2R^{b20}$, $S(O)_2NR^{c20}R^{d20}$, and $BR^{h20}R^{i20}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_2$-6 alkenyl, $C_2$-6 alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, and $BR^{h21}R^{i21}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a22}$, $SR^{a22}$, $C(O)R^{b22}$, $C(O)NR^{c22}R^{d22}$, $C(O)OR^{a22}$, $OC(O)R^{b22}$, $OC(O)NR^{c22}R^{d22}$, $NR^{c22}R^{d22}$, $NR^{c22}C(O)R^{b22}$, $NR^{c22}C(O)OR^{a22}$, $NR^{c22}C(O)NR^{c22}R^{d22}$, $NR^{c22}S(O)R^{b22}$, $NR^{c22}S(O)_2R^{b22}$, $NR^{c22}S(O)^2NR^{c22}R^{d22}$, $S(O)R^{b22}$, $S(O)NR^{c22}R^{d22}$, $S(O)_2R^{b22}$, $S(O)_2NR^{c22}R^{d22}$, and $BR^{h22}R^{i22}$, wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a30}$, $SR^{a30}$, $C(O)R^{b30}$, $C(O)NR^{c30}R^{d30}$, $C(O)OR^{a30}$, $OC(O)R^{b30}$, $OC(O)NR^{c30}R^{d30}$, $NR^{c30}R^{d30}$, $NR^{c30}C(O)R^{b30}$, $NR^{c30}C(O)OR^{a30}$, $NR^{c30}C(O)NR^{c30}R^{d30}$, $NR^{c30}S(O)R^{b30}$, $NR^{c30}S(O)_2R^{b30}$, $NR^{c30}(O)_2NR^{c30}R^{d30}$, $S(O)R^{b30}$, $S(O)NR^{c30}R^{d30}$, $S(O)_2R^{b30}$, $S(O)_2NR^{c30}R^{i30}$; and $BR^{h30}R^{i30}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{31}$;

each $R^{31}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene, 5-10 membered heteroaryl-$C_{1-3}$ alkylene, halo, D, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)OR^{a31}$, $NR^{c31}C(O)NR^{c31}R^{d31}$, $NR^{c31}S(O)R^{b31}$, $NR^{c31}S(O)_2R^{b31}$, $NR^cS(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, and $BR^{h31}R^{i31}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{32}$;

each $R^{32}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a32}$, $SR^{a32}$, $C(O)R^{b32}$, $C(O)NR^{c32}R^{d32}$, $C(O)OR^{a32}$, $OC(O)R^{b32}$, $OC(O)NR^{c32}R^{d32}$, $NR^{c32}R^{d32}$, $NR^{c32}C(O)R^{b32}$, $NR^{c32}C(O)OR^{a32}$, $NR^{c32}C(O)NR^{c32}R^{d32}$, $NR^{c32}S(O)R^{b32}$, $NR^{c32}S(O)_2R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, and $BR^{h32}R^{i32}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{40}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a40}$, $SR^{a40}$, $C(O)R^{b40}$, $C(O)NR^{c40}R^{d40}$, $C(O)OR^{a40}$, $OC(O)R^{b40}$, $OC(O)NR^{c40}R^{d40}$, $NR^{c40}R^{d40}$, $NR^{c40}C(O)R^{b40}$, $NR^{c40}C(O)OR^{a40}$, $NR^{c40}C(O)NR^{c40}R^{d40}$, $NR^{c40}S(O)R^{b40}$, $NR^{c40}S(O)_2R^{b40}$, $NR^{c40}S(O)_2NR^{c40}R^{d40}$, $S(O)R^{b40}$, $S(O)NR^{c40}R^{d40}$, $S(O)_2R^{b40}$, $S(O)_2NR^{c40}R^{d40}$, and $BR^{h40}R^{i40}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene and 5-10 membered heteroaryl-$C_{1-3}$ alkylene are each optionally substituted with 1, 2, 3, or 4 substituents independently selected from $R^{41}$;

each $R^{41}$ is independently selected from $C_{1-6}$ alkyl, $C_2$-6 alkenyl, $C_2$-6 alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $NR^{c41}S(O)R^{b41}$, $NR^{c41}S(O)_2R^{b41}$, $NR^{c41}S(O)_2NR^{c41}R^{d41}$, $S(O)R^{b41}$, $S(O)NR^{c41}R^{d41}$, $S(O)_2R^{b41}$, $S(O)_2NR^{c41}R^{d41}$, and $BR^{h41}R^{i41}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{42}$;

each $R^{42}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a42}$, $SR^{a42}$, $C(O)R^{b42}$, $C(O)NR^{c42}R^{d42}$, $C(O)OR^{a42}$, $OC(O)R^{b42}$, $OC(O)NR^{c42}R^{d42}$, $NR^{c42}R^{d42}$, $NR^{c42}C(O)R^{b42}$, $NR^{c42}C(O)OR^{a42}$, $NR^{c42}C(O)NR^{c42}R^{d42}$, $NR^{c42}S(O)R^{b42}$, $NR^{c42}S(O)_2R^{b42}$, $NR^{c42}S(O)_2NR^{c42}R^{d42}$, $S(O)R^{b42}$, $S(O)NR^{c42}R^{d42}$, $S(O)_2R^{b42}$, $S(O)_2NR^{c42}R^{d42}$, and $BR^{h42}R^{i42}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a50}$, $SR^{a50}$, $C(O)R^{b50}$, $C(O)NR^{c50}R^{d50}$, $C(O)OR^{a50}$, $OC(O)R^{b50}$, $OC(O)NR^{c50}R^{d50}$, $NR^{c50}R^{d50}$, $NR^{c50}C(O)R^{b50}$, $NR^{c50}C(O)OR^{a50}$, $NR^{c50}C(O)NR^{c50}R^{d50}$, $NR^{c50}S(O)R^{b50}$, $NR^{c50}S(O)_2R^{b50}S(O)_2NR^{c50}R^{d50}$, $S(O)R^{b50}$, $S(O)NR^{c50}R^{d50}$, $S(O)_2R^{b50}$, $S(O)_2NR^{c50}R^{d50}$, and $BR^{h50}R^{i50}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{51}$;

each $R^{51}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a51}$, $SR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, and $BR^{h51}R^{i51}$; wherein said $C_{1-6}$ alkyl, $C_{2-6}$ alkenyl, $C_{2-6}$ alkynyl, $C_{3-6}$ cycloalkyl, $C_{6-10}$ aryl, 5-6 membered heteroaryl and 4-7 membered heterocycloalkyl, are each optionally substituted with 1, 2, 3, or 4 substituents independently selected from $R^{52}$;

each $R^{52}$ is independently selected from $C_{1-6}$ alkyl, $C_{2-6}$ alkenyl, $C_2$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a52}$, $SR^{a52}$, $C(O)R^{b52}$, $C(O)NR^{c52}R^{d52}$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)R^{b52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, and $BR^{h62}R^{i52}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{60}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a60}$, $SR^{a60}$, $C(O)R^{b60}$, $C(O)NR^{c60}R^{d60}$, $C(O)OR^{a60}$, $OC(O)R^{b60}$, $OC(O)NR^{c60}R^{d60}$, $NR^{c60}R^{d60}$, $NR^{c60}C(O)R^{b60}$, $NR^{c60}C(O)OR^{a60}$, $NR^{c60}C(O)NR^{c60}R^{d60}$, $NR^{c60}S(O)R^{b60}$, $NR^{c60}S(O)_2R^{b60}$, $NR^{c60}S(O)_2NR^{c60}R^{d60}$, $S(O)R^{b60}$, $S(O)NR^{c60}R^{d60}$, $S(O)_2R^{b60}$, $S(O)_2NR^{c60}R^{d60}$, and $BR^{h60}R^{i60}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene and 5-10 membered heteroaryl-$C_{1-3}$ alkylene are each optionally substituted with 1, 2, 3, or 4 substituents independently selected from $R^g$;

each $R^{a1}$, $R^{b1}$, $R^{c1}$, and $R^{d1}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

or any $R^{c1}$ and $R^{d1}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{h1}$ and $R^{i1}$ is independently selected from OH, $C_{1-6}$ alkoxy, and $C_{1-6}$ haloalkoxy; or any $R^{h1}$ and $R^{i1}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a2}$, $R^{b2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{20}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3, or 4 substituents independently selected from $R^{20}$;

each $R^{e2}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h2}$ and $R^{i2}$ is independently selected from OH, $C_{1-6}$ alkoxy, and $C_{1-6}$ haloalkoxy; or any $R^{h2}$ and $R^{i2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

or any $R^{c3}$ and $R^{d3}$ attached to the same N atom, together with the N atom to which they are attached, form a 4-, 5-, 6- or 7-membered heterocycloalkyl group optionally substituted with 1, 2, 3, or 4 substituents independently selected from $R^{30}$;

each $R^{e3}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h3}$ and $R^{i3}$ is independently selected from OH, $C_{1-6}$ alkoxy, and $C_{1-6}$ haloalkoxy; or any $R^{h3}$ and $R^{i3}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a4}$, $R^{b4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{e4}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h4}$ and $R^{i4}$ is independently selected from OH, $C_{1-6}$ alkoxy, and $C_{1-6}$ haloalkoxy; or any $R^{h4}$ and $R^{i4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{50}$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^{50}$;

each $R^{e5}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h5}$ and $R^{i5}$ is independently selected from OH, $C_{1-6}$ alkoxy, and $C_{1-6}$ haloalkoxy; or any $R^{h5}$ and $R^{i5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a6}$, $R^{b6}$, $R^{c6}$, and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{60}$;

each $R^{e6}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h6}$ and $R^{i6}$ is independently selected from OH, $C_{1-6}$ alkoxy, and $C_{1-6}$ haloalkoxy; or any $R^{h6}$ and $R^{i6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c10}$ and $R^{d10}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{e10}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h10}$ and $R^{i10}$ is independently selected from OH, $C_{1-6}$ alkoxy, and $C_{1-6}$ haloalkoxy; or any $R^{h10}$ and $R^{i10}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a11}$, $R^{b11}$, $R^{c11}$ and $R^{d11}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c11}$ and $R^{d11}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{h11}$ and $R^{i11}$ is independently selected from OH, $C_{1-6}$ alkoxy, and $C_{1-6}$ haloalkoxy; or any $R^{h11}$ and $R^{i11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a12}$, $R^{b12}$, $R^{c12}$ and $R^{d12}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h12}$ and $R^{i12}$ is independently selected from OH, $C_{1-6}$ alkoxy, and $C_{1-6}$ haloalkoxy; or any $R^{h12}$ and $R^{i12}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{21}$;

or any $R^{c20}$ and $R^{d20}$ attached to the same N atom, together with the N atom to which they are attached, form a 4-, 5-, 6- or 7-membered heterocycloalkyl group optionally substituted with 1, 2, 3, or 4 substituents independently selected from $R^{21}$;

each $R^{h20}$ and $R^{i20}$ is independently selected from OH, $C_{1-6}$ alkoxy, and $C_{1-6}$ haloalkoxy; or any $R^{h20}$ and $R^{i20}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a21}$, $R^{b21}$, $R^{c21}$ and $R^{d21}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

or any $R^{c21}$ and $R^{d21}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{h21}$ and $R^{i21}$ is independently selected from OH, $C_{1-6}$ alkoxy, and $C_{1-6}$ haloalkoxy; or any $R^{h21}$ and $R^{i21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a22}$, $R^{b22}$, $R^{c22}$ and $R^{d22}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h22}$ and $R^{i22}$ is independently selected from OH, $C_{1-6}$ alkoxy, and $C_{1-6}$ haloalkoxy; or any $R^{h22}$ and $R^{i22}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a30}$, $R^{b30}$, $R^{c30}$ and $R^{d30}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{31}$;

or any $R^{c30}$ and $R^{d30}$ attached to the same N atom, together with the N atom to which they are attached, form a 4-, 5-, 6- or 7-membered heterocycloalkyl group optionally substituted with 1, 2, 3, or 4 substituents independently selected from $R^{31}$;

each $R^{h30}$ and $R^{i30}$ is independently selected from OH, $C_{1-6}$ alkoxy, and $C_{1-6}$ haloalkoxy; or any $R^{h30}$ and $R^{i30}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a31}$, $R^{b31}$, $R^{c31}$ and $R^{d31}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{32}$;

or any $R^{c31}$ and $R^{d31}$ attached to the same N atom, together with the N atom to which they are attached, form a 4-, 5-, 6- or 7-membered heterocycloalkyl group optionally substituted with 1, 2 or 3 substituents independently selected from $R^{32}$;

each $R^{h31}$ and $R^{i31}$ is independently selected from OH, $C_{1-6}$ alkoxy, and $C_{1-6}$ haloalkoxy; or any $R^{h31}$ and $R^{i31}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a32}$, $R^{b32}$, $R^{c32}$ and $R^{d32}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c32}$ and $R^{d32}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h32}$ and $R^{i32}$ is independently selected from OH, $C_{1-6}$ alkoxy, and $C_{1-6}$ haloalkoxy; or any $R^{h32}$ and $R^{i32}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a40}$, $R^{b40}$, $R^{c40}$ and $R^{d40}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{41}$;

or any $R^{c40}$ and $R^{d40}$ attached to the same N atom, together with the N atom to which they are attached, form a 4-, 5-, 6- or 7-membered heterocycloalkyl group optionally substituted with 1, 2, 3, or 4 substituents independently selected from $R^{41}$;

each $R^{h40}$ and $R^{i40}$ is independently selected from OH, $C_{1-6}$ alkoxy, and $C_{1-6}$ haloalkoxy; or any $R^{h40}$ and $R^{i40}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a41}$, $R^{b41}$, $R^{c41}$ and $R^{d41}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{42}$;

or any $R^{c41}$ and $R^{d41}$ attached to the same N atom, together with the N atom to which they are attached, form a 4-, 5-, 6- or 7-membered heterocycloalkyl group optionally substituted with 1, 2 or 3 substituents independently selected from $R^{42}$;

each $R^{h41}$ and $R^{i41}$ is independently selected from OH, $C_{1-6}$ alkoxy, and $C_{1-6}$ haloalkoxy; or any $R^{h41}$ and $R^{i41}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a42}$, $R^{b42}$, $R^{c42}$ and $R^{d42}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c42}$ and $R^{d42}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h42}$ and $R^{i42}$ is independently selected from OH, $C_{1-6}$ alkoxy, and $C_{1-6}$ haloalkoxy; or any $R^{h42}$ and $R^{i42}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a50}$, $R^{b50}$, $R^{c50}$ and $R^{d50}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{51}$;

or any $R^{c50}$ and $R^{d50}$ attached to the same N atom, together with the N atom to which they are attached, form a 4-, 5-, 6- or 7-membered heterocycloalkyl group optionally substituted with 1, 2 or 3 substituents independently selected from $R^{51}$;

each $R^{h50}$ and $R^{i50}$ is independently selected from OH, $C_{1-6}$ alkoxy, and $C_{1-6}$ haloalkoxy; or any $R^{h50}$ and $R^{i50}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a51}$, $R^{b51}$, $R^{c51}$ and $R^{d51}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{52}$;

or any $R^{c51}$ and $R^{d51}$ attached to the same N atom, together with the N atom to which they are attached, form a 4-, 5-, 6- or 7-membered heterocycloalkyl group optionally substituted with 1, 2, 3, or 4 substituents independently selected from $R^{52}$;

each $R^{h51}$ and $R^{i51}$ is independently selected from OH, $C_{1-6}$ alkoxy, and $C_{1-6}$ haloalkoxy; or any $R^{h51}$ and $R^{i51}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a52}$, $R^{b52}$, $R^{c52}$ and $R^{d52}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c52}$ and $R^{d52}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h52}$ and $R^{i52}$ is independently selected from OH, $C_{1-6}$ alkoxy, and $C_{1-6}$ haloalkoxy; or any $R^{h52}$ and $R^{i52}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a60}$, $R^{b60}$, $R^{c60}$ and $R^{d60}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^g$;

or any $R^{c60}$ and $R^{d60}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h60}$ and $R^{i60}$ is independently selected from OH, $C_{1-6}$ alkoxy, and $C_{1-6}$ haloalkoxy; or any $R^{h60}$ and $R^{i60}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^g$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$alkyl)aminocarbonyloxy, $C_{1-6}$ alkylsulfonylamino, aminosulfonyl, $C_{1-6}$ alkylaminosulfonyl, di($C_{1-6}$alkyl)aminosulfonyl, aminosulfonylamino, $C_{1-6}$ alkylaminosulfonylamino, di($C_{1-6}$alkyl)aminosulfonylamino, aminocarbonylamino, $C_{1-6}$ alkylaminocarbonylamino, and di($C_{1-6}$ alkyl)aminocarbonylamino.

In an embodiment of Formula I, or a pharmaceutically acceptable salt thereof, $R^1$ is selected from H, D, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, and $BR^{h1}R^{i1}$;

X is N or $CR^2$;

$R^2$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)$ $NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, and $BR^{h2}R^{i2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{20}$;

Cy is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^3$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NOR^{a3})R^{b3}$, $C(=NR^{e3})NR^{c3}R^{d3}$, $NR^{c3}C(=NR^{e3})NR^{c3}R^{d3}$, $NR^{c3}C(=NR^{e3})R^{b3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)^2R^{b3}$, $S(O)_2NR^{c3}R^{d3}$, and $BR^{h3}R^{i3}$; wherein said $C_{1-6}$ alkyl, $C_{2-6}$ alkenyl, $C_{2-6}$ alkynyl, $C_{3-10}$cycloalkyl, 4-10 membered heterocycloalkyl, $C_{6-10}$ aryl, 5-10 membered heteroaryl, $C_{3-10}$cycloalkyl-$C_{1-3}$alkylene, 4-10 membered heterocycloalkyl-$C_{1-3}$alkylene, $C_{6-10}$ aryl-$C_{1-3}$alkylene and 5-10 membered heteroaryl-$C_{1-3}$alkylene are each optionally substituted with 1, 2, 3, or 4 substituents independently selected from $R^{30}$;

$R^4$ is selected from $C_{1-6}$ alkyl, $C_{2-6}$ alkenyl, $C_{2-6}$ alkynyl, $C_{1-6}$ haloalkyl, $C_{3-10}$cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$alkylene, 5-10 membered heteroaryl-$C_{1-3}$ alkylene, halo, D, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NOR^{a4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $BR^{h4}R^{i4}$; wherein said $C_{1-6}$ alkyl, $C_{2-6}$ alkenyl, $C_{2-6}$ alkynyl, $C_{3-10}$cycloalkyl, 4-10 membered heterocycloalkyl, $C_{6-10}$ aryl, 5-10 membered heteroaryl, $C_{3-10}$cycloalkyl-$C_{1-3}$alkylene, 4-10 membered heterocycloalkyl-$C_{1-3}$alkylene, $C_{6-10}$ aryl-$C_{1-3}$alkylene and 5-10 membered heteroaryl-$C_{1-3}$ alkylene are each optionally substituted with 1, 2, 3, or 4 substituents independently selected from $R^{40}$;

$R^5$ is selected from $C_{1-6}$ alkyl, $C_{2-6}$ alkenyl, $C_{2-6}$ alkynyl, $C_{1-6}$ haloalkyl, 4-10 membered heterocycloalkyl, $C_{6-10}$ aryl, 5-10 membered heteroaryl, $C_{3-10}$cycloalkyl-$C_{1-3}$alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NOR^{a5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $BR^{h5}R^{i5}$; wherein said $C_{1-6}$ alkyl, $C_{2-6}$ alkenyl, $C_{2-6}$ alkynyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{50}$;

ring A is selected from 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group;

$R^6$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOR^{a6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $BR^{h6}R^{i6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene and 5-10 membered heteroaryl-$C_{1-3}$ alkylene are each optionally substituted with 1, 2, 3, or 4 substituents independently selected from $R^{60}$;

n is 0, 1, 2, 3, or 4;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a10}$, $SR^{a10}$, $C(O)R^{b10}$, $C(O)NR^{c10}R^{d10}$, $C(O)OR^{a10}$, $OC(O)R^{b10}$, $OC(O)NR^{c10}R^{d10}$, $NR^{c10}R^{d10}$, $NR^{c10}C(O)R^{b10}$, $NR^{c10}C(O)OR^{a10}$, $NR^{c10}C(O)NR^{c10}R^{d10}$, $C(=NR^{e10})R^{b10}$, $C(=NOR^{a10})R^{b10}$, $C(=NR^{e10})NR^{c10}R^{d10}$, $NR^{c10}C(=NR^{e10})NR^{c10}R^{d10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, $S(O)_2NR^{c10}R^{d10}$, and $BR^{h10}R^{i10}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, and $BR^{h11}R^{i11}$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a20}$, $SR^{a20}$, $C(O)R^{b20}$, $C(O)NR^{c20}R^{d20}$, $C(O)OR^{a20}$, $OC(O)R^{b20}$, $OC(O)NR^{c20}R^{d20}$, $NR^{c20}R^{d20}$, $NR^{c20}C(O)R^{b20}$, $NR^{c20}C(O)OR^{a20}$, $NR^{c20}C(O)NR^{c20}R^{d20}$, $NR^{c20}S(O)R^{b20}$, $NR^{c20}S(O)_2R^{b20}$, $NR^{c20}S(O)_2NR^{c20}R^{d20}$, $S(O)R^{b20}$, $S(O)NR^{c20}R^{d20}$, $S(O)_2R^{b20}$, $S(O)_2NR^{c20}R^{d20}$, and $BR^{h20}R^{i20}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$; $S(O)_2R^{b21}$; $S(O)_2NR^{c21}R^{d21}$, and $BR^{h21}R^{i21}$;

each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$alkylene, 5-10 membered heteroaryl-$C_{1-3}$ alkylene, halo, D, CN, $NO_2$, $OR^{a30}$, $SR^{a30}$, $C(O)R^{b30}$, $C(O)NR^{c30}R^{d30}$, $C(O)OR^{a30}$, $OC(O)R^{b30}$, $OC(O)NR^{c30}R^{d30}$, $NR^{c30}R^{d30}$, $NR^{c30}C(O)R^{b30}$, $NR^{c30}C(O)OR^{a30}$, $NR^{c30}C(O)NR^{c30}R^{d30}$, $NR^{c30}S(O)R^{b30}$, $NR^{c30}S(O)_2R^{b30}$, $NR^{c30}S(O)_2NR^{c30}R^{d30}$, $S(O)R^{b30}$, $S(O)NR^{c30}R^{d30}$, $S(O)_2R^{b30}$, $S(O)_2NR^{c30}R^{d30}$, and $BR^{h30}R^{i30}$;

each $R^{40}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$alkylene, 5-10 membered heteroaryl-$C_{1-3}$ alkylene, halo, D, CN, $NO_2$, $OR^{a40}$, $SR^{a40}$, $C(O)R^{b40}$, $C(O)NR^{c40}R^{d40}$, $C(O)OR^{a40}$, $OC(O)R^{b40}$, $OC(O)NR^{c40}R^{d40}$, $NR^{c40}R^{d40}$, $NR^{c40}C(O)R^{b40}$, $NR^{c40}C(O)OR^{a40}$, $NR^{c40}C(O)NR^{c40}R^{d40}$, $NR^{c40}S(O)R^{b40}$, $NR^{c40}S(O)_2R^{b40}$, $NR^{c40}S(O)_2NR^{c40}R^{d40}$, $S(O)R^{b40}$, $S(O)NR^{c40}R^{d40}$, $S(O)_2R^{b40}$, $S(O)_2NR^{c40}R^{d40}$, and $BR^{h40}R^{i40}$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a50}$, $SR^{a50}$, $C(O)R^{b50}$, $C(O)NR^{c50}R^{d50}$, $C(O)OR^{a50}$, $OC(O)R^{b50}$, $OC(O)NR^{c50}R^{d50}$, $NR^{c50}R^{d50}$, $NR^{c50}C(O)R^{b50}$, $NR^{c50}C(O)OR^{a50}$, $NR^{c50}C(O)NR^{c50}R^{d50}$, $NR^{c50}S(O)R^{b50}$, $NR^{c50}S(O)_2R^{b50}$, $NR^{c50}S(O)_2NR^{c50}R^{d50}$, $S(O)R^{b50}$, $S(O)NR^{c50}R^{d50}$, $S(O)_2R^{b50}$, $S(O)_2NR^{c50}R^{d50}$, and $BR^{h50}R^{i50}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{51}$;

each $R^{51}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a51}$, $SR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, and $BR^{h51}R^{i51}$; wherein said $C_{1-6}$ alkyl, $C_{2-6}$ alkenyl, $C_{2-6}$ alkynyl, $C_{3-6}$ cycloalkyl, $C_{6-10}$ aryl, 5-6 membered heteroaryl and 4-7 membered heterocycloalkyl, are each optionally substituted with 1, 2, 3, or 4 substituents independently selected from $R^{52}$;

each $R^{52}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a52}$, $SR^{a52}$, $C(O)R^{b52}$, $C(O)NR^{c52}R^{d52}$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)R^{b52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, and $BR^{h52}R^{i52}$;

each $R^{60}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a60}$, $SR^{a60}$, $C(O)R^{b60}$, $C(O)NR^{c60}R^{d60}$, $C(O)OR^{a60}$, $OC(O)R^{b60}$, $OC(O)NR^{c60}R^{d60}$, $NR^{c60}R^{d60}$, $NR^{c60}C(O)R^{b60}$, $NR^{c60}C(O)OR^{a60}$, $NR^{c60}C(O)NR^{c60}R^{d60}$, $NR^{c60}S(O)R^{b60}$, $NR^{c60}S(O)_2R^{b60}$, $NR^{c60}S(O)_2NR^{c60}R^{d60}$, $S(O)R^{b60}$, $S(O)NR^{c60}R^{d60}$, $S(O)_2R^{b60}$, $S(O)_2NR^{c60}R^{d60}$, and $BR^{h60}R^{i60}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^g$;

each $R^{a1}$, $R^{b1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

or any $R^{c1}$ and $R^{d1}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{h1}$ and $R^{i1}$ is independently selected from OH, $C_{1-6}$ alkoxy, and $C_{1-6}$ haloalkoxy; or any $R^{h1}$ and $R^{i1}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a2}$, $R^{b2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{20}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3, or 4 substituents independently selected from $R^{20}$;

each $R^{e2}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h2}$ and $R^{i2}$ is independently selected from OH, $C_{1-6}$ alkoxy, and $C_{1-6}$ haloalkoxy; or any $R^{h2}$ and $R^{i2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

or any $R^{c3}$ and $R^{d3}$ attached to the same N atom, together with the N atom to which they are attached, form a 4-, 5-, 6- or 7-membered heterocycloalkyl group optionally substituted with 1, 2, 3, or 4 substituents independently selected from $R^{30}$;

each $R^{e3}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h3}$ and $R^{i3}$ is independently selected from OH, $C_{1-6}$ alkoxy, and $C_{1-6}$ haloalkoxy; or any $R^{h3}$ and $R^{i3}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a4}$, $R^{b4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{e4}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h4}$ and $R^{i4}$ is independently selected from OH, $C_{1-6}$ alkoxy, and $C_{1-6}$ haloalkoxy; or any $R^{h4}$ and $R^{i4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{50}$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^{50}$;

each $R^{e5}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h5}$ and $R^{i5}$ is independently selected from OH, $C_{1-6}$ alkoxy, and $C_{1-6}$ haloalkoxy; or any $R^{h5}$ and $R^{i5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a6}$, $R^{c6}$, and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

each $R^{b6}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{60}$;

each $R^{e6}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h6}$ and $R^{i6}$ is independently selected from OH, $C_{1-6}$ alkoxy, and $C_{1-6}$ haloalkoxy; or any $R^{h6}$ and $R^{i6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c10}$ and $R^{d10}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{e10}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h10}$ and $R^{i10}$ is independently selected from OH, $C_{1-6}$ alkoxy, and $C_{1-6}$ haloalkoxy; or any $R^{h10}$ and $R^{i10}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a11}$, $R^{b11}$, $R^{c11}$ and $R^{d11}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c11}$ and $R^{d11}$ attached to the same N atom, together with the N atom to which they are attached, form a 4-, 5-, 6- or 7-membered heterocycloalkyl group;

each $R^{h11}$ and $R^{i11}$ is independently selected from OH, $C_{1-6}$ alkoxy, and $C_{1-6}$ haloalkoxy; or any $R^{h11}$ and $R^{i11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{21}$;

or any $R^{c20}$ and $R^{d20}$ attached to the same N atom, together with the N atom to which they are attached, form a 4-, 5-, 6- or 7-membered heterocycloalkyl group optionally substituted with 1, 2, 3, or 4 substituents independently selected from $R^{21}$;

each $R^{h20}$ and $R^{i20}$ is independently selected from OH, $C_{1-6}$ alkoxy, and $C_{1-6}$ haloalkoxy; or any $R^{h20}$ and $R^{i20}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a21}$, $R^{b21}$, $R^{c21}$ and $R^{d21}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c21}$ and $R^{d21}$ attached to the same N atom, together with the N atom to which they are attached, form a 4-, 5-, 6- or 7-membered heterocycloalkyl group;

each $R^{h21}$ and $R^{i21}$ is independently selected from OH, $C_{1-6}$ alkoxy, and $C_{1-6}$ haloalkoxy; or any $R^{h21}$ and $R^{i21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a30}$, $R^{b30}$, $R^{c30}$ and $R^{d30}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c30}$ and $R^{d30}$ attached to the same N atom, together with the N atom to which they are attached, form a 4-, 5-, 6- or 7-membered heterocycloalkyl group;

each $R^{h30}$ and $R^{i30}$ is independently selected from OH, $C_{1-6}$ alkoxy, and $C_{1-6}$ haloalkoxy; or any $R^{h30}$ and $R^{i30}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a40}$, $R^{b40}$, $R^{c40}$ and $R^{d40}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c40}$ and $R^{d40}$ attached to the same N atom, together with the N atom to which they are attached, form a 4-, 5-, 6- or 7-membered heterocycloalkyl group;

each $R^{h40}$ and $R^{i40}$ is independently selected from OH, $C_{1-6}$ alkoxy, and $C_{1-6}$ haloalkoxy; or any $R^{h40}$ and $R^{i40}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a50}$, $R^{b50}$, $R^{c50}$ and $R^{d50}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{51}$;

or any $R^{c50}$ and $R^{d50}$ attached to the same N atom, together with the N atom to which they are attached, form a 4-, 5-, 6- or 7-membered heterocycloalkyl group optionally substituted with 1, 2 or 3 substituents independently selected from $R^{51}$;

each $R^{h50}$ and $R^{i50}$ is independently selected from OH, $C_{1-6}$ alkoxy, and $C_{1-6}$ haloalkoxy; or any $R^{h50}$ and $R^{i50}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a51}$, $R^{b51}$, $R^{c51}$ and $R^{d51}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{52}$;

or any $R^{c51}$ and $R^{d51}$ attached to the same N atom, together with the N atom to which they are attached, form a 4-, 5-, 6- or 7-membered heterocycloalkyl group optionally substituted with 1, 2, 3, or 4 substituents independently selected from $R^{52}$;

each $R^{h51}$ and $R^{i51}$ is independently selected from OH, $C_{1-6}$ alkoxy, and $C_{1-6}$ haloalkoxy; or any $R^{h51}$ and $R^{i51}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a52}$, $R^{b52}$, $R^{c52}$ and $R^{d52}$, is independently selected from H, $C_{1-6}$ alkyl, $C_{2-6}$ alkenyl, $C_{2-6}$ alkynyl and $C_{1-6}$ haloalkyl;

or any $R^{c52}$ and $R^{d52}$ attached to the same N atom, together with the N atom to which they are attached, form a 4-, 5-, 6- or 7-membered heterocycloalkyl group;

each $R^{h52}$ and $R^{i52}$ is independently selected from OH, $C_{1-6}$ alkoxy, and $C_{1-6}$ haloalkoxy; or any $R^{h52}$ and $R^{i52}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a60}$, $R^{b60}$, $R^{c60}$ and $R^{d60}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^g$;

or any $R^{c60}$ and $R^{d60}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h60}$ and $R^{i60}$ is independently selected from OH, $C_{1-6}$ alkoxy, and $C_{1-6}$ haloalkoxy; or any $R^{h60}$ and $R^{i60}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^g$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In another embodiment of Formula I, or a pharmaceutically acceptable salt thereof, $R^1$ is selected from H, D, $C_{1-6}$ alkyl, $C_{1-6}$ haloalkyl, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$;

X is N or $CR^2$;

$R^2$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{20}$;

Cy is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^3$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$alkylene, 5-10 membered heteroaryl-$C_{1-3}$alkylene, halo, D, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$;

$R^4$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$alkylene, 5-10 membered heteroaryl-$C_{1-3}$alkylene, halo, D, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$;

$R^5$ is selected from $C_{1-6}$ alkyl, $C_{2-6}$ alkenyl, $C_{2-6}$ alkynyl, $C_{1-6}$ haloalkyl, 4-10 membered heterocycloalkyl, $C_{6-10}$ aryl, 5-10 membered heteroaryl, $C_{3-10}$cycloalkyl-$C_{1-3}$alkylene, 4-10 membered heterocycloalkyl-$C_{1-3}$ alkylene, $C_{6-10}$ aryl-$C_{1-3}$alkylene, 5-10 membered heteroaryl-$C_{1-3}$ alkylene, halo, D, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $NR^{c5}S(O)_2R^{b5}$, $NR^{c5}S(O)_2NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, 4-10 membered heterocycloalkyl, $C_{6-10}$ aryl, 5-10 membered heteroaryl, $C_{3-10}$cycloalkyl-$C_{1-3}$alkylene, 4-10 membered heterocycloalkyl-$C_{1-3}$ alkylene, $C_{6-10}$ aryl-$C_{1-3}$alkylene and 5-10 membered heteroaryl-$C_{1-3}$ alkylene are each optionally substituted with 1, 2, 3, or 4 substituents independently selected from $R^{50}$;

ring A is selected from 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group;

$R^6$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)_2R^{b6}$, $NR^{c6}S(O)_2NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{60}$;

n is 0, 1, 2, 3, or 4;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene, 5-10 membered heteroaryl-$C_{1-3}$ alkylene, halo, D, CN, $OR^{a10}$, $SR^{a10}$, $C(O)R^{b10}$, $C(O)NR^{c10}R^{d10}$, $C(O)OR^{a10}$, $OC(O)R^{b10}$, $OC(O)NR^{c10}R^{d10}$, $NR^{c10}R^{d10}$, $NR^{c10}C(O)R^{b10}$, $NR^{c10}C(O)OR^{a10}$, $NR^{c10}C(O)NR^{c10}R^{d10}$, $NR^{c10}S(O)_2R^{b10}$, $NR^{c10}S(O)_2NR^{c10}R^{d10}$, $S(O)_2R^{b10}$, and $S(O)_2NR^{c10}R^{d10}$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene, 5-10 membered heteroaryl-$C_{1-3}$ alkylene, halo, D, CN, $OR^{a20}$, $SR^{a20}$, $C(O)R^{b20}$, $C(O)NR^{c20}R^{d20}$, $C(O)OR^{a20}$, $OC(O)R^{b20}$, $OC(O)NR^{c20}R^{d20}$, $NR^{c20}R^{d20}$, $NR^{c20}C(O)R^{b20}$, $NR^{c20}C(O)OR^{a20}$, $NR^{c20}C(O)NR^{c20}R^{d20}$, $NR^{c20}S(O)_2R^{b20}$, $NR^{c20}S(O)_2NR^{c20}R^{d20}$, $S(O)_2R^{b20}$, and $S(O)_2NR^{c20}R^{d20}$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene, 5-10 membered heteroaryl-$C_{1-3}$ alkylene, halo, D, CN, $OR^{a50}$, $SR^{a50}$, $C(O)R^{b50}$, $C(O)NR^{c50}R^{d50}$, $C(O)OR^{a50}$, $OC(O)R^{b50}$, $OC(O)NR^{c50}R^{d50}$, $NR^{c50}R^{d50}$, $NR^{c50}C(O)R^{b50}$, $NR^{c50}C(O)OR^{a50}$, $NR^{c50}C(O)NR^{c50}R^{d50}$, $NR^{c50}S(O)_2R^{b50}$, $NR^{c50}S(O)_2NR^{c50}R^{d50}$, $S(O)_2R^{b50}$, and $S(O)_2NR^{c50}R^{d50}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{51}$;

each $R^{51}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene, 5-10 membered heteroaryl-$C_{1-3}$ alkylene, halo, D, CN, $OR^{a51}$, $SR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)_2R^{b51}$, $NR^{c51}S(O)_2NR^{c51}R^{d51}$, $S(O)_2R^{b51}$, and $S(O)_2NR^{c51}R^{d61}$;

each $R^{60}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a60}$, $SR^{a60}$, $C(O)R^{b60}$, $C(O)NR^{c60}R^{d60}$, $C(O)OR^{a60}$, $OC(O)R^{b60}$, $OC(O)NR^{c60}R^{d60}$, $NR^{c60}R^{d60}$, $NR^{c60}C(O)R^{b60}$, $NR^{c60}C(O)OR^{a60}$, $NR^{c60}C(O)NR^{c60}R^{d60}$, $NR^{c60}S(O)_2R^{b60}$, $NR^{c60}S(O)_2NR^{c60}R^{d60}$, $S(O)_2R^{b60}$, and $S(O)_2NR^{c60}R^{d60}$;

each $R^{a1}$, $R^{b1}$, $R^{c1}$, and $R^{d1}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl;

or any $R^{c1}$ and $R^{d1}$ attached to the same N atom, together with the N atom to which they are attached, form a 4-, 5-, 6- or 7-membered heterocycloalkyl group;

each $R^{a2}$, $R^{b2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{20}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3, or 4 substituents independently selected from $R^{20}$;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c3}$ and $R^{d3}$ attached to the same N atom, together with the N atom to which they are attached, form a 4-, 5-, 6- or 7-membered heterocycloalkyl group;

each $R^{a4}$, $R^{b4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c4}$ and $R^{d4}$ attached to the same N atom, together with the N atom to which they are attached, form a 4-, 5-, 6- or 7-membered heterocycloalkyl group;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{50}$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^{50}$;

each $R^{a6}$, $R^{c6}$, and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

each $R^{b6}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{60}$;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c10}$ and $R^{d10}$ attached to the same N atom, together with the N atom to which they are attached, form a 4-, 5-, 6- or 7-membered heterocycloalkyl group;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c20}$ and $R^{d20}$ attached to the same N atom, together with the N atom to which they are attached, form a 4-, 5-, 6- or 7-membered heterocycloalkyl group;

each $R^{a50}$, $R^{b50}$, $R^{c50}$ and $R^{d50}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{51}$;

or any $R^{c50}$ and $R^{d50}$ attached to the same N atom, together with the N atom to which they are attached, form a 4-, 5-, 6- or 7-membered heterocycloalkyl group optionally substituted with 1, 2 or 3 substituents independently selected from $R^{51}$;

each $R^{a51}$, $R^{b51}$, $R^{c51}$ and $R^{d51}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c51}$ and $R^{d51}$ attached to the same N atom, together with the N atom to which they are attached, form a 4-, 5-, 6- or 7-membered heterocycloalkyl group;

each $R^{a60}$, $R^{b60}$; $R^{c60}$ and $R^{d60}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; and or any $R^{c60}$ and $R^{d60}$ attached to the same N atom, together with the N atom to which they are attached, form a 4-, 5-, 6- or 7-membered heterocycloalkyl group.

In yet another embodiment of Formula I, or a pharmaceutically acceptable salt thereof, $R^1$ is selected from H, D, $C_{1-6}$ alkyl, $C_{1-6}$ haloalkyl, halo, and CN;

X is $CR^2$;

$R^2$ is selected from H, $C_{1-6}$ alkyl, $C_{1-6}$ haloalkyl, $C_{3-10}$ cycloalkyl-$C_{1-3}$alkylene, 4-10 membered heterocycloalkyl-$C_{1-3}$alkylene, halo, D, CN, $OR^{a2}$, C(O) $NR^{c2}R^{d2}$, and $NR^{c2}R^{d2}$; wherein said $C_{1-6}$ alkyl, $C_{3-10}$ cycloalkyl-$C_{1-3}$ alkylene, and 4-10 membered heterocycloalkyl-$C_{1-3}$ alkylene, are each optionally substituted with 1, 2, or 3 substituents independently selected from $R^{20}$;

Cy is selected from $C_{6-10}$ aryl and 5-10 membered heteroaryl; wherein the 5-10 membered heteroaryl each has at least one ring-forming carbon atom and 1, 2, 3, or 4 ring-forming heteroatoms independently selected from N and O; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, or 3 substituents independently selected from $R^{10}$;

$R^3$ is selected from H, $C_{1-6}$ alkyl, $C_{1-6}$ haloalkyl, halo, D, and CN;

$R^4$ is selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a4}$, and $NR^{c4}R^{d4}$;

$R^5$ is selected from $C_{1-6}$ alkyl, $C_{1-6}$ haloalkyl, 4-10 membered heterocycloalkyl, $C_{6-10}$ aryl, 5-10 membered heteroaryl, halo, D, $OR^{a5}$, and $NR^{c5}R^{d5}$; wherein said $C_{1-6}$ alkyl, 4-10 membered heterocycloalkyl, $C_{6-10}$ aryl, and 5-10 membered heteroaryl, are each optionally substituted with 1, 2, or 3 substituents independently selected from $R^{50}$;

ring A is selected from 4-10 membered heterocycloalkyl; wherein the 4-10 membered heterocycloalkyl has at least one ring-forming carbon atom and 1, 2, 3, or 4 ring-forming heteroatoms independently selected from N and O; wherein a ring-forming carbon atom of 4-10 membered heterocycloalkyl is optionally substituted by oxo to form a carbonyl group;

$R^6$ is selected from $C_{1-6}$ alkyl, $C_{1-6}$ haloalkyl, halo, D, CN, $OR^{a6}$, and $NR^{c6}R^{d6}$; wherein said $C_{1-6}$ alkyl is optionally substituted with 1, 2, or 3 substituents independently selected from $R^{60}$;

n is 0, 1, or 2;

each $R^{10}$ is independently selected from $C_{1-6}$ alkyl, $C_{1-6}$ haloalkyl, halo, D, CN, $OR^{a10}$, and $NR^{c10}R^{d10}$;

each $R^{20}$ is independently selected from $C_{1-6}$ alkyl, $C_{1-6}$ haloalkyl, halo, D, CN, $OR^{a20}$, and $NR^{c20}R^{d20}$;

each $R^{50}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a50}$, and $NR^{c50}R^{d50}$; wherein said $C_{1-6}$ alkyl, $C_{3-10}$ cycloalkyl, and 4-10 membered heterocycloalkyl, are each optionally substituted with 1, 2, or 3 substituents independently selected from $R^{51}$;

each $R^{51}$ is independently selected from $C_{1-6}$ alkyl, $C_{1-6}$ haloalkyl, halo, D, CN, $OR^{a51}$, and $NR^{c51}R^{d51}$;

each $R^{60}$ is independently selected from $C_{1-6}$ alkyl, $C_{1-6}$ haloalkyl, halo, D, CN, $OR^{a60}$, and $NR^{c60}R^{d60}$;

each $R^{a2}$, $R^{c2}$ and $R^{d2}$ is independently selected from H, $C_{1-6}$ alkyl, and $C_{1-6}$ haloalkyl; wherein said $C_{1-6}$ alkyl, is optionally substituted with 1, 2, or 3 substituents independently selected from $R^{20}$;

each $R^{a4}$, $R^{b4}$, $R^{c4}$ and $R^{d4}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c4}$ and $R^{d4}$ attached to the same N atom, together with the N atom to which they are attached, form a 4-, 5-, or 6-membered heterocycloalkyl group;

each $R^{a5}$, $R^{c5}$, and $R^{d5}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, or 3 substituents independently selected from $R^{50}$;

or any $R^{c5}$ and $R^{d5}$ attached to the same N atom, together with the N atom to which they are attached, form a 4-, 5-, or 6-membered heterocycloalkyl group optionally substituted with 1, 2 or 3 substituents independently selected from $R^{50}$;

each $R^{a6}$, $R^{c6}$, and $R^{d6}$ is independently selected from H, $C_{1-6}$ alkyl, and $C_{1-6}$ haloalkyl; wherein said $C_{1-6}$ alkyl, is optionally substituted with 1, 2, or 3 substituents independently selected from $R^{60}$;

each $R^{a10}$, $R^{c10}$ and $R^{d10}$ is independently selected from H, $C_{1-6}$ alkyl, and $C_{1-6}$ haloalkyl;

each $R^{a20}$, $R^{c10}$ and $R^{d20}$ is independently selected from H, $C_{1-6}$ alkyl, and $C_{1-6}$ haloalkyl;

each $R^{a50}$, $R^{c50}$ and $R^{d50}$, is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, or 3 substituents independently selected from $R^{51}$;

or any $R^{c50}$ and $R^{d50}$ attached to the same N atom, together with the N atom to which they are attached, form a 4-, 5-, or 6-membered heterocycloalkyl group optionally substituted with 1, 2 or 3 substituents independently selected from $R^{51}$;

each $R^{a51}$, $R^{c51}$ and $R^{d51}$, is independently selected from H, $C_{1-6}$ alkyl, and $C_{1-6}$ haloalkyl; and each $R^{a60}$, $R^{c60}$ and $R^{d60}$ is independently selected from H, $C_{1-6}$ alkyl, and $C_{1-6}$ haloalkyl.

In still another embodiment or Formula I, or a pharmaceutically acceptable salt thereof, $R^1$ is selected from H, or $C_{1-6}$ alkyl;

X is N or $CR^2$;

$R^2$ is selected from H, and $C_{1-6}$ alkyl;

Cy is selected from $C_{6-10}$ aryl, optionally substituted with 1, 2, or 3 substituents independently selected from $R^{10}$;

$R^3$ is selected from H, $C_{1-6}$ alkyl, $C_{1-6}$ haloalkyl, halo, D, and CN;

$R^4$ is selected from $C_{1-6}$ alkyl, $C_{1-6}$ haloalkyl, $C_{3-10}$ cycloalkyl, $C_{6-10}$ aryl, halo, and CN;

$R^5$ is selected from $C_{1-6}$ alkyl, $C_{1-6}$ haloalkyl, 4-10 membered heterocycloalkyl, $C_{6-10}$ aryl, 5-10 membered heteroaryl, $OR^{a5}$, and $NR^{c5}R^{d5}$; wherein said $C_{1-6}$ alkyl, 4-10 membered heterocycloalkyl, $C_{6-10}$ aryl, and 5-10 membered heteroaryl, are each optionally substituted with 1, 2, or 3 substituents independently selected from $R^{50}$;

ring A is selected from 4-10 membered heterocycloalkyl; wherein the 4-10 membered heterocycloalkyl has at least one ring-forming carbon atom and 1, 2, 3, or 4 ring-forming heteroatoms independently selected from N and O; wherein a ring-forming carbon atom of 4-10 membered heterocycloalkyl is optionally substituted by oxo to form a carbonyl group;

$R^6$ is selected from $C_{1-6}$ alkyl, $OR^{a6}$, and $NR^{c6}R^{d6}$; wherein said $C_{1-6}$ alkyl, is optionally substituted with 1, 2, or 3 substituents independently selected from $R^{60}$;

n is 0, 1, or 2;

each $R^{10}$ is independently selected from $C_{1-6}$ alkyl, halo, CN, $OR^{a10}$, and $NR^{c10}R^{d10}$;

each $R^{50}$ is independently selected from $C_{1-6}$ alkyl, $C_{1-6}$ haloalkyl, $C_{3-10}$ cycloalkyl, 4-10 membered heterocycloalkyl, halo, $OR^{a50}$, and $NR^{c50}R^{d50}$; wherein said $C_{1-6}$ alkyl, $C_{3-10}$ cycloalkyl, and 4-10 membered heterocycloalkyl, are each optionally substituted with 1, 2, or 3 substituents independently selected from $R^{51}$;

each $R^{51}$ is independently selected from $C_{1-6}$ alkyl, $C_{1-6}$ haloalkyl, halo, D, CN, $OR^{a51}$, and $NR^{c51}R^{d51}$;

each $R^{60}$ is independently selected from $C_{1-6}$ alkyl, $C_{1-6}$ haloalkyl, halo, D, CN, $OR^{a60}$, and $NR^{c60}R^{d60}$;

each $R^{a5}$, $R^{c5}$, and $R^{d5}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, or 3 substituents independently selected from $R^{50}$;

or any $R^{c5}$ and $R^{d5}$ attached to the same N atom, together with the N atom to which they are attached, form a 4-, 5-, or 6-membered heterocycloalkyl group optionally substituted with 1, 2 or 3 substituents independently selected from $R^{50}$;

each $R^{a6}$, $R^{c6}$, and $R^{d6}$ is independently selected from H, $C_{1-6}$ alkyl, and $C_{1-6}$ haloalkyl; wherein said $C_{1-6}$ alkyl, is optionally substituted with 1, 2, or 3 substituents independently selected from $R^{60}$;

each $R^{a10}$, $R^{c10}$ and $R^{d10}$ is independently selected from H, $C_{1-6}$ alkyl, and $C_{1-6}$ haloalkyl;

each $R^{a50}$, $R^{c50}$ and $R^{d50}$, is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, or 3 substituents independently selected from $R^{51}$;

or any $R^{c50}$ and $R^{d50}$ attached to the same N atom, together with the N atom to which they are attached, form a 4-, 5-, or 6-membered heterocycloalkyl group optionally substituted with 1, 2 or 3 substituents independently selected from $R^{51}$;

each $R^{a51}$, $R^{c51}$ and $R^{d51}$, is independently selected from H, $C_{1-6}$ alkyl, and $C_{1-6}$ haloalkyl; and each $R^{a60}$, $R^{c60}$ and $R^{d60}$ is independently selected from H, $C_{1-6}$ alkyl, and $C_{1-6}$ haloalkyl.

In an embodiment of Formula I, or a pharmaceutically acceptable salt thereof, $R^1$ is H;

X is $CR^2$;

$R^2$ is H or $C_{1-6}$ alkyl optionally substituted with 1 or 2 substituents independently selected from $R^{20}$;

Cy is naphthalene optionally substituted with 1, 2, or 3 substituents independently selected from $R^{10}$;

$R^3$ is halo;

$R^4$ is selected from $C_{1-6}$ alkyl, $C_{3-10}$ cycloalkyl, $C_{6-10}$ aryl, halo, and, CN;

$R^5$ is selected from 4-10 membered heterocycloalkyl, $C_{6-10}$ aryl, and $OR^{a5}$; wherein said 4-10 membered heterocycloalkyl and $C_{6-10}$ aryl are each optionally substituted with 1, 2, or 3 substituents independently selected from $R^{50}$;

ring A is selected from 4-8 membered heterocycloalkyl; wherein the 4-8 membered heterocycloalkyl has at least one ring-forming carbon atom and 1, 2, 3, or 4 ring-forming heteroatoms independently selected from N and O; wherein a ring-forming carbon atom of 4-8 membered heterocycloalkyl is optionally substituted by oxo to form a carbonyl group;

$R^6$ is $C_{1-6}$ alkyl or $NH_2$, wherein said $C_{1-6}$ alkyl is optionally substituted with 1, 2, or 3 substituents independently selected from $R^{60}$;

n is 0, 1, or 2;

each $R^{10}$ is OH;

each $R^{20}$ is CN;

each $R^{50}$ is independently selected from $C_{1-6}$ alkyl, 4-10 membered heterocycloalkyl, and $N(C_{1-6}$ alkyl$)_2$; wherein said $C_{1-6}$ alkyl and 4-10 membered heterocycloalkyl, are each optionally substituted with 1, 2, or 3 substituents independently selected from $R^{51}$;

each $R^{51}$ is independently selected from $C_{1-6}$ alkyl and $N(C_{1-6}$ alkyl$)_2$;

each $R^{60}$ is independently selected from CN and OH; and each $R^{a5}$ is independently selected from $C_{1-6}$ alkyl and 4-10 membered heterocycloalkyl; wherein said $C_{1-6}$ alkyl and 4-10 membered heterocycloalkyl are each optionally substituted with 1, 2, or 3 substituents independently selected from $R^{50}$.

In another embodiment of Formula I, or a pharmaceutically acceptable salt thereof, $R^1$ is selected from H, D, $C_{1-6}$ alkyl, $C_{1-6}$ haloalkyl, halo, and CN;

X is N or $CR^2$;

$R^2$ is selected from H, $C_{1-6}$ alkyl, $C_{1-6}$ haloalkyl, $C_{3-10}$ cycloalkyl-$C_{1-3}$ alkylene, 4-10 membered heterocycloalkyl-$C_{1-3}$ alkylene, halo, D, CN, $OR^{a2}$, $C(O)NR^{c2}R^{d2}$, and $NR^{c2}R^{d2}$; wherein said $C_{1-6}$ alkyl, $C_{3-10}$ cycloalkyl-$C_{1-3}$ alkylene, and 4-10 membered heterocycloalkyl-$C_{1-3}$ alkylene, are each optionally substituted with 1, 2, or 3 substituents independently selected from $R^{20}$;

Cy is selected from $C_{6-10}$ aryl and 5-10 membered heteroaryl; wherein the 5-10 membered heteroaryl each has at least one ring-forming carbon atom and 1, 2, 3, or 4 ring-forming heteroatoms independently selected from N and O; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, or 3 substituents independently selected from $R^{10}$;

$R^3$ is selected from H, $C_{1-6}$ alkyl, $C_{1-6}$ haloalkyl, halo, D, and CN;

$R^4$ is selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a4}$, and $NR^{c4}R^{d4}$;

$R^5$ is selected from $C_{1-6}$ alkyl, $C_{1-6}$ haloalkyl, 4-10 membered heterocycloalkyl, $C_{6-10}$ aryl, 5-10 membered heteroaryl, halo, D, $OR^{a5}$, and $NR^{c5}R^{d5}$; wherein said $C_{1-6}$ alkyl, 4-10 membered heterocycloalkyl, $C_{6-10}$ aryl, and 5-10 membered heteroaryl, are each optionally substituted with 1, 2, or 3 substituents independently selected from $R^{50}$;

ring A is selected from 4-10 membered heterocycloalkyl; wherein the 4-10 membered heterocycloalkyl has at least one ring-forming carbon atom and 1, 2, 3, or 4 ring-forming heteroatoms independently selected from N and O; wherein a ring-forming carbon atom of 4-10 membered heterocycloalkyl is optionally substituted by oxo to form a carbonyl group;

$R^6$ is selected from $C_{1-6}$ alkyl, $C_{1-6}$ haloalkyl, halo, D, CN, $OR^{a6}$, and $NR^{c6}R^{d6}$; wherein said $C_{1-6}$ alkyl, is optionally substituted with 1, 2, or 3 substituents independently selected from $R^{60}$;

n is 0, 1, or 2;

each $R^{10}$ is independently selected from $C_{1-6}$ alkyl, $C_{1-6}$ haloalkyl, halo, D, CN, $OR^{a10}$, and $NR^{c10}R^{d10}$;

each $R^{20}$ is independently selected from $C_{1-6}$ alkyl, $C_{1-6}$ haloalkyl, halo, D, CN, $OR^{a20}$, and $NR^{c20}R^{d20}$;

each $R^{50}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a50}$, and $NR^{c50}R^{d50}$; wherein said $C_{1-6}$ alkyl, $C_{3-10}$ cycloalkyl, and 4-10 membered heterocycloalkyl, are each optionally substituted with 1, 2, or 3 substituents independently selected from $R^{51}$;

each $R^{51}$ is independently selected from $C_{1-6}$ alkyl, $C_{1-6}$ haloalkyl, halo, D, CN, $OR^{a51}$, and $NR^{c51}R^{d51}$;

each $R^{60}$ is independently selected from $C_{1-6}$ alkyl, $C_{1-6}$ haloalkyl, halo, D, CN, $OR^{a60}$, and $NR^{c60}R^{d60}$;

each $R^{a2}$, $R^{c2}$ and $R^{d2}$ is independently selected from H, $C_{1-6}$ alkyl, and $C_{1-6}$ haloalkyl; wherein said $C_{1-6}$ alkyl, is optionally substituted with 1, 2, or 3 substituents independently selected from $R^{20}$;

each $R^{a4}$, $R^{b4}$, $R^{c4}$ and $R^{d4}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c4}$ and $R^{d4}$ attached to the same N atom, together with the N atom to which they are attached, form a 4-, 5-, or 6-membered heterocycloalkyl group;

each $R^{a5}$, $R^{c5}$, and $R^{d5}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, or 3 substituents independently selected from $R^{50}$;

or any $R_{c5}$ and $R^{d5}$ attached to the same N atom, together with the N atom to which they are attached, form a 4-, 5-, or 6-membered heterocycloalkyl group optionally substituted with 1, 2 or 3 substituents independently selected from $R^{50}$;

each $R^{a6}$, $R^{c6}$, and $R^{d6}$ is independently selected from H, $C_{1-6}$ alkyl, and $C_{1-6}$ haloalkyl; wherein said $C_{1-6}$ alkyl, is optionally substituted with 1, 2, or 3 substituents independently selected from $R^{60}$;

each $R^{a10}$, $R^{c10}$ and $R^{d10}$ is independently selected from H, $C_{1-6}$ alkyl, and $C_{1-6}$ haloalkyl;

each $R^{a20}$, $R^{c20}$ and $R^{d20}$ is independently selected from H, $C_{1-6}$ alkyl, and $C_{1-6}$ haloalkyl;

each $R^{a50}$, $R^{c50}$ and $R^{d50}$, is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, or 3 substituents independently selected from $R^{51}$;

or any $R^{c50}$ and $R^{d50}$ attached to the same N atom, together with the N atom to which they are attached, form a 4-, 5-, or 6-membered heterocycloalkyl group optionally substituted with 1, 2 or 3 substituents independently selected from $R^{51}$;

each $R^{a51}$, $R^{c51}$ and $R^{d51}$, is independently selected from H, $C_{1-6}$ alkyl, and $C_{1-6}$ haloalkyl; and each $R^{a60}$, $R^{c60}$ and $R^{d60}$ is independently selected from H, $C_{1-6}$ alkyl, and $C_{1-6}$ haloalkyl.

In another embodiment of Formula I, or a pharmaceutically acceptable salt thereof, $R^1$ is selected from H, D, $C_{1-6}$ alkyl, $C_{1-6}$ haloalkyl, halo, and CN;

X is N or $CR^2$;

$R^2$ is selected from H and $C_{1-6}$ alkyl, wherein said $C_{1-6}$ alkyl is optionally substituted with 1, 2, or 3 substituents independently selected from $R^{20}$;

Cy is selected from $C_{6-10}$ aryl optionally substituted with 1, 2, or 3 substituents independently selected from $R^{10}$;

$R^3$ is halo;

$R^4$ is selected from $C_{1-6}$ alkyl, $C_{3-10}$ cycloalkyl, $C_{6-10}$ aryl, halo, and CN;

$R^5$ is selected from 4-10 membered heterocycloalkyl, $C_{6-10}$ aryl, and $OR^{a5}$; wherein said 4-10 membered heterocycloalkyl and $C_{6-10}$ aryl are each optionally substituted with 1, 2, or 3 substituents independently selected from $R^{50}$;

ring A is 4-10 membered heterocycloalkyl; wherein the 4-10 membered heterocycloalkyl has at least one ring-forming carbon atom and 1, 2, 3, or 4 ring-forming heteroatoms independently selected from N and O; wherein a ring-forming carbon atom of 4-10 membered heterocycloalkyl is optionally substituted by oxo to form a carbonyl group;

$R^6$ is selected from $C_{1-6}$ alkyl and $NR^{c6}R^{d6}$;

n is 0 or 1;

each $R^{10}$ is independently selected from $C_{1-6}$ alkyl, halo, and $OR^{a10}$;

each $R^{20}$ is CN;

each $R^{50}$ is independently selected from $C_{1-6}$ alkyl, 4-10 membered heterocycloalkyl, and $NR^{c50}R^{d50}$; wherein said $C_{1-6}$ alkyl and 4-10 membered heterocycloalkyl, are each optionally substituted with 1, 2, or 3 substituents independently selected from $R^{51}$;

each $R^{51}$ is independently selected from $C_{1-6}$ alkyl, halo, and $NR^{c51}R^{d51}$;

each $R^{60}$ is independently selected from CN and $OR^{a60}$;

each $R^{a5}$ is independently selected from $C_{1-6}$ alkyl and 4-10 membered heterocycloalkyl; wherein said $C_{1-6}$ alkyl and 4-10 membered heterocycloalkyl are each optionally substituted with 1, 2, or 3 substituents independently selected from $R^{50}$;

each $R^{c6}$ and $R^{d6}$ is H;

each $R^{a10}$ is H;

each $R^{c50}$ and $R^{d50}$ is $C_{1-6}$ alkyl optionally substituted with 1, 2, or 3 substituents independently selected from $R^{51}$;

each $R^{c51}$ and $R^{d51}$ is $C_{1-6}$ alkyl; and each $R^{a60}$ is H.

In yet another embodiment of Formula I, or a pharmaceutically acceptable salt thereof, $R^1$ is H;

X is N or $CR^2$;

$R^2$ is selected from H and $C_{1-6}$ alkyl, wherein said $C_{1-6}$ alkyl is optionally substituted with 1, 2, or 3 substituents independently selected from $R^{20}$;

Cy is selected from $C_{6-10}$ aryl optionally substituted with 1, 2, or 3 substituents independently selected from $R^{10}$;

R³ is halo;
R⁴ is selected from $C_{1-6}$ alkyl, $C_{3-8}$ cycloalkyl, phenyl, halo, and CN;
R⁵ is selected from 4-10 membered heterocycloalkyl, phenyl, and $OR^{a5}$; wherein said 4-10 membered heterocycloalkyl and phenyl are optionally substituted with 1, 2, or 3 substituents independently selected from $R^{50}$;
ring A is 4-10 membered heterocycloalkyl; wherein the 4-10 membered heterocycloalkyl has at least one ring-forming carbon atom and 1, 2, 3, or 4 ring-forming heteroatoms independently selected from N and O; wherein a ring-forming carbon atom of 4-10 membered heterocycloalkyl is optionally substituted by oxo to form a carbonyl group;
each R⁶ is independently selected from $C_{1-6}$ alkyl and $NH_2$, wherein said $C_{1-6}$ alkyl is optionally substituted with OH or CN;
n is 0, 1, or 2;
each $R^{10}$ is independently selected from $C_{1-6}$ alkyl, halo, and OH;
each $R^{20}$ is CN;
each $R^{50}$ is independently selected from $C_{1-6}$ alkyl, 4-10 membered heterocycloalkyl, and $NR^{c50}R^{d50}$; wherein said $C_{1-6}$ alkyl and 4-10 membered heterocycloalkyl, are each optionally substituted with 1, 2, or 3 substituents independently selected from $R^{51}$;
each $R^{51}$ is independently selected from $C_{1-3}$ alkyl, $N(C_{1-3}$ alkyl$)_2$, and halo;
each $R^{a5}$ is independently selected from $C_{1-6}$ alkyl and 4-10 membered heterocycloalkyl; wherein said $C_{1-8}$ alkyl and 4-10 membered heterocycloalkyl are each optionally substituted with 1 or 2 substituents independently selected from $R^{50}$; and
each $R^{c50}$ and $R^{d50}$ is $C_{1-6}$ alkyl.

In yet another embodiment of Formula I, or a pharmaceutically acceptable salt thereof,
R¹ is H;
X is N;
Cy is selected from $C_{6-10}$ aryl optionally substituted with 1, 2, or 3 substituents independently selected from $R^{10}$;
R³ is halo;
R⁴ is CN;
R⁵ is selected from 4-10 membered heterocycloalkyl and $OR^{a5}$; wherein said 4-10 membered heterocycloalkyl is optionally substituted with 1, 2, or 3 substituents independently selected from $R^{50}$;
ring A is 4-10 membered heterocycloalkyl; wherein the 4-10 membered heterocycloalkyl has at least one ring-forming carbon atom and 1, 2, 3, or 4 ring-forming heteroatoms independently selected from N and O; wherein a ring-forming carbon atom of 4-10 membered heterocycloalkyl is optionally substituted by oxo to form a carbonyl group;
n is 0;
each $R^{10}$ is independently selected from $C_{1-6}$ alkyl, halo, and OH;
each $R^{50}$ is independently selected from $C_{1-6}$ alkyl, 4-10 membered heterocycloalkyl, and $NR^{c50}R^{d50}$; wherein said $C_{1-6}$ alkyl and 4-10 membered heterocycloalkyl, are each optionally substituted with 1, 2, or 3 substituents independently selected from $R^{51}$;
each $R^{51}$ is halo;
each $R^{a5}$ is $C_{1-6}$ alkyl optionally substituted with 1, 2, or 3 substituents independently selected from $R^{50}$; and
each $R^{c50}$ and $R^{d50}$ is $C_{1-6}$ alkyl.

In another embodiment, the compound of Formula I is a compound of Formula II:

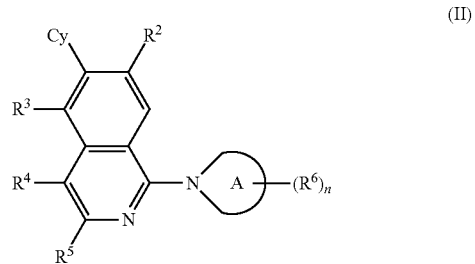

(II)

or a pharmaceutically acceptable salt thereof.

In yet another embodiment, R¹ is selected from H, $C_{1-6}$ alkyl, $C_{1-6}$ haloalkyl, halo, and CN. In still another embodiment, R¹ is H.

In an embodiment, X is CR². In another embodiment, X is N.

In yet another embodiment, R² is selected from H, $C_{1-6}$ alkyl, $C_{1-6}$ haloalkyl, halo, D, and CN; wherein said $C_{1-6}$ alkyl is optionally substituted with 1 or 2 substituents independently selected from $R^{20}$. In still another embodiment, R² is H or $C_{1-6}$ alkyl optionally substituted with CN.

In an embodiment, Cy is selected from $C_{6-10}$ aryl and 5-10 membered heteroaryl; wherein the 5-10 membered heteroaryl each has at least one ring-forming carbon atom and 1, 2, 3, or 4 ring-forming heteroatoms independently selected from N and O; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1 or 2 substituents independently selected from $R^{10}$.

In another embodiment, Cy is $C_{6-10}$ aryl optionally substituted with 1 or 2 substituents independently selected from $R^{10}$. In yet another embodiment, Cy is $C_{10}$ aryl optionally substituted with 1 or 2 substituents independently selected from $R^{10}$.

In still another embodiment, R³ is selected from H, $C_{1-6}$ alkyl, $C_{1-6}$ haloalkyl, and halo. In another embodiment, R³ is halo.

In an embodiment, R⁴ is selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, and CN. In another embodiment, R⁴ is selected from $C_{1-6}$ alkyl, $C_{3-10}$ cycloalkyl, $C_{6-10}$ aryl, halo, and, CN.

In an embodiment, R⁵ is selected from $C_{1-6}$ alkyl, $C_{1-6}$ haloalkyl, 4-10 membered heterocycloalkyl, $C_{6-10}$ aryl, 5-10 membered heteroaryl, halo, D, $OR^{a5}$, and $NR^{c5}R^{d5}$; wherein said $C_{1-6}$ alkyl, 4-10 membered heterocycloalkyl, $C_{6-10}$ aryl, and 5-10 membered heteroaryl, are each optionally substituted with 1, 2, or 3 substituents independently selected from $R^{50}$. In yet another embodiment, R⁵ is selected from 4-6 membered heterocycloalkyl, $C_{6-10}$ aryl, and $OR^{a5}$; wherein said 4-6 membered heterocycloalkyl and $C_{6-10}$ aryl, are each optionally substituted with 1 or 2 substituents independently selected from $R^{50}$.

In an embodiment, ring A is selected from 4-10 membered heterocycloalkyl; wherein the 4-10 membered heterocycloalkyl has at least one ring-forming carbon atom and 1, 2, 3, or 4 ring-forming heteroatoms independently selected from N and O; wherein a ring-forming carbon atom of 4-10 membered heterocycloalkyl is optionally substituted by oxo to form a carbonyl group. In still another embodiment, ring A is selected from 4-8 membered heterocycloalkyl; wherein the 4-8 membered heterocycloalkyl has at least one ring-forming carbon atom and 1, 2, 3, or 4 ring-forming heteroatoms independently selected from N and O.

In an embodiment, $R^6$ is selected from $C_{1-6}$ alkyl, $C_{1-6}$ haloalkyl, halo, D, CN, $OR^{a6}$, and $NR^{c6}R^{d6}$; wherein said $C_{1-6}$ alkyl is optionally substituted with 1, 2, or 3 substituents independently selected from $R^{60}$. In another embodiment, $R^6$ is $C_{1-6}$ alkyl or $NH_2$, wherein said $C_{1-6}$ alkyl is optionally substituted with 1, 2, or 3 substituents independently selected from CN and OH.

In yet another embodiment, each $R^{20}$ is independently selected from $C_{1-6}$ alkyl, $C_{1-6}$ haloalkyl, halo, and CN. In still another embodiment, each $R^{20}$ is CN.

In an embodiment, each $R^{10}$ is independently selected from $C_{1-6}$ alkyl, $C_{1-6}$ haloalkyl, halo, CN, and OH. In an embodiment, each $R^{10}$ is independently selected from $C_{1-6}$ haloalkyl, halo, CN, and OH. In an embodiment, each $R^{10}$ is independently selected from $C_{1-6}$ alkyl, halo, and OH. In another embodiment, each $R^{10}$ is OH. In another embodiment, each $R^{10}$ is ethyl, fluoro, and OH.

In an embodiment, $R^6$ is selected from $C_{1-6}$ alkyl and $C(O)R^{b6}$; wherein said $C_{1-6}$ alkyl is optionally substituted with 1 or 2 substituents independently selected from $R^{60}$. In another embodiment, each $R^{b6}$ is independently selected from $C_{2-6}$ alkenyl and $C_{2-6}$ alkynyl. In yet another embodiment, each $R^{60}$ is independently selected from CN and halo.

In an embodiment, n is 0, 1, or 2. In another embodiment, n is 1. In yet another embodiment, n is 0.

In yet another embodiment, each $R^{a5}$ is independently selected from H, $C_{1-6}$ alkyl, $C_{1-6}$ haloalkyl, and 4-10 membered heterocycloalkyl; wherein said $C_{1-6}$ alkyl, and 4-10 membered heterocycloalkyl are each optionally substituted with 1, 2, or 3 substituents independently selected from $R^{50}$. In still another embodiment, each $R^{a5}$ is independently selected from $C_{1-6}$ alkyl and 4-10 membered heterocycloalkyl; wherein said $C_{1-6}$ alkyl and 4-10 membered heterocycloalkyl are each optionally substituted with 1, 2, or 3 substituents independently selected from $R^{50}$.

In an embodiment, each $R^{50}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a50}$, and $NR^{c50}R^{d50}$; wherein said $C_{1-6}$ alkyl, $C_{3-10}$ cycloalkyl, and 4-10 membered heterocycloalkyl, are each optionally substituted with 1, 2, or 3 substituents independently selected from $R^{51}$. In another embodiment, each $R^{50}$ is independently selected from $C_{1-6}$ alkyl, 4-10 membered heterocycloalkyl, and $N(C_{1-6}$ alkyl$)_2$; wherein said $C_{1-6}$ alkyl and 4-10 membered heterocycloalkyl, are each optionally substituted with 1, 2, or 3 substituents independently selected from $C_{1-6}$ alkyl and $N(C_{1-6}$ alkyl$)_2$.

In yet another embodiment, each $R^{51}$ is independently selected from $C_{1-6}$ alkyl, $C_{1-6}$ haloalkyl, halo, D, CN, $OR^{a51}$, and $NR^{c51}R^{d51}$. In still another embodiment, each $R^{51}$ is independently selected from $C_{1-6}$ alkyl and $NR^{c51}R^{d51}$. In still another embodiment, each $R^{51}$ is independently selected from $C_{1-6}$ alkyl, halo, and $NR^{c51}R^{d51}$.

In an embodiment, each $R^{60}$ is independently selected from $C_{1-6}$ alkyl, $C_{1-6}$ haloalkyl, halo, D, CN, $OR^{a60}$, and $NR^{c60}R^{d60}$. In an embodiment, each $R^{60}$ is independently selected from CN and $OR^{a60}$.

In another embodiment, the compound of Formula I is selected from 1-(3,8-diazabicyclo[3.2.1]octan-8-yl)-3-(3-(dimethylamino) azetidin-1-yl)-5-fluoro-6-(3-hydroxynaphthalen-1-yl)isoquinoline-4-carbonitrile;

3-(1-(3,8-diazabicyclo[3.2.1]octan-8-yl)-4-chloro-3-(3-(dimethylamino)azetidin-1-yl)-5-fluoro-6-(3-hydroxynaphthalen-1-yl)isoquinolin-7-yl)propanenitrile;

3-(1-(3,8-diazabicyclo[3.2.1]octan-8-yl)-3-(3-(dimethylamino)azetidin-1-yl)-5-fluoro-6-(3-hydroxynaphthalen-1-yl)-4-methylisoquinolin-7-yl)propanenitrile;

3-(1-(3,8-diazabicyclo[3.2.1]octan-8-yl)-3-(3-(dimethylamino)azetidin-1-yl)-5-fluoro-6-(3-hydroxynaphthalen-1-yl)-4-phenylisoquinolin-7-yl)propanenitrile;

3-(1-(3,8-diazabicyclo[3.2.1]octan-8-yl)-4-cyclopropyl-3-(3-(dimethylamino)azetidin-1-yl)-5-fluoro-6-(3-hydroxynaphthalen-1-yl)isoquinolin-7-yl)propanenitrile;

1-(3,8-diazabicyclo[3.2.1]octan-8-yl)-7-(2-cyanoethyl)-3-(3-(dimethylamino)azetidin-1-yl)-5-fluoro-6-(3-hydroxynaphthalen-1-yl)isoquinoline-4-carbonitrile;

1-(3,8-diazabicyclo[3.2.1]octan-8-yl)-7-(2-cyanoethyl)-5-fluoro-6-(3-hydroxynaphthalen-1-yl)-3-(((S)-1-methylpyrrolidin-2-yl)methoxy)isoquinoline-4-carbonitrile;

1-(3,8-diazabicyclo[3.2.1]octan-8-yl)-7-(2-cyanoethyl)-5-fluoro-6-(3-hydroxynaphthalen-1-yl)-3-((1-methylpiperidin-4-yl)oxy)isoquinoline-4-carbonitrile;

1-(3,8-diazabicyclo[3.2.1]octan-8-yl)-7-(2-cyanoethyl)-3-(3-((dimethylamino)methyl)phenyl)-5-fluoro-6-(3-hydroxynaphthalen-1-yl)isoquinoline-4-carbonitrile;

1-((1R,4R)-2,5-diazabicyclo[2.2.2]octan-2-yl)-7-(2-cyanoethyl)-3-(3-(dimethylamino)azetidin-1-yl)-5-fluoro-6-(3-hydroxynaphthalen-1-yl)isoquinoline-4-carbonitrile;

1-((2S,4S)-4-amino-2-(hydroxymethyl)pyrrolidin-1-yl)-7-(2-cyanoethyl)-3-(3-(dimethylamino)azetidin-1-yl)-5-fluoro-6-(3-hydroxynaphthalen-1-yl)isoquinoline-4-carbonitrile;

7-(2-cyanoethyl)-1-(3-(cyanomethyl)pyrrolidin-1-yl)-3-(3-(dimethylamino)azetidin-1-yl)-5-fluoro-6-(3-hydroxynaphthalen-1-yl)isoquinoline-4-carbonitrile;

1-((S)-3-aminopyrrolidin-1-yl)-7-(2-cyanoethyl)-3-(3-(dimethylamino)azetidin-1-yl)-5-fluoro-6-(3-hydroxynaphthalen-1-yl)isoquinoline-4-carbonitrile; and 1-((2R,4S)-4-amino-2-methylpyrrolidin-1-yl)-7-(2-cyanoethyl)-3-(3-(dimethylamino)azetidin-1-yl)-5-fluoro-6-(3-hydroxynaphthalen-1-yl)isoquinoline-4-carbonitrile;

or a pharmaceutically acceptable salt thereof.

In yet another embodiment, the compound of Formula I is selected from 1-(3,8-diazabicyclo[3.2.1]octan-3-yl)-5-fluoro-3-(((2R,7aS)-2-fluorotetrahydro-1H-pyrrolizin-7a(5H)-yl)methoxy)-6-(3-hydroxynaphthalen-1-yl)-2,7-naphthyridine-4-carbonitrile; and 1-(3,8-diazabicyclo[3.2.1]octan-3-yl)-3-(3-(dimethylamino)-3-methylazetidin-1-yl)-6-(8-ethyl-7-fluoro-3-hydroxynaphthalen-1-yl)-5-fluoro-2,7-naphthyridine-4-carbonitrile;

or a pharmaceutically acceptable salt thereof.

In another aspect, provided herein is a pharmaceutical composition comprising the compound of Formula I, or a pharmaceutically acceptable salt thereof, and a pharmaceutically acceptable carrier.

In an aspect, provided herein is a method of inhibiting a KRAS protein harboring a G12C mutation, said method comprising contacting a compound of the instant disclosure with KRAS.

In another aspect, provided herein is a method of inhibiting a KRAS protein harboring a G12D mutation, said method comprising contacting a compound of the instant disclosure with KRAS.

In yet another aspect, provided herein is a method of inhibiting a KRAS protein harboring a G12V mutation, said method comprising contacting a compound of the instant disclosure with KRAS.

In an embodiment, compounds of the Formulae herein are compounds of the Formulae or pharmaceutically acceptable salts thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula I can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted," unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl," refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene," employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy," employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms. The term "$C_{n-m}$ dialkoxy" refers to a linking group of formula —O—($C_{n-m}$ alkyl)-O—, the alkyl group of which has n to m carbons. Example dialkyoxy groups include —OCH$_2$CH$_2$O— and OCH$_2$CH$_2$CH$_2$O—. In some embodiments, the two O atoms of a $C_{n-m}$ dialkoxy group may be attached to the same B atom to form a 5- or 6-membered heterocycloalkyl group.

The term "alkylthio," employed alone or in combination with other terms, refers to a group of formula —S-alkyl, wherein the alkyl group is as defined above.

The term "amino," employed alone or in combination with other terms, refers to a group of formula —NH$_2$, wherein the hydrogen atoms may be substituted with a substituent described herein. For example, "alkylamino" can refer to —NH(alkyl) and —N(alkyl)$_2$.

The term "carbonyl," employed alone or in combination with other terms, refers to a —C(=O)— group, which also may be written as C(O).

The term "cyano" or "nitrile" refers to a group of formula —C≡N, which also may be written as —CN.

The term "carbamyl," as used herein, refers to a —NHC(O)O— or —OC(O)NH— group, wherein the carbon atom is doubly bound to one oxygen atom, and singly bound to a nitrogen and second oxygen atom.

The terms "halo" or "halogen," used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CH_2F$, $CCl_3$, $CHCl_2$, $C_2Cl_5$ and the like. In some embodiments, the haloalkyl group is a fluoroalkyl group.

The term "haloalkoxy," employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" or "oxy" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfonyl" refers to a —$SO_2$— group wherein a sulfur atom is doubly bound to two oxygen atoms.

The term "sulfinyl" refers to a —SO— group wherein a sulfur atom is doubly bound to one oxygen atom.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments, aryl groups have 6 carbon atoms. In some embodiments, aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thio-phenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, isoindolyl, benzothiophenyl, benzofuranyl, benzisoxazolyl, imidazo[1,2-b]thiazolyl, purinyl, and the like. In some embodiments, the heteroaryl group is pyridone (e.g., 2-pyridone).

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or $S(O)_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 2,5-diazabicyclo[2.2.1]heptanyl; pyrrolidinyl; hexahydropyrrolo[3,4-b]pyrrol-1(2H)-yl; 1,6-dihydropyridinyl; morpholinyl; azetidinyl; piperazinyl; and 4,7-diazaspiro[2.5]octan-7-yl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term "compound" as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds provided herein can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high-performance liquid chromatography (HPLC) or thin layer chromatography (TLC).

The Schemes below provide general guidance in connection with preparing the compounds of the present disclosure. One skilled in the art would understand that the preparations shown in the Schemes can be modified or optimized using general knowledge of organic chemistry to prepare various compounds provided herein.

Scheme 1

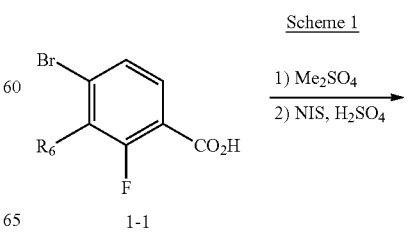

1-1

-continued

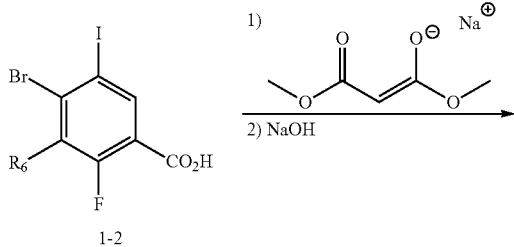
1-2

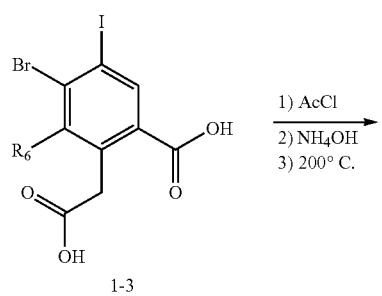
1-3

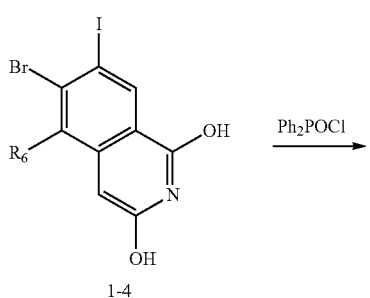
1-4

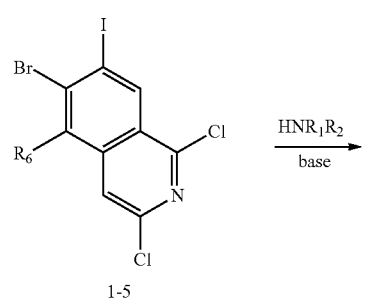
1-5

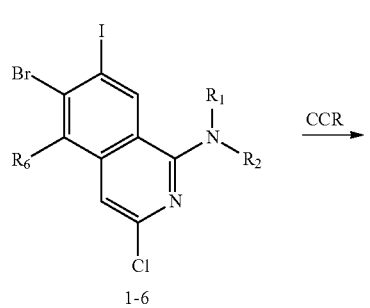
1-6

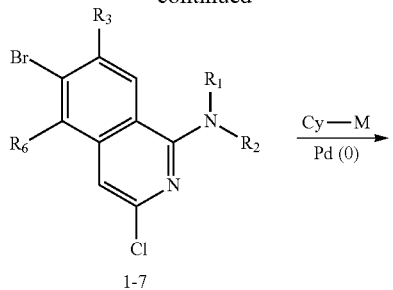
1-7

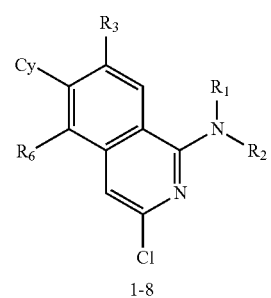
1-8

Some of the compounds in this invention can be prepared from intermediate 1-8, which can be prepared using the synthetic route in Scheme 1. Commercially available starting material 1-1 is first methylated, then iodinated under acidic conditions to provide intermediate 1-2. Reaction of this intermediate with the sodium enolate derived from dimethyl malonate, followed by global ester hydrolysis and decarboxylation, provides intermediate 1-3. A three-step cyclization sequence involving cyclic anhydride formation, cleavage with ammonium hydroxide and cyclization under high temperature conditions in an appropriate solvent (e.g. o-dichlorobenzene) provides intermediate 1-4. Chlorination with diphenyl phosphonyl chloride under high heat provides the desired dichloro intermediate 1-5. Reaction of this intermediate with a suitable cyclic amine provides compounds of general formula 1-6. Selective functionalization of the iodide is possible through a host of cross coupling reactions, such as the Heck reaction with olefins or with an appropriate $R_3$-M, where is M is a suitable metal such as $B(OH)_2$ for Suzuki coupling, $SnR_3$ for Stille coupling or XZn for Negishi coupling (where X is an appropriate halide, such as Cl or Br). These reactions can be performed under palladium catalysis using conditions known to those skilled in the art. Intermediates of general formula 1-7 can be further selectively functionalized at the chloride using a range of coupling partners and conditions similar to those described for the conversion of 1-6 to 1-7.

Scheme 2

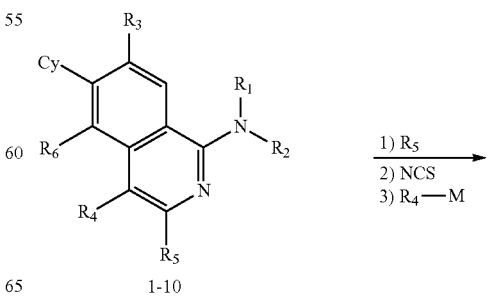
1-10

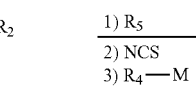
1) $R_5$
2) NCS
3) $R_4$—M

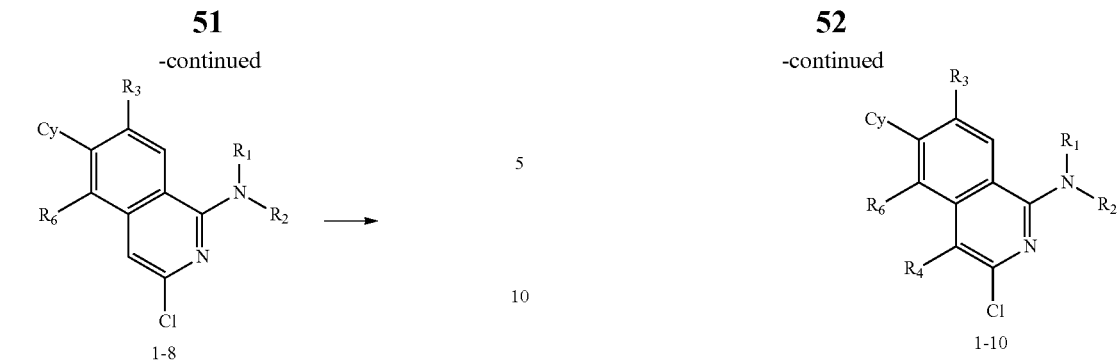

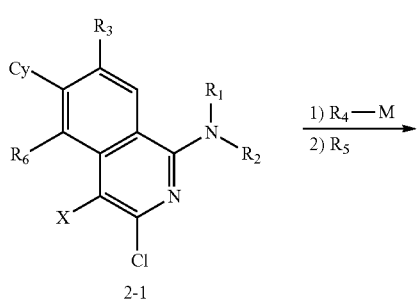

Intermediate 1-8 can be further functionalized depending on the nature of substitution, as shown in Scheme 2. If variation at $R_4$ is desired, the $R_5$ substituent is installed by the appropriate cross coupling reaction e.g. with a suitable $R_4$-M species as described above, or through a C—N or C—O Buchwald-Hartwig cross coupling with an appropriate amine or alcohol nucleophile, palladium source and base. Subsequent chlorination with NCS and an additional cross coupling reaction with a suitable $R_4$-M provides compounds of general formula 1-10 (Scheme 2, left). Alternatively, halogenation can be performed first to provide intermediate 2-1 with an appropriate halogen (i.e. X=Br or I). This intermediate can be selectively reacted with $R_4$-M as above, followed by cross coupling with an appropriate $R_5$ substituent to arrive at final products of formula of 1-10 (Scheme 2, right).

Scheme 3

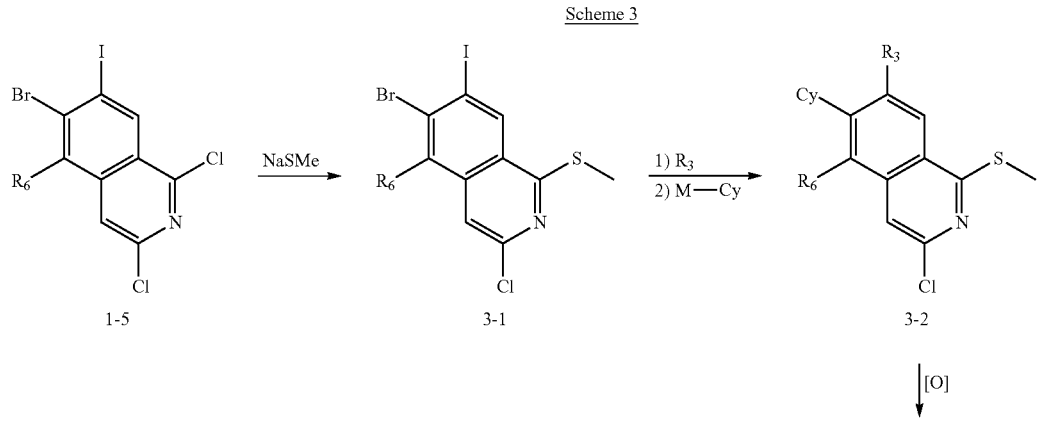

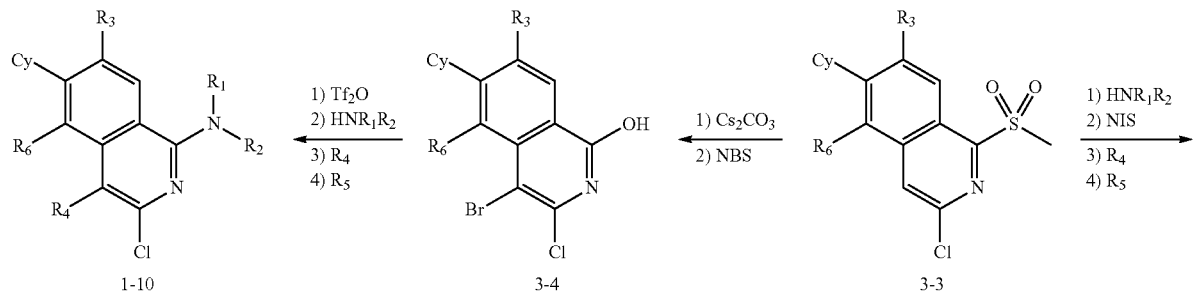

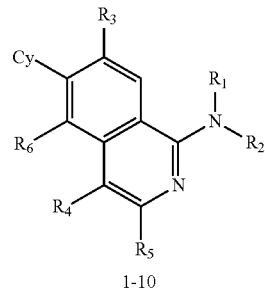

1-10

In an alternative route, compounds of formula 1-10 can be prepared by a synthetic route depicted in Scheme 3. Starting from intermediate 1-5, reaction with sodium thiomethoxide yields intermediate 3-1. The R$_3$ and Cy substituents can then be installed as described above to provide intermediate 3-2. Oxidation of the sulfur to the corresponding sulfone can be accomplished with standard reagents, i.e. m-CPBA. The resulting intermediate 3-3 can be functionalized by an appropriate amine directly, or first converted to the triflate by intermediacy of the hydroxyl bromo compound 3-4. Installation of the R$_4$ and R$_5$ substituents can be accomplished as described above.

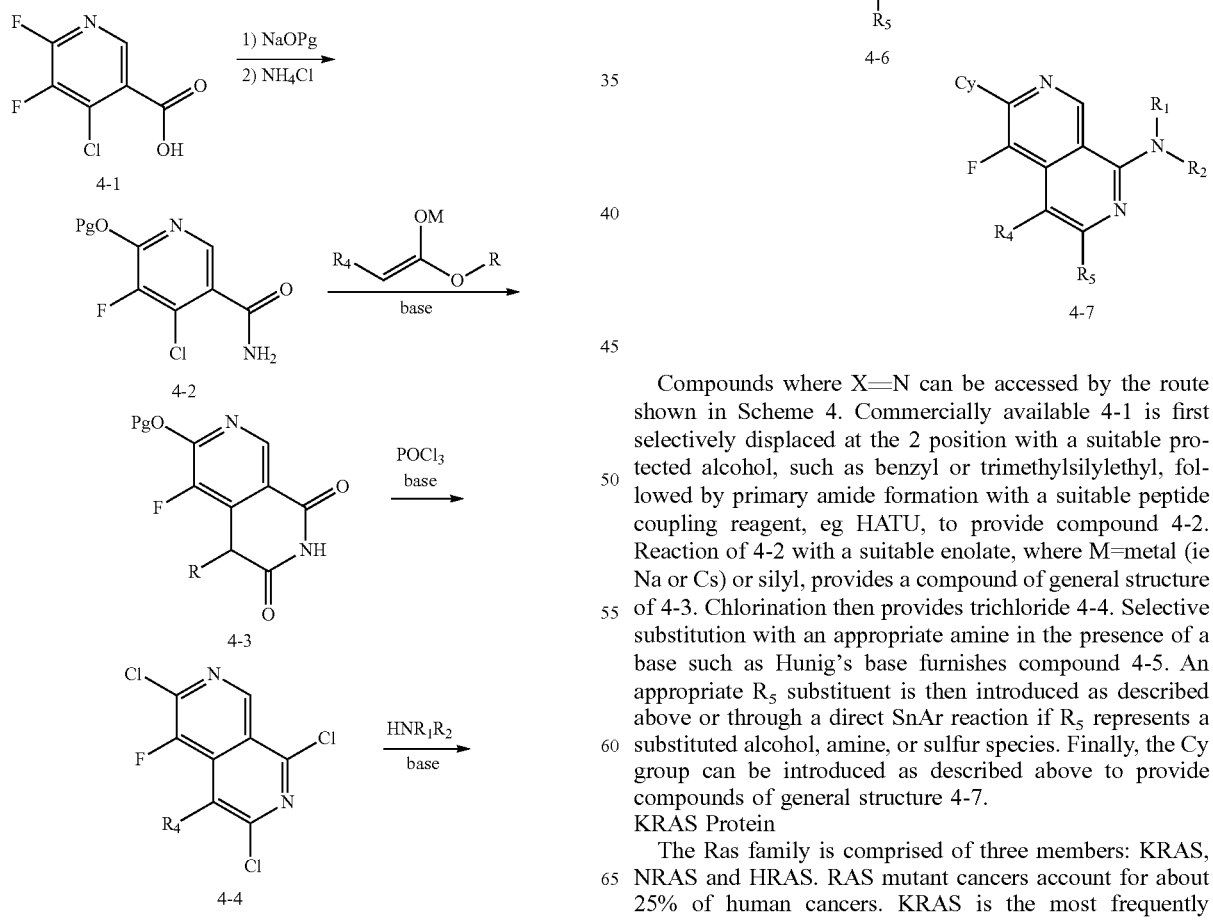

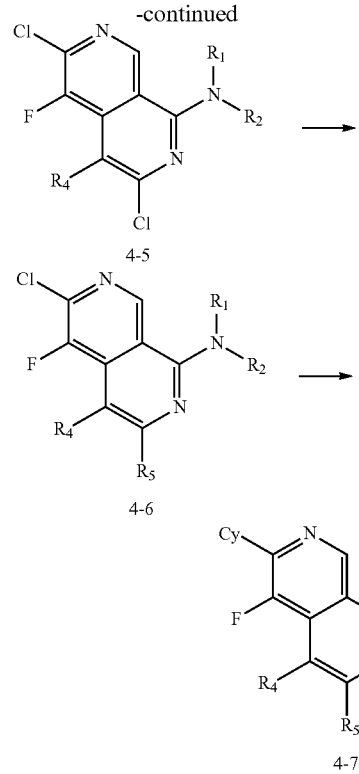

Compounds where X=N can be accessed by the route shown in Scheme 4. Commercially available 4-1 is first selectively displaced at the 2 position with a suitable protected alcohol, such as benzyl or trimethylsilylethyl, followed by primary amide formation with a suitable peptide coupling reagent, eg HATU, to provide compound 4-2. Reaction of 4-2 with a suitable enolate, where M=metal (ie Na or Cs) or silyl, provides a compound of general structure of 4-3. Chlorination then provides trichloride 4-4. Selective substitution with an appropriate amine in the presence of a base such as Hunig's base furnishes compound 4-5. An appropriate R$_5$ substituent is then introduced as described above or through a direct SnAr reaction if R$_5$ represents a substituted alcohol, amine, or sulfur species. Finally, the Cy group can be introduced as described above to provide compounds of general structure 4-7.

KRAS Protein

The Ras family is comprised of three members: KRAS, NRAS and HRAS. RAS mutant cancers account for about 25% of human cancers. KRAS is the most frequently mutated isoform in human cancers: 85% of all RAS mutations are in KRAS, 12% in NRAS, and 3% in HRAS (Simanshu, D. et al. Cell 170.1 (2017):17-33). KRAS mutations are prevalent amongst the top three most deadly cancer types: pancreatic (97%), colorectal (44%), and lung (30%) (Cox, A. D. et al. Nat Rev Drug Discov (2014) 13:828-51). The majority of RAS mutations occur at amino acid residues/codons 12, 13, and 61; Codon 12 mutations are most frequent in KRAS. The frequency of specific mutations varied between RAS genes and G12D mutations are most predominant in KRAS whereas Q61R and G12R mutations are most frequent in NRAS and HRAS. Furthermore, the spectrum of mutations in a RAS isoform differs between cancer types. For example, KRAS G12D mutations predominate in pancreatic cancers (51%), followed by colorectal adenocarcinomas (45%) and lung cancers (17%) (Cox, A. D. et al. Nat Rev Drug Discov (2014) 13:828-51). In contrast, KRAS G12C mutations predominate in non-small cell lung cancer (NSCLC) comprising 11-16% of lung adenocarcinomas (nearly half of mutant KRAS is G12C), as well as 2-5% of pancreatic and colorectal adenocarcinomas, respectively (Cox, A. D. et al. Nat. Rev. Drug Discov. (2014) 13:828-51). Using shRNA knockdown thousands of genes across hundreds of cancer cell lines, genomic studies have demonstrated that cancer cells exhibiting KRAS mutations are highly dependent on KRAS function for cell growth (McDonald, R. et al. Cell 170 (2017): 577-592). Taken together, these findings suggested that KRAS mutations play a critical role in human cancers, therefore development of the inhibitors targeting mutant KRAS may be useful in the clinical treatment of diseases that have characterized by a KRAS mutation.

Methods of Use

The cancer types in which KRAS harboring G12C, G12V, and G12D mutations are implicated include, but are not limited to: carcinomas (e.g., pancreatic, colorectal, lung, bladder, gastric, esophageal, breast, head and neck, cervical skin, thyroid); hematopoietic malignancies (e.g., myeloproliferative neoplasms (MPN), myelodysplastic syndrome (MDS), chronic and juvenile myelomonocytic leukemia (CMML and JMML), acute myeloid leukemia (AML), acute lymphocytic leukemia (ALL) and multiple myeloma (MM)); and other neoplasms (e.g., glioblastoma and sarcomas). In addition, KRAS mutations were found in acquired resistance to anti-EGFR therapy (Knickelbein, K. et al. Genes & Cancer, (2015): 4-12). KRAS mutations were found in immunological and inflammatory disorders (Fernandez-Medarde, A. et al. Genes & Cancer, (2011): 344-358) such as Ras-associated lymphoproliferative disorder (RALD) or juvenile myelomonocytic leukemia (JMML) caused by somatic mutations of KRAS or NRAS.

Compounds of the present disclosure can inhibit the activity of the KRAS protein. For example, compounds of the present disclosure can be used to inhibit activity of KRAS in a cell or in an individual or patient in need of inhibition of the enzyme by administering an inhibiting amount of one or more compounds of the present disclosure to the cell, individual, or patient.

As KRAS inhibitors, the compounds of the present disclosure are useful in the treatment of various diseases associated with abnormal expression or activity of KRAS. Compounds which inhibit KRAS will be useful in providing a means of preventing the growth or inducing apoptosis in tumors, or by inhibiting angiogenesis. It is therefore anticipated that compounds of the present disclosure will prove useful in treating or preventing proliferative disorders such as cancers. In particular, tumors with activating mutants of receptor tyrosine kinases or upregulation of receptor tyrosine kinases may be particularly sensitive to the inhibitors.

In an aspect, provided herein is a method of inhibiting KRAS activity, said method comprising contacting a compound of the instant disclosure with KRAS. In an embodiment, the contacting comprises administering the compound to a patient.

In another aspect, provided herein a is method of treating a disease or disorder associated with inhibition of KRAS interaction, said method comprising administering to a patient in need thereof a therapeutically effective amount of a compound of any of the formulae disclosed herein, or pharmaceutically acceptable salt thereof.

In an embodiment, the disease or disorder is an immunological or inflammatory disorder.

In another embodiment, the immunological or inflammatory disorder is Ras-associated lymphoproliferative disorder and juvenile myelomonocytic leukemia caused by somatic mutations of KRAS.

In an aspect, provided herein is a method of treating a disease or disorder associated with inhibiting a KRAS protein harboring a G12C mutation, said method comprising administering to a patient in need thereof a therapeutically effective amount of a compound of any of the formulae disclosed herein, or pharmaceutically acceptable salt thereof.

In another aspect, provided herein is a method of treating cancer in a patient in need thereof comprising administering to the patient a therapeutically effective amount of the compounds disclosed herein wherein the cancer is characterized by an interaction with a KRAS protein harboring a G12C mutation.

In another aspect, provided herein is a method of treating a disease or disorder associated with inhibiting a KRAS protein harboring a G12D mutation, said method comprising administering to a patient in need thereof a therapeutically effective amount of a compound of any of the formulae disclosed herein, or pharmaceutically acceptable salt thereof.

In yet another aspect, provided herein is also a method of treating cancer in a patient in need thereof comprising administering to the patient a therapeutically effective amount of the compounds disclosed herein wherein the cancer is characterized by an interaction with a KRAS protein harboring a G12D mutation.

In yet another aspect, provided herein is a method for treating a cancer in a patient, said method comprising administering to the patient a therapeutically effective amount of any one of the compounds disclosed herein, or pharmaceutically acceptable salt thereof.

In an embodiment, the cancer is selected from carcinomas, hematological cancers, sarcomas, and glioblastoma.

In another embodiment, the hematological cancer is selected from myeloproliferative neoplasms, myelodysplastic syndrome, chronic and juvenile myelomonocytic leukemia, acute myeloid leukemia, acute lymphocytic leukemia, and multiple myeloma.

In yet another embodiment, the carcinoma is selected from pancreatic,] colorectal, lung, bladder, gastric, esophageal, breast, head and neck, cervical, skin, and thyroid.

In still another aspect, provided herein is a method of treating a disease or disorder associated with inhibiting a KRAS protein harboring a G12C mutation, said method comprising administering to a patient in need thereof a therapeutically effective amount of the compound of any of the formulae disclosed herein, or a pharmaceutically acceptable salt thereof.

In another aspect, provided herein is a method for treating a disease or disorder associated with inhibition of KRAS interaction or a mutant thereof in a patient in need thereof comprising the step of administering to the patient a compound disclosed herein, or a pharmaceutically acceptable salt thereof, or a composition comprising a compound disclosed herein or a pharmaceutically acceptable salt thereof, in combination with another therapy or therapeutic agent as described herein.

In an embodiment, the cancer is selected from hematological cancers, sarcomas, lung cancers, gastrointestinal cancers, genitourinary tract cancers, liver cancers, bone cancers, nervous system cancers, gynecological cancers, and skin cancers.

In another embodiment, the lung cancer is selected from non-small cell lung cancer (NSCLC), small cell lung cancer, bronchogenic carcinoma, squamous cell bronchogenic carcinoma, undifferentiated small cell bronchogenic carcinoma, undifferentiated large cell bronchogenic carcinoma, adenocarcinoma, bronchogenic carcinoma, alveolar carcinoma, bronchiolar carcinoma, bronchial adenoma, chondromatous hamartoma, mesothelioma, pavicellular and non-pavicellular carcinoma, bronchial adenoma, and pleuropulmonary blastoma.

In yet another embodiment, the lung cancer is non-small cell lung cancer (NSCLC). In still another embodiment, the lung cancer is adenocarcinoma.

In an embodiment, the gastrointestinal cancer is selected from esophagus squamous cell carcinoma, esophagus adenocarcinoma, esophagus leiomyosarcoma, esophagus lymphoma, stomach carcinoma, stomach lymphoma, stomach leiomyosarcoma, exocrine pancreatic carcinoma, pancreatic ductal adenocarcinoma, pancreatic insulinoma, pancreatic glucagonoma, pancreatic gastrinoma, pancreatic carcinoid tumors, pancreatic vipoma, small bowel adenocarcinoma, small bowel lymphoma, small bowel carcinoid tumors, Kaposi's sarcoma, small bowel leiomyoma, small bowel hemangioma, small bowel lipoma, small bowel neurofibroma, small bowel fibroma, large bowel adenocarcinoma, large bowel tubular adenoma, large bowel villous adenoma, large bowel hamartoma, large bowel leiomyoma, colorectal cancer, gall bladder cancer, and anal cancer.

In an embodiment, the gastrointestinal cancer is colorectal cancer.

In another embodiment, the cancer is a carcinoma. In yet another embodiment, the carcinoma is selected from pancreatic carcinoma, colorectal carcinoma, lung carcinoma, bladder carcinoma, gastric carcinoma, esophageal carcinoma, breast carcinoma, head and neck carcinoma, cervical skin carcinoma, and thyroid carcinoma.

In still another embodiment, the cancer is a hematopoietic malignancy. In an embodiment, the hematopoietic malignancy is selected from multiple myeloma, acute myelogenous leukemia, and myeloproliferative neoplasms.

In another embodiment, the cancer is a neoplasm. In yet another embodiment, the neoplasm is glioblastoma or sarcomas.

In certain embodiments, the disclosure provides a method for treating a KRAS-mediated disorder in a patient in need thereof, comprising the step of administering to said patient a compound according to the invention, or a pharmaceutically acceptable composition thereof.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET), 8p11 myeloproliferative syndrome, myelodysplasia syndrome (MDS), T-cell acute lymphoblastic lymphoma (T-ALL), multiple myeloma, cutaneous T-cell lymphoma, adult T-cell leukemia, Waldenstrom's Macroglubulinemia, hairy cell lymphoma, marginal zone lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, lymphosarcoma, leiomyosarcoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, mesothelioma, pavicellular and non-pavicellular carcinoma, bronchial adenoma and pleuropulmonary blastoma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (exocrine pancreatic carcinoma, ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer, gall bladder cancer and anal cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) and urothelial carcinoma.

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors, neuro-ectodermal tumors), and spinal cord (neurofibroma, meningioma, glioma, sarcoma), neuroblastoma, Lhermitte-Duclos disease and pineal tumors.

Exemplary gynecological cancers include cancers of the breast (ductal carcinoma, lobular carcinoma, breast sarcoma, triple-negative breast cancer, HER2-positive breast cancer, inflammatory breast cancer, papillary carcinoma), uterus (endometrial carcinoma), cervix (cervical carcinoma, pretumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers, tumors of the eye, tumors of the lips and mouth and squamous head and neck cancer.

The compounds of the present disclosure can also be useful in the inhibition of tumor metastases.

In addition to oncogenic neoplasms, the compounds of the invention are useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes. In some embodiments, the present disclosure provides a method for treating a patient suffering from a skeletal and chondrocyte disorder.

In some embodiments, compounds described herein can be used to treat Alzheimer's disease, HIV, or tuberculosis.

As used herein, the term "8p11 myeloproliferative syndrome" is meant to refer to myeloid/lymphoid neoplasms associated with eosinophilia and abnormalities of FGFR1.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" KRAS with a compound described herein includes the administration of a compound described herein to an individual or patient, such as a human, having KRAS, as well as, for example, introducing a compound described herein into a sample containing a cellular or purified preparation containing KRAS.

As used herein, the term "individual," "subject," or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy*, 21st ed.; Lippincott Williams & Wilkins: Philadelphia, Pa., 2005; *Handbook of Pharmaceutical Excipients*, *6th ed.*; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, *2nd ed.*; Gibson Ed.; CRC Press LLC: Boca Raton, Fla., 2009.

As used herein, the term "treating" or "treatment" refers to inhibiting a disease; for example, inhibiting a disease, condition, or disorder in an individual who is experiencing or displaying the pathology or symptomology of the disease, condition, or disorder (i.e., arresting further development of the pathology and/or symptomology) or ameliorating the disease; for example, ameliorating a disease, condition, or disorder in an individual who is experiencing or displaying the pathology or symptomology of the disease, condition, or disorder (i.e., reversing the pathology and/or symptomology) such as decreasing the severity of the disease.

The term "prevent," "preventing," or "prevention" as used herein, comprises the prevention of at least one symptom associated with or caused by the state, disease or disorder being prevented.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapies
I. Cancer Therapies

Cancer cell growth and survival can be impacted by dysfunction in multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, FAK, and CDK4/6 kinase inhibitors such as, for example, those described in WO 2006/056399 can be used in combination with the compounds of the present disclosure for treatment of CDK2-associated diseases, disorders or conditions. Other agents such as therapeutic antibodies can be used in combination with the compounds of the present disclosure for treatment of CDK2-associated diseases, disorders or conditions. The one or more additional pharmaceutical agents can be administered to a patient simultaneously or sequentially.

In some embodiments, the CDK2 inhibitor is administered or used in combination with a BCL2 inhibitor or a CDK4/6 inhibitor.

The compounds as disclosed herein can be used in combination with one or more other enzyme/protein/receptor inhibitors therapies for the treatment of diseases, such as cancer and other diseases or disorders described herein. Examples of diseases and indications treatable with combination therapies include those as described herein. Examples of cancers include solid tumors and non-solid tumors, such as liquid tumors, blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, BCL2, CDK4/6, TGF-βR, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., pemigatinib (INCB54828), INCB62079), an EGFR inhibitor (also known as ErB-1 or HER-1; e.g., erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib or niraparib), a JAK inhibitor (JAK1 and/or JAK2; e.g., ruxolitinib or baricitinib; or JAK1; e.g., itacitinib (INCB39110), INCB052793, or INCB054707), an IDO inhibitor (e.g., epacadostat, NLG919, or BMS-986205, MK7162), an LSD1 inhibitor (e.g., GSK2979552, INCB59872 and INCB60003), a TDO inhibitor, a PI3K-delta inhibitor (e.g., parsaclisib (INCB50465) or INCB50797), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer; e.g., INCB081776), an adenosine receptor antagonist (e.g., A2a/A2b receptor antagonist), an HPK1 inhibitor, a chemokine receptor inhibitor (e.g., CCR2 or CCR5 inhibitor), a SHP1/2 phosphatase inhibitor, a histone deacetylase inhibitor (H DAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), c-M ET inhibitors (e.g., capmatinib), an anti-CD19 antibody (e.g., tafasitamab), an ALK2 inhibitor (e.g., INCB00928); or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

In addition, for treating cancer and other proliferative diseases, compounds described herein can be used in combination with targeted therapies such as, e.g., c-MET inhibitors (e.g., capmatinib), an anti-CD19 antibody (e.g., tafasitamab), an ALK2 inhibitor (e.g., INCB00928); or combinations thereof.

Example antibodies for use in combination therapy include, but are not limited to, trastuzumab (e.g., anti-HER2), ranibizumab (e.g., anti-VEGF-A), bevacizumab (AVASTIN™, e.g., anti-VEGF), panitumumab (e.g., anti-EGFR), cetuximab (e.g., anti-EGFR), rituxan (e.g., anti-CD20), and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptosar, topotecan, paclitaxel, docetaxel, epothilones, tamoxifen, 5-fluorouracil, methotrexate, temozolomide, cyclophosphamide, SCH 66336, R115777, L778, 123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, SmI1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, RIG-I agonists, oncolytic virotherapy and immunomodulating small molecules, including thalidomide or JAK1/2 inhibitor, PI3Kδ inhibitor and the like. The compounds can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

Additional examples of chemotherapeutics include proteasome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable CDK4/6 inhibitors include palbociclib, ribociclib, trilaciclib, lerociclib, and abemaciclib, and their pharmaceutically acceptable salts. Other example suitable CDK4/6 inhibitors include compounds, and their pharmaceutically acceptable salts, as disclosed in WO 09/085185, WO 12/129344, WO 11/101409, WO 03/062236, WO 10/075074, and WO 12/061156.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a CDK2 inhibitor of the present disclosure with an additional agent.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, Leishmania, *Staphylococcus aureus, Pseudomonas Aeruginosa*.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, Ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, *Chlamydia*, rickettsial bacteria, mycobacteria, staphylococci, streptococci, pneumococci, meningococci and conococci, *Klebsiella, Proteus, Serratia, Pseudomonas, Legionella*, diphtheria, *Salmonella*, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

When more than one pharmaceutical agent is administered to a patient, they can be administered simultaneously, separately, sequentially, or in combination (e.g., for more than two agents).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

II. Immune-Checkpoint Therapies

Compounds of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD28, CD40, CD70, CD122, CD96, CD73, CD47, CDK2, GITR, CSF1R, JAK, PI3K delta, PI3K gamma, TAM, arginase, HPK1, CD137 (also known as 4-1BB), ICOS, A2AR, B7-H3, B7-H4, BTLA, CTLA-4, LAG3, TIM3, TLR (TLR7/8), TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1 or PD-L1, e.g., an anti-PD-1 or anti-PD-L1 monoclonal antibody. In some embodiments, the anti-PD-1 or anti-PD-L1 antibody is nivolumab, pembrolizumab, atezolizumab, durvalumab, avelumab, cemiplimab, atezolizumab, avelumab, tislelizumab, spartalizumab (PDR001), cetrelimab (JNJ-63723283), toripalimab (JS001), camrelizumab (SHR- 1210), sintilimab (IBI308), AB122 (GLS-010), AMP-224, AMP-514/MEDI-0680, BMS936559, JTX-4014, BGB-108, SHR-1210, MED14736, FAZ053, BCD-100, KN035, CS1001, BAT1306, LZMO09, AK105, HLX10, SHR-1316, CBT-502 (TQB2450), A167 (KL-A167), STI-A101 (ZKAB001), CK-301, BGB-A333, MSB-2311, HLX20, TSR-042, or LY3300054. In some embodiments, the inhibitor of PD-1 or PD-L1 is one disclosed in U.S. Pat. Nos. 7,488,802, 7,943,743, 8,008,449, 8,168,757, 8,217,149, or 10,308,644; U.S. Publ. Nos. 2017/0145025, 2017/0174671, 2017/0174679, 2017/0320875, 2017/0342060, 2017/0362253, 2018/0016260, 2018/0057486, 2018/0177784, 2018/0177870, 2018/0179179, 2018/0179201, 2018/0179202, 2018/0273519, 2019/0040082, 2019/0062345, 2019/0071439, 2019/0127467, 2019/0144439, 2019/0202824, 2019/0225601, 2019/0300524, or 2019/0345170; or PCT Pub. Nos. WO 03042402, WO 2008156712, WO 2010089411, WO 2010036959, WO 2011066342, WO 2011159877, WO 2011082400, or WO 2011161699, which are each incorporated herein by reference in their entirety. In some embodiments, the inhibitor of PD-L1 is INCB086550.

In some embodiments, the antibody is an anti-PD-1 antibody, e.g., an anti-PD-1 monoclonal antibody. In some embodiments, the anti-PD-1 antibody is nivolumab, pembrolizumab, cemiplimab, spartalizumab, camrelizumab, cetrelimab, toripalimab, sintilimab, AB122, AMP-224, JTX-4014, BGB-108, BCD-100, BAT1306, LZMO09, AK105, HLX10, or TSR-042. In some embodiments, the anti-PD-1 antibody is nivolumab, pembrolizumab, cemiplimab, spartalizumab, camrelizumab, cetrelimab, toripalimab, or sintilimab. In some embodiments, the anti-PD-1 antibody is pembrolizumab. In some embodiments, the anti-PD-1 antibody is nivolumab. In some embodiments, the anti-PD-1 antibody is cemiplimab. In some embodiments, the anti-PD-1 antibody is spartalizumab. In some embodiments, the anti-PD-1 antibody is camrelizumab. In some embodiments, the anti-PD-1 antibody is cetrelimab. In some embodiments, the anti-PD-1 antibody is toripalimab. In some embodiments, the anti-PD-1 antibody is sintilimab. In some embodiments, the anti-PD-1 antibody is AB122. In some embodiments, the anti-PD-1 antibody is AMP-224. In some embodiments, the anti-PD-1 antibody is JTX-4014. In some embodiments, the anti-PD-1 antibody is BGB-108. In some embodiments, the anti-PD-1 antibody is BCD-100. In some embodiments, the anti-PD-1 antibody is BAT1306. In some embodiments, the anti-PD-1 antibody is LZMO09. In some embodiments, the anti-PD-1 antibody is AK105. In some embodiments, the anti-PD-1 antibody is HLX10. In some embodiments, the anti-PD-1 antibody is TSR-042. In some embodiments, the anti-PD-1 monoclonal antibody is nivolumab or pembrolizumab. In some embodiments, the anti-PD-1 monoclonal antibody is MGA012 (INCMGA0012; retifanlimab). In some embodiments, the anti-PD1 antibody is SHR-1210. Other anti-cancer agent(s) include antibody therapeutics such as 4-1BB (e.g., urelumab, utomilumab). In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, avelumab, durvalumab, tislelizumab, BMS-935559, MEDI4736, atezolizumab (MPDL3280A; also known as RG7446), avelumab (MSB0010718C), FAZ053, KN035, CS1001, SHR-1316, CBT-502, A167, STI-A101, CK-301, BGB-A333, MSB-2311, HLX20, or LY3300054. In some embodiments, the anti-PD-L1 antibody is atezolizumab, avelumab, durvalumab, or tislelizumab. In some embodiments, the anti-PD-L1 antibody is atezolizumab. In some embodiments, the anti-PD-L1 antibody is avelumab. In some embodiments, the anti-PD-L1 antibody is durvalumab. In some embodiments, the anti-PD-L1 antibody is tislelizumab. In some embodiments, the anti-PD-L1 antibody is BMS-935559. In some embodiments, the anti-PD-L1 antibody is MEDI4736. In some embodiments, the anti-PD-L1 antibody is FAZ053. In some embodiments, the anti-PD-L1 antibody is KN035. In some embodiments, the anti-PD-L1 antibody is CS1001. In some embodiments, the anti-PD-L1 antibody is SHR-1316. In some embodiments, the anti-PD-L1 antibody is CBT-502. In some embodiments, the anti-PD-L1 antibody is A167. In some embodiments, the anti-PD-L1 antibody is STI-A101. In some embodiments, the anti-PD-L1 antibody is CK-301. In some embodiments, the anti-PD-L1 antibody is BGB-A333. In some embodiments, the anti-PD-L1 antibody is MSB-2311. In some embodiments, the anti-PD-L1 antibody is HLX20. In some embodiments, the anti-PD-L1 antibody is LY3300054.

In some embodiments, the inhibitor of an immune checkpoint molecule is a small molecule that binds to PD-L1, or a pharmaceutically acceptable salt thereof. In some embodiments, the inhibitor of an immune checkpoint molecule is a small molecule that binds to and internalizes PD-L1, or a pharmaceutically acceptable salt thereof. In some embodiments, the inhibitor of an immune checkpoint molecule is a compound selected from those in US 2018/0179201, US 2018/0179197, US 2018/0179179, US 2018/0179202, US 2018/0177784, US 2018/0177870, U.S. Ser. No. 16/369,654 (filed Mar. 29, 2019), and U.S. Ser. No. 62/688,164, or a pharmaceutically acceptable salt thereof, each of which is incorporated herein by reference in its entirety.

In some embodiments, the inhibitor of an immune checkpoint molecule is an inhibitor of KIR, TIGIT, LAIR1, CD160, 2B4 and TGFR beta.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD73. In some embodiments, the inhibitor of CD73 is MED19447.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of CD137 is urelumab. In some embodiments, the agonist of CD137 is utomilumab.

In some embodiments, the agonist of an immune checkpoint molecule is an inhibitor of GITR. In some embodiments, the agonist of GITR is TRX518, MK-4166, INCAGN1876, MK-1248, AMG228, BMS-986156, GWN323, MED11873, or MED16469. In some embodiments, the agonist of an immune checkpoint molecule is an agonist of OX40, e.g., OX40 agonist antibody or OX40L fusion protein. In some embodiments, the anti-OX40 antibody is INCAGN01949, MEDI0562 (tavolimab), MOXR-0916, PF-04518600, GSK3174998, BMS-986178, or 9B12. In some embodiments, the OX40L fusion protein is MEDI6383.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196. Inhibitors of arginase inhibitors include INCB1158.

As provided throughout, the additional compounds, inhibitors, agents, etc. can be combined with the present compound in a single or continuous dosage form, or they can be administered simultaneously or sequentially as separate dosage forms.

Formulation, Dosage Forms and Administration

When employed as pharmaceuticals, the compounds of the present disclosure can be administered in the form of pharmaceutical compositions. Thus, the present disclosure provides a composition comprising a compound of Formula I, II, or any of the formulas as described herein, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

Another aspect of the present invention relates to labeled compounds of the disclosure (radio-labeled, fluorescent-labeled, etc.) that would be useful not only in imaging techniques but also in assays, both in vitro and in vivo, for localizing and quantitating KRAS protein in tissue samples, including human, and for identifying KRAS ligands by inhibition binding of a labeled compound. Substitution of one or more of the atoms of the compounds of the present disclosure can also be useful in generating differentiated ADM E (Adsorption, Distribution, Metabolism and Excretion). Accordingly, the present invention includes KRAS binding assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula I, II, or any formulae provided herein can be optionally substituted with deuterium atoms, such as —$CD_3$ being substituted for —$CH_3$). In some embodiments, alkyl groups in Formula I, II, or any formulae provided herein can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radiolabeled compounds will depend on the specific application of that radio-labeled compound. For example, for in vitro adenosine receptor labeling and competition assays, compounds that incorporate $^3H$, $^{14}C$, $^{82}Br$, $^{125}I$, $^{131}I$ or $^{35}S$ can be useful. For radio-imaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments, the radionuclide is selected from $^3H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the invention can be used in a screening assay to identify and/or evaluate compounds. For example, a newly synthesized or identified compound (i.e., test compound) which is labeled can be evaluated for its ability to bind a KRAS protein by monitoring its concentration variation when contacting with the KRAS, through tracking of the labeling. For example, a test compound (labeled) can be evaluated for its ability to reduce binding of another compound which is known to bind to a KRAS protein (i.e., standard compound). Accordingly, the ability of a test compound to compete with the standard compound for binding to the KRAS protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, e.g., in the treatment or prevention of diseases or disorders associated with the activity of KRAS, such as cancer or infections, which include one or more containers containing a pharmaceutical composition comprising a therapeutically effective amount of a compound of Formula I, II, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of KRAS according to at least one assay described herein.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check.

The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 µm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K.

Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 µm particle size, 19×100 mm column, eluting with mobile phase A: 0.15% $NH_4OH$ in water and mobile phase B: acetonitrile; the flow rate was 30 ml/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute."

The following abbreviations may be used herein: AcOH (acetic acid); $Ac_2O$ (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N, N'-diisopropyl azidodicarboxylate); DIEA (N,N-diisopropylethylamine); DIBAL-H (diisobutylaluminium hydride); DMF (N, N-dimethylformamide); EtOH (ethanol); EtOAc (ethyl acetate); FCC (flash column chromatography); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography—mass spectrometry); LDA (lithium diisopropylamide); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); mmol (millimole(s)); N (normal); NCS (N-chlorosuccinimide); $NEt_3$ (triethylamine); nM (nanomolar); NMP (N-methylpyrrolidinone); NMR (nuclear magnetic resonance spectroscopy); OTf (trifluoromethanesulfonate); Ph (phenyl); pM (picomolar); PPT (precipitate); RP-HPLC (reverse phase high performance liquid chromatography); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); µg (microgram(s)); µL (microliter(s)); µM (micromolar); wt % (weight percent). Brine is saturated aqueous sodium chloride. In vacuo is under vacuum.

The compounds of the present disclosure can be isolated in free-base or pharmaceutical salt form. In the examples provided herein, the compounds are isolated as the corresponding TFA salt.

Intermediate 1. 2-(3-(methoxymethoxy)naphthalen-1-yl)-4,4,5,5-tetramethyl-1,3,2-dioxaborolane

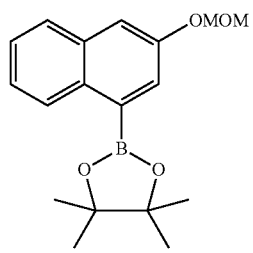

To a solution of 4-(4,4,5,5-tetramethyl-1,3,2-dioxaborolan-2-yl)naphthalen-2-ol (10 g, 37.0 mmol) in DCM (123 ml) at 0° C. were added Hunig's base (32.3 ml, 185 mmol) and MOM-Cl (8.44 ml, 111 mmol). After stirring at r.t. for 1 hr, the reaction was quenched with water and extracted with DCM. The organic layer was washed with brine, dried over sodium sulfate and concentrated. The crude product was purified by Biotage Isolera™ (0-20% ethyl acetate in hexanes) to provide the desired product as a white solid (7.9 g, 68%). LC-MS calculated for $C_{18}H_{24}BO_4$ $(M+H)^+$: m/z=315.2; found 315.2.

Intermediate 2. tert-butyl 8-(3-chloro-5-fluoro-6-(3-(methoxymethoxy)naphthalen-1-yl)isoquinolin-1-yl)-3,8-diazabicyclo[3.2.1]octane-3-carboxylate

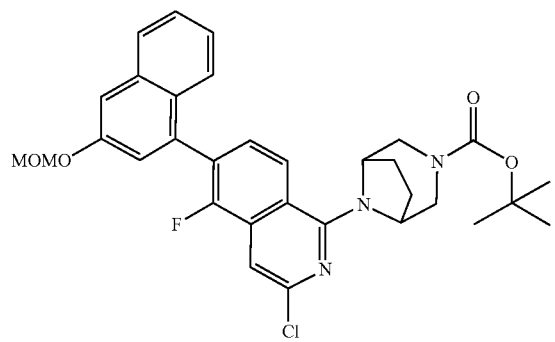

Step 1. 4-bromo-2-(carboxymethyl)-3-fluorobenzoic acid

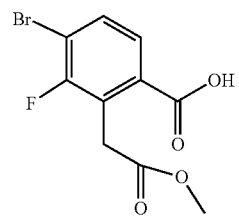 [SMILES: COC(=O)Cc1c(C(=O)O)ccc(Br)c1F]

To a solution of 4-bromo-3-fluoro-2-methylbenzoic acid (5 g, 21.46 mmol) and dimethyl carbonate (3.62 ml, 42.9 mmol) in THF (107 ml) at −78° C. was added LDA (2.0 M in THF/heptane/ethylbenzene), 42.9 ml, 86 mmol) dropwise and the reaction mixture was allowed to warm to r.t., then stirred for 4 hr. The reaction was quenched with 1 N HCl, then extracted with ethyl acetate. The organic layer was washed with water and brine, dried over sodium sulfate and concentrated. The crude product was used in the next step without further purification (5.9 g, 94%). LC-MS calculated for $C_9H_7BrFO_4$ $(M+H)^+$: m/z=277.0/279.0; found 277.0/279.0.

Step 2.
6-bromo-5-fluoroisoquinoline-1,3(2H,4H)-dione

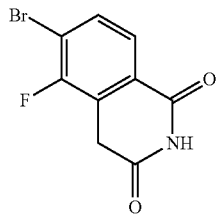

4-bromo-3-fluoro-2-(2-methoxy-2-oxoethyl)benzoic acid (5.9 g, 20.27 mmol) was suspended in ammonium hydroxide (7.89 ml, 203 mmol), then concentrated. This was repeated one more time, then o-dichlorobenzene (40.5 ml) was added and the reaction mixture was heated to 200° C. for 2 hr. The mixture was cooled, then diluted with hexanes. The resulting solid was collected by filtration, then washed with hexanes and air dried. The crude product was used in the next step without further purification (2.36 g, 45%). LC-MS calculated for $C_9H_6BrFNO_2$ (M+H)$^+$: m/z=258.0/260.0; found 258.0/260.0.

Step 3. 6-bromo-1,3-dichloro-5-fluoroisoquinoline

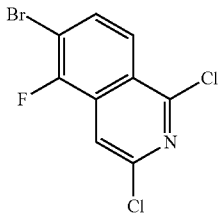 [SMILES: Fc1c(Br)ccc2c(Cl)nc(Cl)cc12]

6-bromo-5-fluoroisoquinoline-1,3(2H,4H)-dione (2.36 g, 9.15 mmol) in neat diphenyl chlorophosphate (4.74 ml, 22.86 mmol) was heated to 165° C. for 4 hr, then the solid was broken up and suspended in water. Sat. ammonium hydroxide (15 mL) was added and the mixture was stirred for 30 mins at r.t., then filtered. The solid was washed liberally with water, air dried and used in the next step without further purification (2.17 g, 80%). LC-MS calculated for $C_9H_4BrCl_2FN$ (M+H)$^+$: m/z=293.9/295.9/297.9; found 294.0/296.0/298.0.

Step 4. tert-butyl 8-(6-bromo-3-chloro-5-fluoroisoquinolin-1-yl)-3,8-diazabicyclo[3.2.1]octane-3-carboxylate

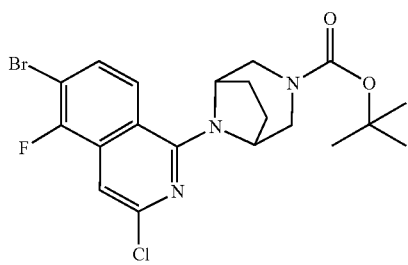 [SMILES: CC(C)(C)OC(=O)N1CC2CCC(C1)N2c1nc(Cl)cc2c(F)c(Br)ccc12]

To a solution of 6-bromo-1,3-dichloro-5-fluoroisoquinoline (2.17 g, 7.36 mmol) in DMA (18.39 ml) were added tert-butyl 3,8-diazabicyclo[3.2.1]octane-3-carboxylate (1.718 g, 8.09 mmol) and Hunig's base (1.542 ml, 8.83 mmol) and the reaction mixture was stirred at 100° C. overnight. The reaction was quenched with water and extracted with DCM. The organic layer was washed with water and brine, dried over sodium sulfate and concentrated. The crude solid was used in the next step without further purification (2.65 g, 77%). LC-MS calculated for $C_{20}H_{23}BrClFN_3O_2$ (M+H)$^+$: m/z=470.1/472.2; found 414.0/416.0 (M−tBu)$^+$.

Step 5. tert-butyl 8-(3-chloro-5-fluoro-6-(3-(methoxymethoxy)naphthalen-1-yl)isoquinolin-1-yl)-3,8-diazabicyclo[3.2.1]octane-3-carboxylate

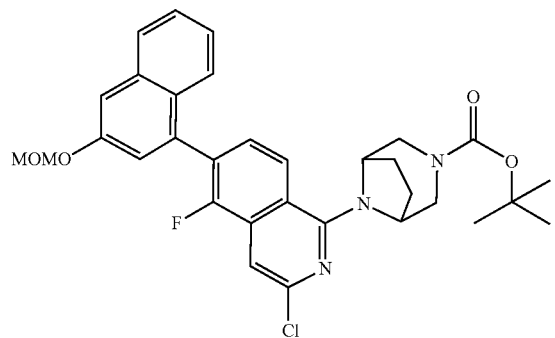

To a mixture of tert-butyl 8-(6-bromo-3-chloro-5-fluoroisoquinolin-1-yl)-3,8-diazabicyclo[3.2.1]octane-3-carboxylate (1.0 g, 2.124 mmol), Intermediate 1 (0.734 g, 2.337 mmol), tetrakis(triphenylphosphine)palladium(0) (0.245 g, 0.212 mmol) and sodium carbonate (0.675 g, 6.37 mmol) were added Dioxane (6.80 ml)/Water (1.7 ml) and the reaction flask was evacuated, back filed with nitrogen, then stirred at 80° C. overnight. The mixture was diluted with DCM and filtered through a plug of Celite. The filtrate was concentrated and the crude residue was purified by Biotage Isolera™ (10-50% ethyl acetate in hexanes) to provide the desired product as a white solid (1.09 g, 89%). LC-MS calculated for $C_{32}H_{34}ClFN_3O_4$ (M+H)$^+$: m/z=578.2; found 522.2 (M−tBu)$^+$.

Intermediate 3. 3-(1-(3,8-diazabicyclo[3.2.1]octan-8-yl)-3-chloro-5-fluoro-6-(3-hydroxynaphthalen-1-yl)isoquinolin-7-yl)propanenitrile

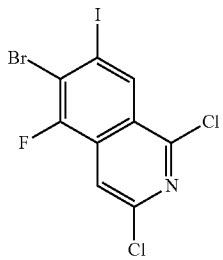 [SMILES: Fc1c(Br)c(I)cc2c(Cl)nc(Cl)cc12]

Step 1. methyl 4-bromo-2,3-difluorobenzoate

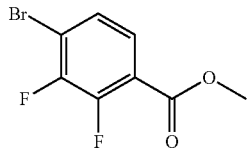

To a solution of 4-bromo-2,3-difluorobenzoic acid (50.7 g, 214 mmol) in acetone (428 ml) was added potassium carbonate (35.5 g, 257 mmol) and dimethyl sulfate (20.44 ml, 214 mmol) and the reaction mixture was heated to 80° C. for 4 hr, then quenched with water and extracted with ethyl acetate. The organic layer was washed with water and brine, dried over sodium sulfate and concentrated. The crude solid was used in the next step without further purification. LC-MS calculated for $C_8H_6BrF_2O_2$ (M+H)$^+$: m/z=250.9/252.9; found 251.0/252.0.

Step 2. methyl 4-bromo-2,3-difluoro-5-iodobenzoate

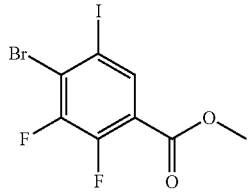

To a 0° C. solution of methyl 4-bromo-2,3-difluorobenzoate (53 g, 211 mmol) in DCM (264 ml) was added $H_2SO_4$ (264 ml) dropwise followed by NIS (71.3 g, 317 mmol) portionwise. The reaction mixture was warmed to r.t. and stirred for 2 hr, then quenched by slowly pouring into ice and extracted with ethyl acetate. The organic layer was washed with sat. sodium bicarbonate, sat. sodium thiosulfate, water and brine, dried over sodium sulfate and concentrated. The crude solid was sufficiently pure to use in the next step (74.7 g, 94% over 2 steps). LC-MS calculated for $C_8H_5BrF_2IO_2$ (M+H)$^+$: m/z=376.8/378.8; found 376.9/378.9.

Step 3. dimethyl 2-(3-bromo-2-fluoro-4-iodo-6-(methoxycarbonyl)phenyl)malonate

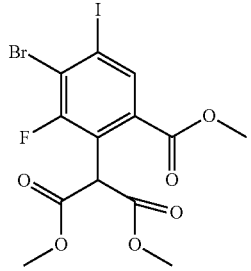

To a solution of dimethyl malonate (23.87 ml, 208 mmol) in THF (400 mL) at 0° C. was added sodium hydride (60% in mineral oil, 8.31 g, 208 mmol) in one portion and the reaction mixture was allowed to stir at 0° C. for 10 mins, then a solution of methyl 4-bromo-2,3-difluoro-5-iodobenzoate (37.3 g, 99 mmol) in THF (150 mL) was added dropwise and the reaction mixture was warmed to reflux overnight. After cooling to r.t., the reaction was quenched with 1N HCl and extracted with ethyl acetate. The organic layer was washed with water and brine, dried over sodium sulfate and concentrated. When most of the solvent had evaporated, the flask was removed from the rotovap and hexanes (4-5V relative to expected product) was added and the mixture was stirred vigorously for 15 mins, then filtered. The solid was washed with hexanes and air dried, then used in the next step without further purification (34.4 g, 71%). LC-MS calculated for $C_{13}H_{12}BrFIO_6$ (M+H)$^+$: m/z=488.9/490.9; found 489.0/491.0.

Step 4. 4-bromo-2-(carboxymethyl)-3-fluoro-5-iodobenzoic acid

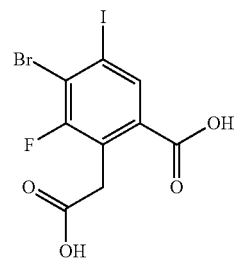 [SMILES: O=C(O)Cc1c(C(=O)O)cc(I)c(Br)c1F]

Dimethyl 2-(3-bromo-2-fluoro-4-iodo-6-(methoxycarbonyl)phenyl)malonate (34.4 g, 70.3 mmol) was dissolved in a 1:1:2 mixture of THF/MeOH/4N NaOH (60 mL) and heated of 80° C. for 4 hr. The reaction was then acidified with 12 N HCl, diluted with water then extracted with ethyl acetate. The organic layer was washed with water and brine, dried over sodium sulfate and concentrated. The crude solid was triturated with DCM to provide the desired product (24 g, 85%). LC-MS calculated for $C_9H_6BrFIO_4$ (M+H)$^+$: m/z=402.8/404.8; found 402.9/404.9.

Step 5. 6-bromo-5-fluoro-7-iodoisoquinoline-1,3(2H,4H)-dione

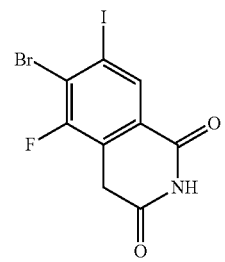 [SMILES: O=C1Cc2c(cc(I)c(Br)c2F)C(=O)N1]

A suspension of 4-bromo-2-(carboxymethyl)-3-fluoro-5-iodobenzoic acid (24 g, 59.6 mmol) in Acetyl chloride (100 ml) was heated to 65° C. for 1 hr, then cooled to r.t. Hexanes (~100 mL) was added and the mixture was filtered. The solid was washed with hexanes, then briefly air dried. The crude solid was suspended in water (100 mL) and cooled to 0° C. Ammonium hydroxide (9 ml, 69.3 mmol) was added dropwise and the reaction mixture was stirred at r.t. for 1 hr, then re-cooled to 0° C. HCl (5.96 ml, 71.5 mmol) was added dropwise, then the mixture was diluted with 1N HCl and filtered. The crude solid was washed with water and air dried overnight. A suspension of the resulting solid in o-dichlorobenzene (83 ml) was heated to 200° C. and stirred at this temperature for 1 hr. After cooling, hexanes was added and the resulting suspension was stirred vigorously for 30 mins, then filtered. The solid was washed with hexanes, then air dried. The crude solid was used in the next step without further purification. (17.6 g, 77%). LC-MS calculated for $C_9H_5BrFINO_2$ (M+H)$^+$: m/z=383.8/385.8; found 383.9/385.9.

Step 6.
6-bromo-1,3-dichloro-5-fluoro-7-iodoisoquinoline

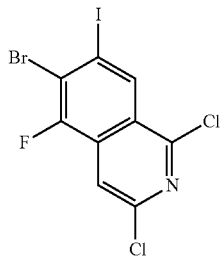

6-bromo-5-fluoro-7-iodoisoquinoline-1,3(2H,4H)-dione (17.6 g, 45.8 mmol) in neat phenylphosphonic dichloride (16.25 ml, 115 mmol) was heated to 165° C. for 1 hr, then cooled to r.t. and quenched with the slow addition of water. The solid was broken up and allowed to stir in water for 30 mins, then ammonium hydroxide was added to basify the mixture and stirring was continued for an additional 30 mins. The solid was collected by filtration and washed liberally with water. The solid was then taken up in 9:1 DCM/MeOH (200 mL), then washed with water and brine, dried over sodium sulfate and concentrated. The resulting solid was triturated with ether to provide the desired product (13.4 g, 70%). LC-MS calculated for $C_9H_5BrFINO_2$ (M+H)$^+$: m/z=419.8/421.8/423.8; found 419.9/421.9/423.9.

Intermediate 4. tert-butyl 8-(3-chloro-7-(2-cyanoethyl)-5-fluoro-6-(3-(methoxymethoxy)naphthalen-1-yl)isoquinolin-1-yl)-3,8-diazabicyclo[3.2.1]octane-3-carboxylate

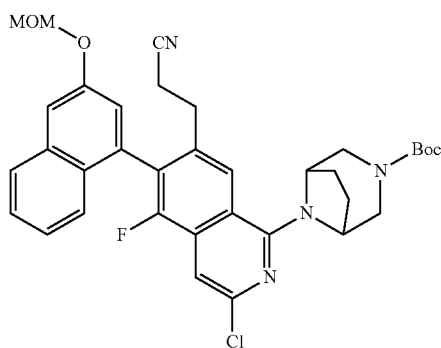

Step 1. tert-butyl 8-(6-bromo-3-chloro-5-fluoro-7-iodoisoquinolin-1-yl)-3,8-diazabicyclo[3.2.1]octane-3-carboxylate

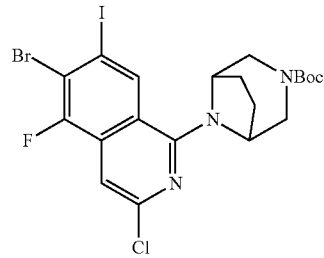 [SMILES: CC(C)(C)OC(=O)N1CC2CCC(C1)N2c1nc(Cl)cc2c(F)c(Br)c(I)cc12]

To a solution of 6-bromo-1,3-dichloro-5-fluoro-7-iodoisoquinoline (Intermediate 3, 3 g, 7.13 mmol) in DMA (14.26 ml) were added tert-butyl 3,8-diazabicyclo[3.2.1]octane-3-carboxylate (1.66 g, 7.84 mmol) and Hunig's base (1.494 ml, 8.55 mmol) and the reaction mixture was heated to 100° C. for 2 hr, then quenched with water. To the crude solid was added a 3:1 mixture of hexanes/ethyl acetate (30 mL). After stirring at r.t. for 15 mins, the mixture was filtered and the solid was washed with ether (2.8 g, 66%). LC-MS calculated for $C_{20}H_{22}BrClFIN_3O_2$ (M+H)$^+$: m/z=596.0/598.0; found 540.0/542.0 (M−tBu)$^+$.

Step 2. tert-butyl 8-(6-bromo-3-chloro-7-(2-cyanoethyl)-5-fluoroisoquinolin-1-yl)-3,8-diazabicyclo[3.2.1]octane-3-carboxylate

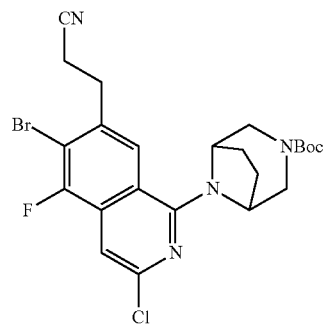 [SMILES: CC(C)(C)OC(=O)N1CC2CCC(C1)N2c1nc(Cl)cc2c(F)c(Br)c(CCC#N)cc12]

To a solution of tert-butyl 8-(6-bromo-3-chloro-5-fluoro-7-iodoisoquinolin-1-yl)-3,8-diazabicyclo[3.2.1]octane-3-carboxylate (2.75 g, 4.61 mmol) in DMF (15.36 ml) were added triethylamine (1.285 ml, 9.22 mmol), acrylonitrile (2.124 ml, 32.3 mmol), Tetramethylammonium formate (3.66 ml, 9.22 mmol) and tetrakis(triphenylphosphine) palladium(0) (0.533 g, 0.461 mmol). The reaction flask was evacuated, back filled with nitrogen, then stirred at 70° C. overnight. The reaction flask was then cooled down to r.t. and quenched with water. The resulting precipitate was collected by filtration and washed with water. The solid was then further purified by Biotage Isolera™ (0-2% MeOH in dichloromethane) to provide the desired product (1.79 g, 74%). LC-MS calculated for $C_{23}H_{26}BrClFN_4O_2$ (M+H)$^+$: m/z=523.1/525.1; found 467.1/469.1 (M−tBu)$^+$.

Step 3. tert-butyl 8-(3-chloro-7-(2-cyanoethyl)-5-fluoro-6-(3-(methoxymethoxy)naphthalen-1-yl)isoquinolin-1-yl)-3,8-diazabicyclo[3.2.1]octane-3-carboxylate To a mixture of tert-butyl 8-(6-bromo-3-chloro-7-(2-cyanoethyl)-5-fluoroisoquinolin-1-yl)-3,8-diazabicyclo[3.2.1]octane-3-carboxylate (1.49 g, 2.84 mmol), Intermediate 1 (0.894 g, 2.84 mmol), sodium carbonate (0.904 g, 8.53 mmol) and tetrakis(triphenylphosphine)palladium(0) (0.329 g, 0.284 mmol) were added dioxane (7.6 ml) and Water (1.9 ml) and the reaction flask was evacuated, back filled with nitrogen, then stirred at 80° C. for overnight. The reaction was diluted with DCM and filtered through a plug of Celite. The filtrate was concentrated and the residue was purified by Biotage Isolera™ (0-60% ethyl acetate in hexanes) to provide the desired product (1.5 g, 84%). LC-MS calculated for $C_{35}H_{37}ClFN_4O_4$ $(M+H)^+$: m/z=631.2; found 575.2 $(M-tBu)^+$.

Intermediate 5. 3-(3-chloro-5-fluoro-6-(3-(methoxymethoxy)naphthalen-1-yl)-1-(methylsulfonyl)isoquinolin-7-yl)propanenitrile

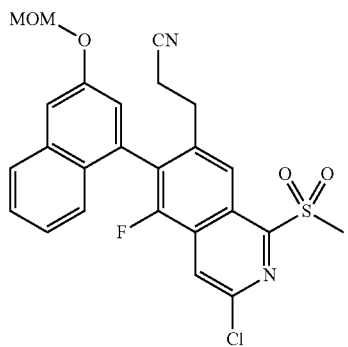

Step 1. 6-bromo-3-chloro-5-fluoro-7-iodo-1-(methylthio)isoquinoline

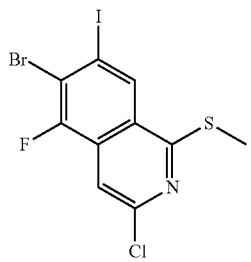 [SMILES: CSc1nc(Cl)cc2c(F)c(Br)c(I)cc12]

To a suspension of 6-bromo-1,3-dichloro-5-fluoro-7-iodoisoquinoline (4.34 g, 10.31 mmol) in MeOH (41.3 ml), was added sodium thiomethoxide (0.723 g, 10.31 mmol) in MeOH and the reaction mixture was stirred at r.t. for 2 hr, then concentrated. The residue was suspended in water, filtered and the solid washed with water and ether, then air dried. The crude solid was used in the next step without further purification (3.57 g, 80%). LC-MS calculated for $C_{10}H_6BrClFINS$ $(M+H)^+$: m/z=431.8/433.8; found 431.8/433.8.

Step 2. 3-(6-bromo-3-chloro-5-fluoro-1-(methylthio)isoquinolin-7-yl)propanenitrile

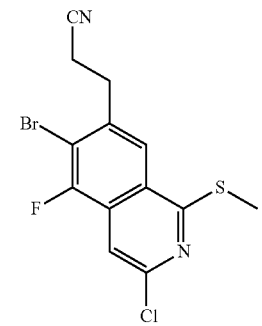

To a mixture of 6-bromo-3-chloro-5-fluoro-7-iodo-1-(methylthio)isoquinoline (3.57 g, 8.25 mmol) and tetrakis(triphenylphosphine)palladium(0) (0.954 g, 0.825 mmol) were added acrylonitrile (3.80 ml, 57.8 mmol), triethylamine (2.301 ml, 16.51 mmol), Tetramethylammonium formate (6.56 ml, 16.51 mmol) and DMF (27.5 ml) and the reaction flask was evacuated, back filled with nitrogen, then stirred at 70° C. overnight. The mixture was quenched with water and extracted with ethyl acetate. The organic layer was washed with water and brine, dried over sodium sulfate and concentrated. The crude product was purified by Biotage (0-30% ethyl acetate in hexanes) to provide the desired product as a yellow solid (1.6 g, 54%). LC-MS calculated for $C_{13}H_{10}BrClFN_2S$ $(M+H)^+$: m/z=358.9/360.9; found 359.0/361.0.

Step 3. 3-(3-chloro-5-fluoro-6-(3-(methoxymethoxy)naphthalen-1-yl)-1-(methylthio)isoquinolin-7-yl)propanenitrile

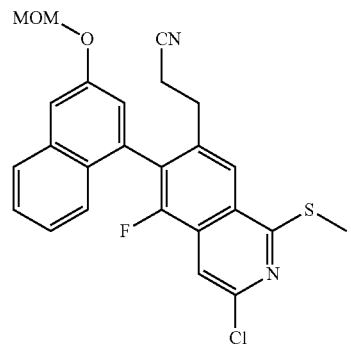

To a mixture of 3-(6-bromo-3-chloro-5-fluoro-1-(methylthio)isoquinolin-7-yl)propanenitrile (1.6 g, 4.45 mmol), Intermediate 1 (1.538 g, 4.89 mmol), tetrakis(triphenylphosphine)palladium(0) (0.514 g, 0.445 mmol) and sodium carbonate (1.415 g, 13.35 mmol) were added dioxane (12 ml)/water (3 ml) and the reaction flask was evacuated, back filled with nitrogen, then stirred at 80° C. overnight. The mixture was diluted with DCM and filtered through a plug of Celite. The filtrate was concentrated and the crude product was purified by Biotage Isolera™ (0-2% methanol in dichloromethane) to provide the desired product (1.15 g, 55%). LC-MS calculated for $C_{25}H_{21}ClFN_2O_2S$ (M+H)$^+$: m/z=467.1; found 467.2.

Step 4. 3-(3-chloro-5-fluoro-6-(3-(methoxymethoxy)naphthalen-1-yl)-1-(methylsulfonyl)isoquinolin-7-yl)propanenitrile To a solution of 3-(3-chloro-5-fluoro-6-(3-(methoxymethoxy)naphthalen-1-yl)-1-(methylthio)isoquinolin-7-yl)propanenitrile (2 g, 4.28 mmol) in DCM (21.42 ml) was added m-CPBA (1.920 g, 8.57 mmol) and the reaction mixture was stirred at r.t. for 1 hr, then quenched with sat. sodium bicarbonate and sat. sodium thiosulfate. The mixture was diluted with water and extracted with DCM. The organic layer was washed with brine, dried over sodium sulfate and concentrated. The crude product was purified by Biotage (10-70% ethyl acetate in hexanes) to provide the desired product as a white solid (2.13 g, 100%). LC-MS calculated for $C_{25}H_{21}ClFN_2O_4S$ (M+H)$^+$: m/z=499.1; found 499.2.

Intermediate 6. 4-bromo-3-chloro-7-(2-cyanoethyl)-5-fluoro-6-(3-(methoxymethoxy)naphthalen-1-yl)isoquinolin-1-yl trifluoromethanesulfonate

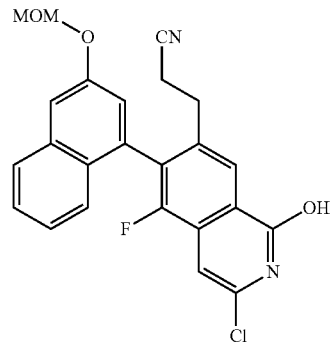

Step 1. 3-(3-chloro-5-fluoro-1-hydroxy-6-(3-(methoxymethoxy)naphthalen-1-yl)isoquinolin-7-yl)propanenitrile

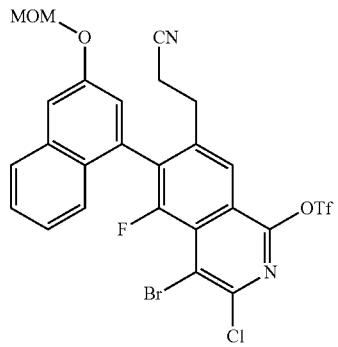

To a solution of Intermediate 5 (800 mg, 1.603 mmol) in dioxane (6.41 ml) was added cesium carbonate (522 mg, 1.603 mmol) and the reaction mixture was heated to 100° C. overnight, then quenched with water and extracted with 9:1 DCM/MeOH. The organic layer was washed with water and brine, dried over sodium sulfate and concentrated. The crude product was purified by Biotage Isolera™ (1-4% MeOH in DCM) to provide the desired product (562 mg, 80%). LC-MS calculated for $C_{24}H_{19}ClFN_2O_3$ (M+H)$^+$: m/z=437.1; found 437.2.

Step 2. 3-(4-bromo-3-chloro-5-fluoro-1-hydroxy-6-(3-(methoxymethoxy)naphthalen-1-yl)isoquinolin-7-yl)propanenitrile

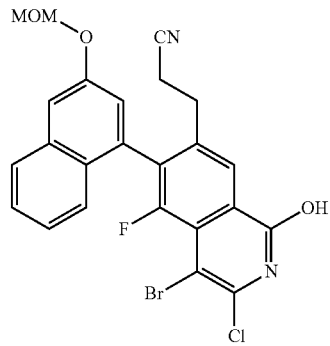

To a solution of 3-(3-chloro-5-fluoro-1-hydroxy-6-(3-(methoxymethoxy)naphthalen-1-yl)isoquinolin-7-yl)propanenitrile (1.25 g, 2.86 mmol) in DMF (14.31 ml) was added NBS (0.509 g, 2.86 mmol) and the reaction mixture was stirred at r.t. for 30 mins, then quenched with water and extracted with DCM. The organic layer was washed with water and brine, dried over sodium sulfate and concentrated. The crude product was purified by Biotage Isolera™ (20-100% ethyl acetate in hexanes) to provide the desired product as an off white solid (1.3 g, 88%). LC-MS calculated for $C_{24}H_{18}BrClFN_2O_3$ (M+H)$^+$: m/z=515.0/517.0; found 515.0/517.0.

Step 3. 4-bromo-3-chloro-7-(2-cyanoethyl)-5-fluoro-6-(3-(methoxymethoxy)naphthalen-1-yl)isoquinolin-1-yl trifluoromethanesulfonate To a solution of 3-(4-bromo-3-chloro-5-fluoro-1-hydroxy-6-(3-(methoxymethoxy)naphthalen-1-yl)isoquinolin-7-yl)propanenitrile (550 mg, 1.066 mmol) in DCM (5.33 ml) was added Hunig's base (224 µL, 1.28 mmol) and the reaction mixture was cooled to −78° C. Triflic anhydride (200 µL, 1.17 mmol) was added dropwise. After 5 mins at −78° C., the reaction mixture was transferred to a 0° C. bath and stirred at this temperature for 30 mins. The reaction was quenched with water and extracted with DCM. The organic layer was washed brine, dried over sodium sulfate and concentrated. The crude product was used in the next step without further purification (690 mg, 100%). LC-MS calculated for $C_{25}H_{17}BrClF_4N_2O_5S$ (M+H)$^+$: m/z=647.0/649.0; found 647.0/649.0.

Intermediate 7. 1,3,6-trichloro-5-fluoro-2,7-naphthyridine-4-carbonitrile

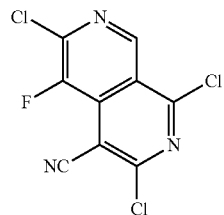 [SMILES: N#Cc1c(Cl)nc(Cl)c2cnc(Cl)c(F)c12]

Step 1. 6-(benzyloxy)-4-chloro-5-fluoronicotinic acid

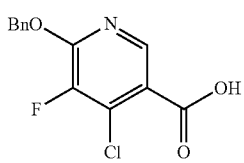 [SMILES: O=C(O)c1cnc(OCc2ccccc2)c(F)c1Cl]

To a solution of benzyl alcohol (2.149 ml, 20.67 mmol) in THF (50 ml) was added sodium hydride (0.909 g, 22.74 mmol, 60% in mineral oil) and the reaction mixture was stirred at r.t. for 10 mins, then cooled to 0° C. 4-chloro-5,6-difluoronicotinic acid (2.0 g, 10.33 mmol) was added and the reaction mixture was stirred at r.t. for 30 mins, then cooled to 0° C. and quenched with water. The mixture was then washed with ethyl acetate and the organic layer was discarded. The aqueous layer was acidified with 1N HCl, then extracted with DCM. The organic layer was dried over sodium sulfate and concentrated. The crude product was used in the next step without further purification (2.8 g, 96%). LCMS calculated for $C_{13}H_{10}ClFNO_3$ $(M+H)^+$: m/z=282.0/284.0, Found: 282.0/284.0.

Step 2. 6-(benzyloxy)-4-chloro-5-fluoronicotinamide

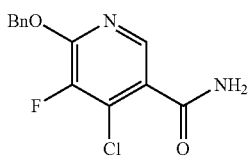 [SMILES: NC(=O)c1cnc(OCc2ccccc2)c(F)c1Cl]

To a solution of 6-(benzyloxy)-4-chloro-5-fluoronicotinic acid (2.8 g, 9.94 mmol), HATU (4.16 g, 10.93 mmol) and ammonium chloride (0.798 g, 14.91 mmol) in DMF (49.7 ml) was added Hunig's base (5.21 ml, 29.8 mmol) and the reaction mixture was stirred at r.t. for 30 mins, then cooled to 0° C. and quenched with ice water. The resulting precipitate was collected by filtration, washed with water and air dried, then used in the next step without further purification (2.5 g, 91%). LCMS calculated for $C_{13}H_{11}ClFN_2O_2$ $(M+H)^+$: m/z=281.0/283.0, Found: 281.0/283.0.

Step 3. 6-(benzyloxy)-5-fluoro-1,3-dioxo-1,2,3,4-tetrahydro-2,7-naphthyridine-4-carbonitrile

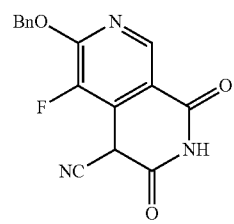 [SMILES: N#CC1C(=O)NC(=O)c2cnc(OCc3ccccc3)c(F)c21]

To a solution of tert-butyl cyanoacetate (1067 µl, 7.48 mmol) in THF (10 ml) was added sodium hydride (299 mg, 7.48 mmol, 60% in mineral oil) and the mixture was stirred at r.t. for 10 mins, then 6-(benzyloxy)-4-chloro-5-fluoronicotinamide (700 mg, 2.494 mmol) was added in one portion and the mixture was stirred at 80° C. overnight. The mixture was cooled to 0° C. and quenched with acetic acid (428 µl, 7.48 mmol). The mixture is then concentrated. The residue was taken up in ether and stirred for 10 mins, then filtered. The resulting solid was used in the next step without further purification. LCMS calculated for $C_{16}H_{11}FN_3O_3$ $(M+H)^+$: m/z=312.1, Found: 312.1.

Step 4. 1,3,6-trichloro-5-fluoro-2,7-naphthyridine-4-carbonitrile

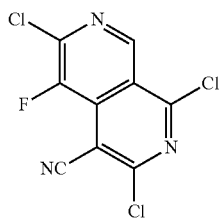 [SMILES: N#Cc1c(Cl)nc(Cl)c2cnc(Cl)c(F)c12]

6-(benzyloxy)-5-fluoro-1,3-dioxo-1,2,3,4-tetrahydro-2,7-naphthyridine-4-carbonitrile (360 mg, 1.157 mmol) was suspended in $POCl_3$ (2156 µl, 23.13 mmol) and Hunig's base (404 µl, 2.313 mmol) was added. The mixture was then heated to 100° C. overnight to give cleanly the trichloride. The mixture was then added into ice slowly and the resulting biphasic mixture allowed to stir until the dark solution at the bottom turned into a solid. This solid was collected by filtration, washed with water, then redissolved in DCM. The solution was washed with sat. sodium bicarbonate, water and brine, dried over sodium sulfate and concentrated. The resulting solid was sufficiently pure to be used in the next step (205 mg, 64%). LCMS calculated for $C_9H_2Cl_3FN_3$ $(M+H)^+$: m/z=275.9/277.9, Found: 275.9/277.9.

Example 1. 1-(3,8-diazabicyclo[3.2.1]octan-8-yl)-3-(3-(dimethylamino)azetidin-1-yl)-5-fluoro-6-(3-hydroxynaphthalen-1-yl)isoquinoline-4-carbonitrile

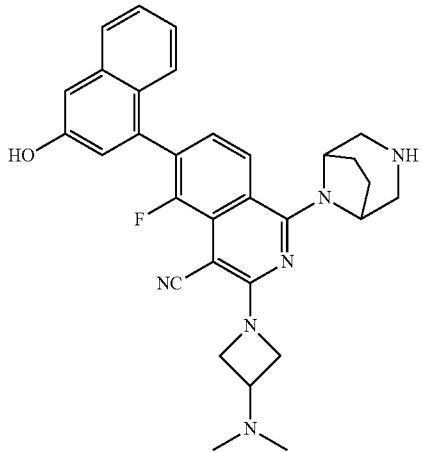 [SMILES: CN(C)C1CN(c2nc(N3C4CCC3CNC4)c3ccc(-c4cc(O)cc5ccccc45)c(F)c3c2C#N)C1]

Step 1. tert-butyl 8-(3-chloro-5-fluoro-4-iodo-6-(3-(methoxymethoxy)naphthalen-1-yl)isoquinolin-1-yl)-3,8-diazabicyclo[3.2.1]octane-3-carboxylate

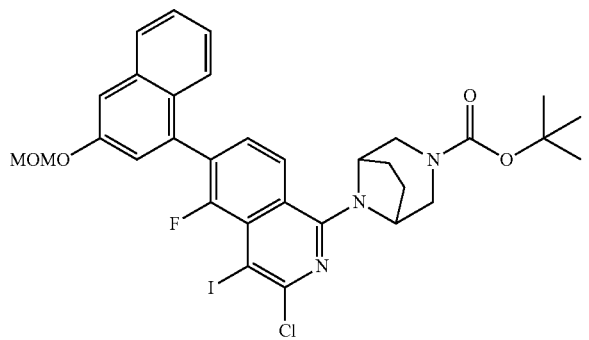

To a solution of Intermediate 2 (1.09 g, 1.886 mmol) in DMF (7.54 ml) was added NIS (0.445 g, 1.980 mmol) and the reaction mixture was stirred at 60° C. for 4 hr, then diluted with water and extracted with ethyl acetate. The organic layer was washed with water and brine, dried over sodium sulfate and concentrated. The crude product was purified by Biotage Isolera™ (10-50% ethyl acetate in hexanes) to provide the desired product as an off-white solid (1.01 g, 76%). LC-MS calculated for $C_{32}H_{33}ClFIN_3O_4$ (M+H)$^+$: m/z=704.1; found 648.0 (M−tBu)$^+$.

Step 2. tert-butyl 8-(3-chloro-4-cyano-5-fluoro-6-(3-(methoxymethoxy)naphthalen-1-yl)isoquinolin-1-yl)-3,8-diazabicyclo[3.2.1]octane-3-carboxylate

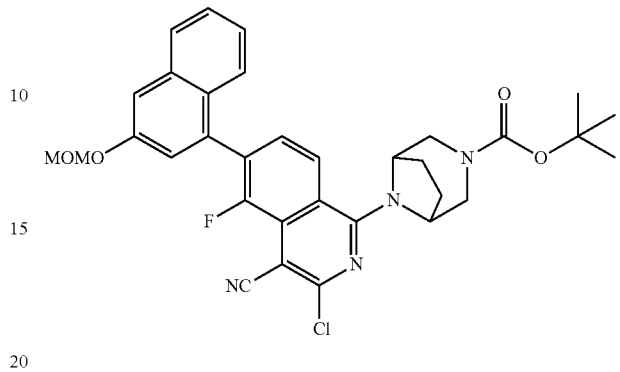

To a solution of tert-butyl 8-(3-chloro-5-fluoro-4-iodo-6-(3-(methoxymethoxy)naphthalen-1-yl)isoquinolin-1-yl)-3,8-diazabicyclo[3.2.1]octane-3-carboxylate (330 mg, 0.469 mmol) in DMF (2.0 ml) was added copper(I) cyanide (42.0 mg, 0.469 mmol) and the reaction flask was evacuated, back filled with nitrogen, then stirred at 100° C. for 1 hr. The mixture was quenched with water and a few drops of ammonium hydroxide were added. The mixture was then extracted with DCM. The organic layer was washed with water and brine, dried over sodium sulfate and concentrated. The crude product was purified by Biotage Isolera™ (0-100% ethyl acetate in hexanes) to provide the desired product (213 mg, 75%). LC-MS calculated for $C_{33}H_{33}ClFN_4O_4$ (M+H)$^+$: m/z=603.2; found 603.2.

Step 3. 1-(3,8-diazabicyclo[3.2.1]octan-8-yl)-3-(3-(dimethylamino)azetidin-1-yl)-5-fluoro-6-(3-hydroxynaphthalen-1-yl)isoquinoline-4-carbonitrile To a solution of tert-butyl 8-(3-chloro-4-cyano-5-fluoro-6-(3-(methoxymethoxy)naphthalen-1-yl)isoquinolin-1-yl)-3,8-diazabicyclo[3.2.1]octane-3-carboxylate (213 mg, 0.353 mmol) in DMA (3.53 ml) were added N,N-dimethylazetidin-3-amine dihydrochloride (73.4 mg, 0.424 mmol) and Hunig's base (185 μl, 1.060 mmol) and the reaction mixture was heated to 100° C. for 3 hr, then quenched with water and extracted with DCM. The organic layer was washed with water and brine, dried over sodium sulfate and concentrated. The crude product was dissolved in DCM (0.7 mL) and TFA (0.25 mL) was added. The mixture was stirred at r.t. for 30 mins, then diluted with methanol and purified using preparative LC/MS (pH=2, acetonitrile/water with TFA) to give the desired product as a TFA salt. LC-MS calculated for $C_{31}H_{32}FN_6O$ (M+H)$^+$: m/z=523.2; found 523.2.

Example 2. 3-(1-(3,8-diazabicyclo[3.2.1]octan-8-yl)-4-chloro-3-(3-(dimethylamino)azetidin-1-yl)-5-fluoro-6-(3-hydroxynaphthalen-1-yl)isoquinolin-7-yl)propanenitrile

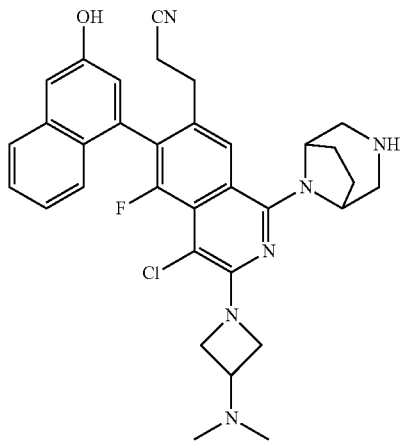 [SMILES: CN(C)C1CN(c2nc(N3C4CCC3CNC4)c3cc(CCC#N)c(-c4cc(O)cc5ccccc45)c(F)c3c2Cl)C1]

Step 1. tert-butyl 8-(7-(2-cyanoethyl)-3-(3-(dimethylamino)azetidin-1-yl)-5-fluoro-6-(3-(methoxymethoxy)naphthalen-1-yl)isoquinolin-1-yl)-3,8-diazabicyclo[3.2.1]octane-3-carboxylate

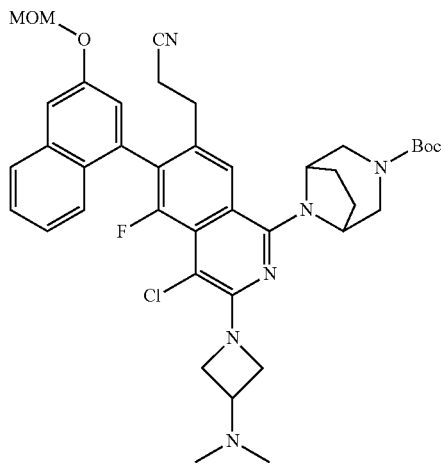

To a mixture of Intermediate 4 (300 mg, 0.475 mmol), N,N-dimethylazetidin-3-amine dihydrochloride (99 mg, 0.570 mmol), XantPhos Pd G2 (37.5 mg, 0.048 mmol) and cesium carbonate (774 mg, 2.377 mmol) was added dioxane (2.4 ml) and the reaction flask was evacuated, back filled with nitrogen, then stirred at 100° C. for 4 hr. The mixture was diluted with DCM and filtered through a plug of Celite. The filtrate was concentrated and the residue was purified by Biotage Isolera™ (2-4% MeOH in DCM) to provide the desired product as a yellow solid (239 mg, 72%). LC-MS calculated for $C_{40}H_{48}FN_6O_4$ (M+H)$^+$: m/z=695.4; found 695.4.

Step 2. tert-butyl 8-(4-chloro-7-(2-cyanoethyl)-3-(3-(dimethylamino)azetidin-1-yl)-5-fluoro-6-(3-(methoxymethoxy)naphthalen-1-yl)isoquinolin-1-yl)-3,8-diazabicyclo[3.2.1]octane-3-carboxylate

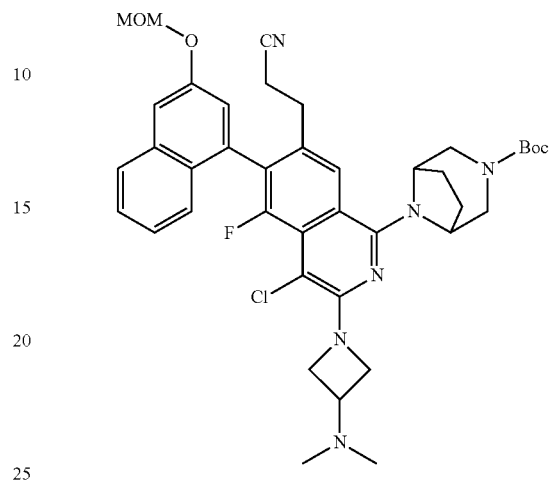

To a solution of tert-butyl 8-(7-(2-cyanoethyl)-3-(3-(dimethylamino)azetidin-1-yl)-5-fluoro-6-(3-(methoxymethoxy)naphthalen-1-yl)isoquinolin-1-yl)-3,8-diazabicyclo[3.2.1]octane-3-carboxylate (239 mg, 0.344 mmol) in DCM (1.720 ml) at −10° C. was added NCS (45.9 mg, 0.344 mmol). After 5 mins at this temperature, the reaction was quenched by the addition of sat. sodium bicarbonate and sat. sodium thiosulfate. The mixture was then diluted with water and extracted with DCM. The organic layer was dried over sodium sulfate and concentrated. The crude product was purified by Biotage Isolera™ (2-4% MeOh in DCM) to provide the desired product (153 mg, 61%). LC-MS calculated for $C_{40}H_{48}ClFN_6O_4$ (M+H)$^+$: m/z=729.3; found 729.3.

Step 3. 3-(1-(3,8-diazabicyclo[3.2.1]octan-8-yl)-4-chloro-3-(3-(dimethylamino)azetidin-1-yl)-5-fluoro-6-(3-hydroxynaphthalen-1-yl)isoquinolin-7-yl)propanenitrile To a solution of tert-butyl 8-(4-chloro-7-(2-cyanoethyl)-3-(3-(dimethylamino)azetidin-1-yl)-5-fluoro-6-(3-(methoxymethoxy)naphthalen-1-yl)isoquinolin-1-yl)-3,8-diazabicyclo[3.2.1]octane-3-carboxylate (15 mg, 0.021 mmol) in DCM (0.7 mL) was added TFA (0.5 mL) and the reaction mixture was allowed to stir at r.t. for 30 mins, then diluted with MeOH and purified using preparative LC/MS (pH=2, acetonitrile/water with TFA) to give the desired product as a TFA salt. LC-MS calculated for $C_{33}H_{35}ClFN_6O$ (M+H)$^+$: m/z=585.2; found 585.2.

Example 3. 3-(1-(3,8-diazabicyclo[3.2.1]octan-8-yl)-3-(3-(dimethylamino)azetidin-1-yl)-5-fluoro-6-(3-hydroxynaphthalen-1-yl)-4-methylisoquinolin-7-yl)propanenitrile

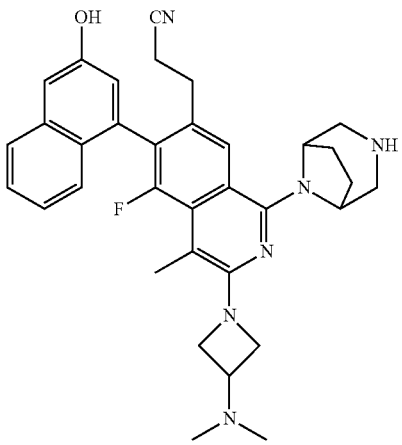 [SMILES: Cc1c(N2CC(N(C)C)C2)nc(N2C3CCC2CNC3)c2cc(CCC#N)c(-c3cc(O)cc4ccccc34)c(F)c12]

To a mixture of tert-butyl 8-(4-chloro-7-(2-cyanoethyl)-3-(3-(dimethylamino)azetidin-1-yl)-5-fluoro-6-(3-(methoxymethoxy)naphthalen-1-yl)isoquinolin-1-yl)-3,8-diazabicyclo[3.2.1]octane-3-carboxylate (Example 2, step 2; 20 mg, 0.029 mmol), sodium carbonate (9 m, 0.086 mmol, methylboronic acid (9 mg, 0.144 mmol), and Pd-132 (2 mg) were added dioxane/water (500 uL of a 4:1 solution) and the reaction flask was evacuated, back filled with nitrogen, then stirred at 100° C. overnight. The mixture was quenched with water and extracted with DCM. The organic layer was dried over sodium sulfate and concentrated. The crude product was redissolved in DCM (0.7 mL) and TFA (0.25 mL) was added. After 30 mins at r.t., MeOH was added and the mixture was purified using preparative LC/MS (pH=2, acetonitrile/water with TFA) to give the desired product as a TFA salt. LC-MS calculated for $C_{34}H_{38}FN_6O$ (M+H)$^+$: m/z=565.2; found 565.2.

Example 4. 3-(1-(3,8-diazabicyclo[3.2.1]octan-8-yl)-3-(3-(dimethylamino)azetidin-1-yl)-5-fluoro-6-(3-hydroxynaphthalen-1-yl)-4-phenylisoquinolin-7-yl)propanenitrile

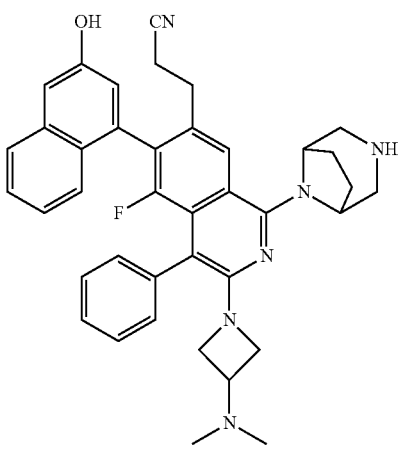 [SMILES: CN(C)C1CN(c2nc(N3C4CCC3CNC4)c3cc(CCC#N)c(-c4cc(O)cc5ccccc45)c(F)c3c2-c2ccccc2)C1]

To a mixture of tert-butyl 8-(4-chloro-7-(2-cyanoethyl)-3-(3-(dimethylamino)azetidin-1-yl)-5-fluoro-6-(3-(methoxymethoxy)naphthalen-1-yl)isoquinolin-1-yl)-3,8-diazabicyclo[3.2.1]octane-3-carboxylate (Example 2, step 2; 20 mg, 0.027 mmol), phenylboronic acid (7 mg, 0.058 mmol), XPhos Pd G2 (2.158 mg, 2.74 μmol) and sodium carbonate (8.72 mg, 0.082 mmol) were added dioxane (0.4 mL)/water (0.1 mL) and the reaction flask was evacuated, back filled with nitrogen, then stirred at 100° C. overnight. The reaction mixture was quenched with water and extracted with DCM. The organic layer was dried over sodium sulfate and concentrated. The crude product was dissolved in DCM (0.7 mL) and TFA (0.25 mL) was added. The reaction mixture was stirred at r.t. for 30 mins, then diluted with MeOH and purified using preparative LC/MS (pH=2, acetonitrile/water with TFA) to give the desired product as a TFA salt. LC-MS calculated for $C_{39}H_{40}FN_6O$ (M+H)$^+$: m/z=627.2; found 627.2.

Example 5. 3-(1-(3,8-diazabicyclo[3.2.1]octan-8-yl)-4-cyclopropyl-3-(3-(dimethylamino)azetidin-1-yl)-5-fluoro-6-(3-hydroxynaphthalen-1-yl)isoquinolin-7-yl)propanenitrile

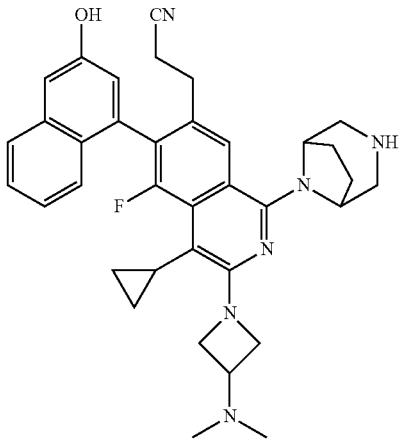 [SMILES: CN(C)C1CN(c2nc(N3C4CCC3CNC4)c3cc(CCC#N)c(-c4cc(O)cc5ccccc45)c(F)c3c2C2CC2)C1]

To a solution of zinc chloride (1.9 M in THF, 90 μL, 0.171 mmol) was added cyclopropylmagnesium bromide (0.5 M in THF, 343 μL, 0.171 mmol) and the resulting mixture was stirred for 2 hr at r.t. This solution was then added to a solution of tert-butyl 8-(4-chloro-7-(2-cyanoethyl)-3-(3-(dimethylamino)azetidin-1-yl)-5-fluoro-6-(3-(methoxymethoxy)naphthalen-1-yl)isoquinolin-1-yl)-3,8-diazabicyclo[3.2.1]octane-3-carboxylate (Example 2, Step 2; 25 mg, 0.034 mmol), potassium acetate (10.09 mg, 0.103 mmol) and t-Bu$_3$P Pd G2 (1.875 mg, 3.43 μmol) in THF (300 μL). The reaction flask was evacuated, back filled with nitrogen, then stirred at 65 degrees for 1 hr. The mixture was quenched with sat. ammonium chloride and extracted with DCM. The organic layer was dried over sodium sulfate and concentrated. The crude product was dissolve in DCM (0.7 mL) and TFA (0.25 mL) was added. After stirring at r.t. for 30 mins, the mixture was diluted with MeOH and purified using preparative LC/MS (pH=2, acetonitrile/water with TFA) to give the desired product as a TFA salt. LC-MS calculated for $C_{36}H_{40}FN_6O$ (M+H)$^+$: m/z=591.2; found 591.2.

Example 6. 1-(3,8-diazabicyclo[3.2.1]octan-8-yl)-7-(2-cyanoethyl)-3-(3-(dimethylamino)azetidin-1-yl)-5-fluoro-6-(3-hydroxynaphthalen-1-yl)isoquinoline-4-carbonitrile

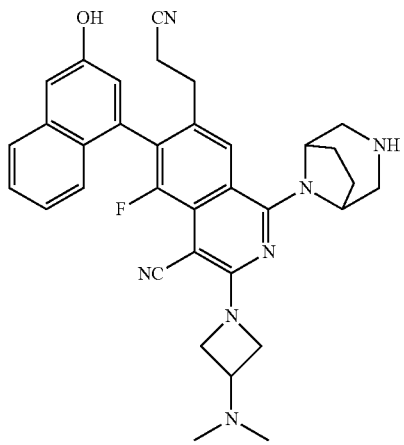 [SMILES: CN(C)C1CN(c2nc(N3C4CCC3CNC4)c3cc(CCC#N)c(-c4cc(O)cc5ccccc45)c(F)c3c2C#N)C1]

Step 1. tert-butyl 8-(4-bromo-3-chloro-7-(2-cyanoethyl)-5-fluoro-6-(3-(methoxymethoxy)naphthalen-1-yl)isoquinolin-1-yl)-3,8-diazabicyclo[3.2.1]octane-3-carboxylate

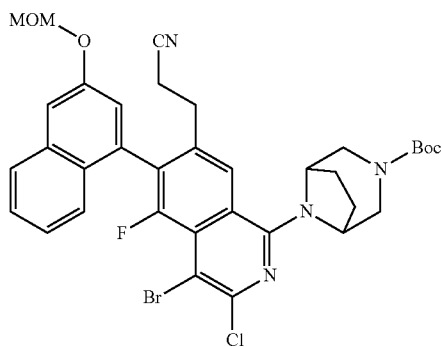

To a solution of Intermediate 4 (139 mg, 0.220 mmol) in DMF (1.101 ml) was added NBS (39.2 mg, 0.220 mmol) and the reaction mixture was stirred at r.t. for 30 mins, then quenched with water and extracted with ethyl acetate. The organic layer was washed with water and brine, dried over sodium sulfate and concentrated. The crude product was used in the next step without further purification (156 mg, 100%). LC-MS calculated for $C_{35}H_{36}BrClFN_4O_4$ (M+H)$^+$: m/z=709.2/711.2; found 653.2/655.2 (M−tBu)$^+$.

Step 2. tert-butyl 8-(3-chloro-4-cyano-7-(2-cyanoethyl)-5-fluoro-6-(3-(methoxymethoxy)naphthalen-1-yl)isoquinolin-1-yl)-3,8-diazabicyclo[3.2.1]octane-3-carboxylate

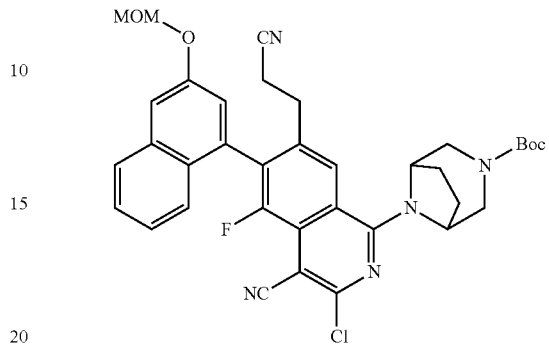

To a mixture of tert-butyl 8-(4-bromo-3-chloro-7-(2-cyanoethyl)-5-fluoro-6-(3-(methoxymethoxy)naphthalen-1-yl)isoquinolin-1-yl)-3,8-diazabicyclo[3.2.1]octane-3-carboxylate (156 mg, 0.220 mmol) and copper(I) cyanide (19.68 mg, 0.220 mmol) was added DMF (1.099 ml) and the reaction flask was evacuated, back filled with nitrogen, then stirred at 100° C. overnight. The mixture was then quenched with water and extracted with ethyl acetate. The organic layer was washed with water and brine, dried over sodium sulfate and concentrated. The crude product was purified by Biotage Isolera™ (2-4% MeOH in DCM) to provide the desired product (105 mg, 73%). LC-MS calculated for $C_{36}H_{36}ClFN_5O_4$ (M+H)$^+$: m/z=656.2/658.2; found 600.2/602.2 (M−tBu)$^+$.

Step 3. 1-(3,8-diazabicyclo[3.2.1]octan-8-yl)-7-(2-cyanoethyl)-3-(3-(dimethylamino)azetidin-1-yl)-5-fluoro-6-(3-hydroxynaphthalen-1-yl)isoquinoline-4-carbonitrile To a solution of tert-butyl 8-(3-chloro-4-cyano-7-(2-cyanoethyl)-5-fluoro-6-(3-(methoxymethoxy)naphthalen-1-yl)isoquinolin-1-yl)-3,8-diazabicyclo[3.2.1]octane-3-carboxylate (20 mg, 0.030 mmol) in DMA (0.5 mL) was added N,N-dimethylaminoazetidine, dihydrochloride (3 mg, 0.03 mmol) and Hunig's base (17 μL, 0.09 mmol) and the reaction mixture was heated to 100 degrees for 2 hr. The reaction was quenched with water and extracted with ethyl acetate. The organic layer was washed with water and brine, dried over sodium sulfate and concentrated. The crude product was dissolved in DCM (0.7 mL) and T F A (0.25 mL) was added. After stirring at r.t. for 30 mins, the reaction mixture was diluted with MeOH and purified using preparative LC/MS (pH=2, acetonitrile/water with TFA) to give the desired product as a TFA salt. LC-MS calculated for $C_{34}H_{35}FN_7O$ (M+H)$^+$: m/z=576.2; found 576.2.

Example 7. 1-(3,8-diazabicyclo[3.2.1]octan-8-yl)-7-(2-cyanoethyl)-5-fluoro-6-(3-hydroxynaphthalen-1-yl)-3-(((S)-1-methylpyrrolidin-2-yl)methoxy)isoquinoline-4-carbonitrile

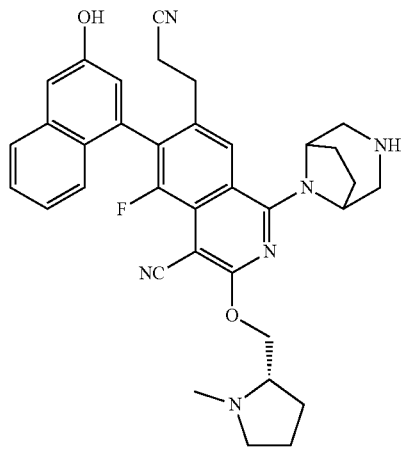 [SMILES: CN1CCC[C@H]1COc1nc(N2C3CCC2CNC3)c2cc(CCC#N)c(-c3cc(O)cc4ccccc34)c(F)c2c1C#N]

To a solution of (S)-(1-methylpyrrolidin-2-yl)methanol (8.78 mg, 0.076 mmol) in THF (0.38 ml) was added sodium hydride (60% in mineral oil, 4.57 mg, 0.114 mmol) and the reaction mixture was stirred at r.t. for 10 mins, then tert-butyl 8-(3-chloro-4-cyano-7-(2-cyanoethyl)-5-fluoro-6-(3-(methoxymethoxy)naphthalen-1-yl)isoquinolin-1-yl)-3,8-diazabicyclo[3.2.1]octane-3-carboxylate (Example 6, Step 2; 25 mg, 0.038 mmol) was added in one portion and the reaction mixture was heated to 65° C. for 1 hr. The reaction was quenched with water and extracted with DCM. The organic layer was dried over sodium sulfate and concentrated. The crude product was dissolved in DCM (0.7 mL) and TFA (0.25 mL) was added. After stirring at r.t. for 30 mins, the reaction mixture was diluted with MeOH and purified using preparative LC/MS (pH=2, acetonitrile/water with TFA) to give the desired product as a TFA salt. LC-MS calculated for $C_{35}H_{36}FN_6O_2$ (M+H)$^+$: m/z=591.2; found 591.2.

Example 8. 1-(3,8-diazabicyclo[3.2.1]octan-8-yl)-7-(2-cyanoethyl)-5-fluoro-6-(3-hydroxynaphthalen-1-yl)-3-((1-methylpiperidin-4-yl)oxy)isoquinoline-4-carbonitrile

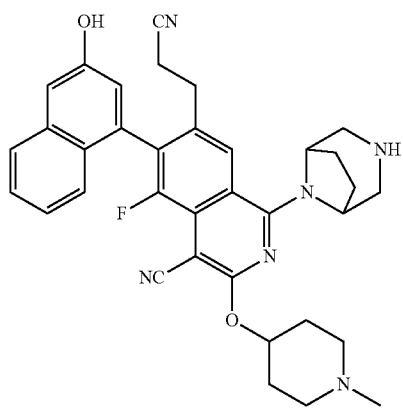 [SMILES: CN1CCC(Oc2nc(N3C4CCC3CNC4)c3cc(CCC#N)c(-c4cc(O)cc5ccccc45)c(F)c3c2C#N)CC1]

This compound was prepared in a similar manner to Example 7, with 1-methylpiperidin-4-ol as the alcohol partner. LC-MS calculated for $C_{35}H_{36}FN_6O_2$ (M+H)$^+$: m/z=591.2; found 591.2.

Example 9. 1-(3,8-diazabicyclo[3.2.1]octan-8-yl)-7-(2-cyanoethyl)-3-(3-((dimethylamino)methyl)phenyl)-5-fluoro-6-(3-hydroxynaphthalen-1-yl)isoquinoline-4-carbonitrile

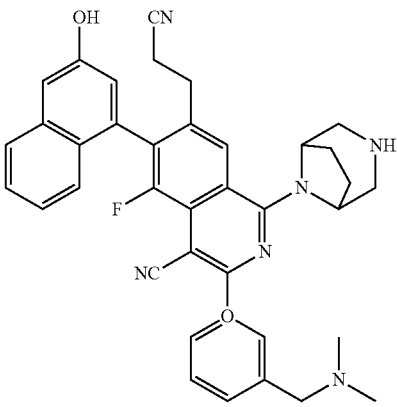

To a mixture of tert-butyl 8-(3-chloro-4-cyano-7-(2-cyanoethyl)-5-fluoro-6-(3-(methoxymethoxy)naphthalen-1-yl)isoquinolin-1-yl)-3,8-diazabicyclo[3.2.1]octane-3-carboxylate (Example 6, step 2; 15 mg, 0.023 mmol), (3-((dimethylamino)methyl)phenyl) boronic acid (8 mg, 0.046 mmol), XPhos Pd G2 (1.799 mg, 2.286 µmol) and sodium carbonate (2.423 mg, 0.023 mmol) were added dioxane (0.183 ml)/water (0.046 ml) and the reaction flask was evacuated, back filled with nitrogen, then stirred at 100° C. for 1 hr. The mixture was diluted with water and extracted with DCM. The residue was dissolved in DCM (0.7 mL) and TFA (0.3 mL) was added. After stirring at r.t. for 30 mins, the mixture was diluted with MeOH and purified using preparative LC/MS (pH=2, acetonitrile/water with TFA) to give the desired product as a TFA salt. LC-MS calculated for $C_{38}H_{36}FN_6O$ (M+H)$^+$: m/z=611.2; found 611.2.

Example 10. 1-((1R,4R)-2,5-diazabicyclo[2.2.2]octan-2-yl)-7-(2-cyanoethyl)-3-(3-(dimethylamino)azetidin-1-yl)-5-fluoro-6-(3-hydroxynaphthalen-1-yl)isoquinoline-4-carbonitrile

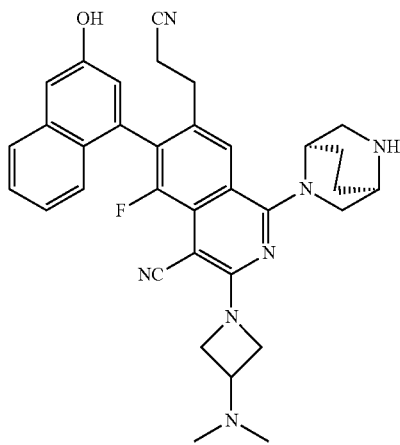 [SMILES: CN(C)C1CN(c2nc(N3C[C@H]4CC[C@@H]3CN4)c3cc(CCC#N)c(-c4cc(O)cc5ccccc45)c(F)c3c2C#N)C1]

Step 1. tert-butyl (1R,4R)-5-(3-chloro-7-(2-cyanoethyl)-5-fluoro-6-(3-(methoxymethoxy)naphthalen-1-yl)isoquinolin-1-yl)-2,5-diazabicyclo[2.2.2]octane-2-carboxylate

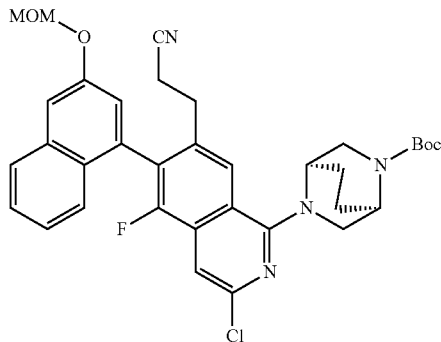

To a solution of Intermediate 5 (50 mg, 0.100 mmol), and tert-butyl (1R,4R)-2,5-diazabicyclo[2.2.2]octane-2-carboxylate (23.40 mg, 0.110 mmol) in DMA (1.002 ml) was added Hunig's base (35.0 μl, 0.200 mmol) and the mixture was heated 120° C. overnight. The reaction was quenched with water and extracted with ethyl acetate. The organic layer was washed with water and brine, dried over sodium sulfate and concentrated. The crude product was purified by Biotage Isolera™ (10-50% ethyl acetate) (16 mg, 25%). LC-MS calculated for $C_{35}H_{37}ClFN_4O_4$ (M+H)$^+$: m/z=631.2; found 575.2 (M–tBu)$^+$.

Step 2. 1-((1R,4R)-2,5-diazabicyclo[2.2.2]octan-2-yl)-7-(2-cyanoethyl)-3-(3-(dimethylamino)azetidin-1-yl)-5-fluoro-6-(3-hydroxynaphthalen-1-yl)isoquinoline-4-carbonitrile To a solution of tert-butyl (1R,4R)-5-(3-chloro-7-(2-cyanoethyl)-5-fluoro-6-(3-(methoxymethoxy)naphthalen-1-yl)isoquinolin-1-yl)-2,5-diazabicyclo[2.2.2]octane-2-carboxylate (16 mg, 0.025 mmol) in DCM (0.5 ml) was added NBS (4.51 mg, 0.025 mmol) and the reaction mixture was stirred at r.t. for 30 mins, then quenched with sat. sodium bicarbonte and sat. sodium thiosulfate and extracted with DCM. The organic layer was dried over sodium sulfate and concentrated. The crude product was dissolved in DMF (0.5 mL) and copper (I) cyanide (2.271 mg, 0.025 mmol) was added. The reaction flask was evacuated, back filled with nitrogen, then stirred at 100° C. overnight. The mixture was quenched with water, then a few drops of ammonium hydroxide were added and the mixture was extracted with ethyl acetate. The organic layer was washed with water and brine, dried over sodium sulfate and concentrated. The crude product was dissolved in DMA (0.5 mL) and N,N-dimethylazetidin-3-amine dihydrochloride (4.39 mg, 0.025 mmol) and Hunig's base (17.71 μl, 0.101 mmol) and the reaction mixture was heated to 100° C. The mixture was then quenched with water and extracted with ethyl acetate. The organic layer was washed with water and dried over sodium sulfate and concentrated. The crude product was dissolved in DCM (0.7 mL) and TFA (0.3 mL) was added. After 30 mins, the mixture was diluted with MeOH and purified using preparative LC/MS (pH=2, acetonitrile/water with TFA) to give the desired product as a TFA salt. LC-MS calculated for $C_{34}H_{35}FN_7O$ (M+H)$^+$: m/z=576.2; found 576.2.

Example 11. 1-((2S,4S)-4-amino-2-(hydroxymethyl)pyrrolidin-1-yl)-7-(2-cyanoethyl)-3-(3-(dimethylamino)azetidin-1-yl)-5-fluoro-6-(3-hydroxynaphthalen-1-yl)isoquinoline-4-carbonitrile

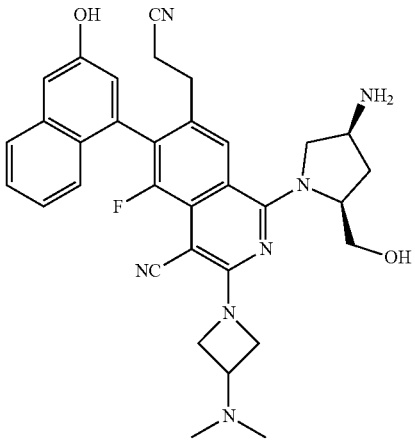 [SMILES: CN(C)C1CN(c2nc(N3C[C@@H](N)C[C@H]3CO)c3cc(CCC#N)c(-c4cc(O)cc5ccccc45)c(F)c3c2C#N)C1]

To a solution of Intermediate 6 (25 mg, 0.039 mmol) in acetonitrile (0.5 ml) was added Hunig's base (20.22 μl, 0.116 mmol), followed by tert-butyl ((3S,5S)-5-(hydroxymethyl)pyrrolidin-3-yl)carbamate (9.92 mg, 0.046 mmol). The reaction mixture was then heated to 100° C. for 1 hr. The reaction was quenched with water and extracted with DCM. The organic layer was dried over sodium sulfate and concentrated. The crude product was dissolved in DMF (0.5 mL) and copper (I) cyanide (3.46 mg, 0.039 mmol) was added. The reaction flask was evacuated, back filled with nitrogen, then stirred at 100° C. overnight. Hunig's base (20.22 μl, 0.116 mmol) and N,N-dimethylazetidin-3-amine dihydrochloride (6.68 mg, 0.039 mmol) were added and the reaction mixture was heated to 100° C. for 3 hr. The reaction was quenched with water and a few drops of ammonium hydroxide, then extracted with DCM. The organic layer was washed with water and brine, dried over sodium sulfate and concentrated. The crude product was dissolved in DCM (0.7 mL) and TFA (0.25 mL) was added. The reaction mixture was stirred at r.t. for 30 mins, then diluted with MeOH and purified using preparative LC/MS (pH=2, acetonitrile/water with TFA) to give the desired product as a TFA salt. LC-MS calculated for $C_{33}H_{35}FN_7O_2$ (M+H)$^+$: m/z=580.2; found 580.2.

Example 12. 7-(2-cyanoethyl)-1-(3-(cyanomethyl) pyrrolidin-1-yl)-3-(3-(dimethylamino)azetidin-1-yl)-5-fluoro-6-(3-hydroxynaphthalen-1-yl)isoquinoline-4-carbonitrile

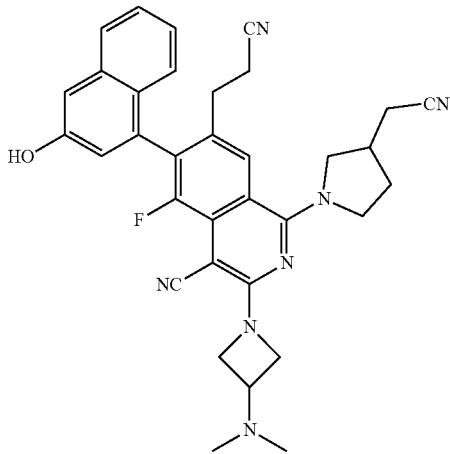 [SMILES: CN(C)C1CN(c2nc(N3CCC(CC#N)C3)c3cc(CCC#N)c(-c4cc(O)cc5ccccc45)c(F)c3c2C#N)C1]

This compound was prepared in a similar manner to Example 11, using 2-(pyrrolidin-3-yl)acetonitrile, hydrochloride as the amine coupling partner. LC-MS calculated for $C_{33}H_{35}FN_7O_2$ (M+H)$^+$: m/z=574.2; found 574.2.

Example 13. 1-((S)-3-aminopyrrolidin-1-yl)-7-(2-cyanoethyl)-3-(3-(dimethylamino)azetidin-1-yl)-5-fluoro-6-(3-hydroxynaphthalen-1-yl)isoquinoline-4-carbonitrile

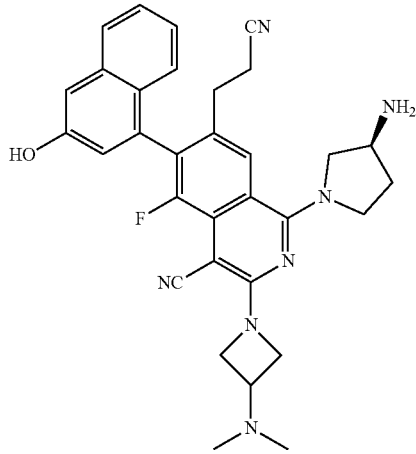 [SMILES: CN(C)C1CN(c2nc(N3CC[C@H](N)C3)c3cc(CCC#N)c(-c4cc(O)cc5ccccc45)c(F)c3c2C#N)C1]

This compound was prepared in a similar manner to Example 11, using tert-butyl (S)-pyrrolidin-3-ylcarbamate as the amine coupling partner. LC-MS calculated for $C_{33}H_{35}FN_7O_2$ (M+H)$^+$: m/z=550.2; found 550.2.

Example 14. 1-((2R,4S)-4-amino-2-methylpyrrolidin-1-yl)-7-(2-cyanoethyl)-3-(3-(dimethylamino) azetidin-1-yl)-5-fluoro-6-(3-hydroxynaphthalen-1-yl)isoquinoline-4-carbonitrile

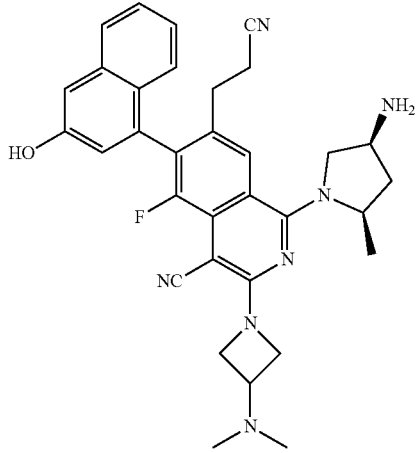 [SMILES: C[C@@H]1C[C@H](N)CN1c1nc(N2CC(N(C)C)C2)c(C#N)c2c(F)c(-c3cc(O)cc4ccccc34)c(CCC#N)cc12]

This compound was prepared in a similar manner to Example 11, using tert-butyl ((3S,4S)-4-methylpyrrolidin-3-yl)carbamate as the amine coupling partner. LC-MS calculated for $C_{33}H_{35}FN_7O_2$ (M+H)$^+$: m/z=564.2; found 564.2.

Example 15. 1-(3,8-diazabicyclo[3.2.1]octan-3-yl)-5-fluoro-3-(((2R,7aS)-2-fluorotetrahydro-1H-pyrrolizin-7a(5H)-yl)methoxy)-6-(3-hydroxynaphthalen-1-yl)-2,7-naphthyridine-4-carbonitrile

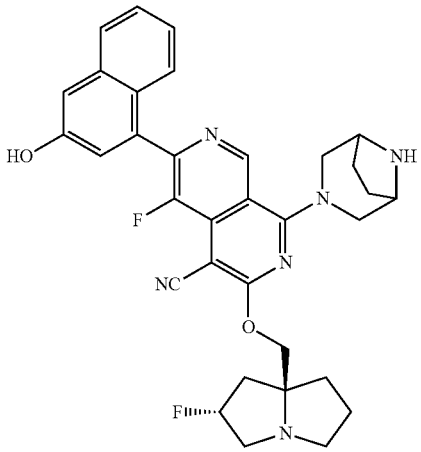 [SMILES: N#Cc1c(OC[C@@]23CCCN2C[C@H](F)C3)nc(N2CC3CCC(C2)N3)c2cnc(-c3cc(O)cc4ccccc34)c(F)c12]

Step 1. tert-butyl 3-(3,6-dichloro-4-cyano-5-fluoro-2,7-naphthyridin-1-yl)-3,8-diazabicyclo[3.2.1]octane-8-carboxylate

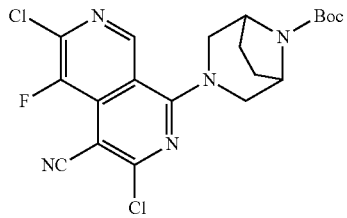 [SMILES: CC(C)(C)OC(=O)N1C2CCC1CN(c1nc(Cl)c(C#N)c3c(F)c(Cl)ncc13)C2]

To a solution of 1,3,6-trichloro-5-fluoro-2,7-naphthyridine-4-carbonitrile (102 mg, 0.369 mmol) in acetonitrile (1.845 ml) were added Hunig's base (97 μl, 0.553 mmol) and tert-butyl 3,8-diazabicyclo[3.2.1]octane-8-carboxylate (78 mg, 0.369 mmol) and the reaction mixture was stirred at r.t. for 30 mins, then quenched with water and extracted with DCM. The organic layer was dried over sodium sulfate and concentrated. The crude product was purified by Biotage Isolera™ (1-5% MeOH in DCM) to provide the desired product (149 mg, 89%). LCMS calculated for $C_{20}H_{21}Cl_2FN_5O_2$ (M+H)$^+$: m/z=452.2/454.2 Found: 452.2/454.2.

Step 6. 1-(3,8-diazabicyclo[3.2.1]octan-3-yl)-5-fluoro-3-(((2R,7aS)-2-fluorotetrahydro-1H-pyrrolizin-7a(5H)-yl)methoxy)-6-(3-hydroxynaphthalen-1-yl)-2,7-naphthyridine-4-carbonitrile To a solution of ((2R,7aS)-2-fluorotetrahydro-1H-pyrrolizin-7a(5H)-yl)methanol (10.56 mg, 0.066 mmol) in THF (0.332 ml) was added sodium hydride (2.65 mg, 0.066 mmol, 60% in mineral oil) and the reaction mixture was stirred at r.t. for 10 mins, then tert-butyl 3-(3,6-dichloro-4-cyano-5-fluoro-2,7-naphthyridin-1-yl)-3,8-diazabicyclo[3.2.1]octane-8-carboxylate (30 mg, 0.066 mmol) was added and the reaction mixture was heated to 60° for 1 hr. The reaction was quenched with water and extracted with DCM. The organic layer was dried over sodium sulfate and concentrated. To the crude product were added 4-(4,4,5,5-tetramethyl-1,3,2-dioxaborolan-2-yl)naphthalen-2-ol (17.92 mg, 0.066 mmol), tetrakis(triphenylphosphine) palladium(0) (7.66 mg, 6.63 μmol), sodium carbonate (21.09 mg, 0.199 mmol) and 4:1 dioxane/water (500 uL) and the reaction flask was evacuated, back filled with nitrogen, then stirred at 70° C. overnight. The reaction was quenched with water and extracted with DCM. The organic layer was dried over sodium sulfate and concentrated. The crude product was dissolved in DCM (0.7 mL) and TFA (0.3 mL) was added. The reaction mixture was stirred at r.t. for 30 mins, then diluted with MeOH and purified by RP-HPLC (pH 2) to provide the desired product. LCMS calculated for $C_{33}H_{33}F_2N_6O_2$ (M+H)$^+$: m/z=583.2 Found: 583.2.

Example 16. 1-(3,8-diazabicyclo[3.2.1]octan-3-yl)-3-(3-(dimethylamino)-3-methylazetidin-1-yl)-6-(8-ethyl-7-fluoro-3-hydroxynaphthalen-1-yl)-5-fluoro-2,7-naphthyridine-4-carbonitrile

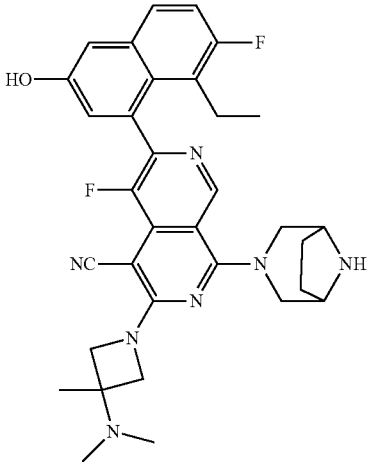 [SMILES: CCc1c(F)ccc2cc(O)cc(-c3ncc4c(N5CC6CCC(C5)N6)nc(N5CC(C)(N(C)C)C5)c(C#N)c4c3F)c12]

Step 1. 7-fluoro-8-((triisopropylsilyl)ethynyl)naphthalene-1,3-diol

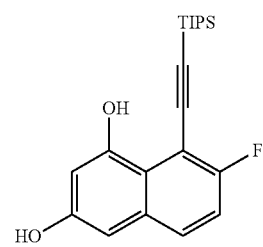

To a 40 mL vial charged with a magnetic stir bar was added 7-fluoronaphthalene-1,3-diol (1 g, 5.61 mmol), potassium acetate (1.102 g, 11.23 mmol), dichloro(p-cymene)ruthenium(II) dimer (0.344 g, 0.561 mmol), (bromoethynyl)triisopropylsilane (1.760 g, 6.74 mmol) and dioxane (11 mL). The mixture was degassed with N$_2$ for 10 mins and stirred at 110° C. overnight. Then the reaction was filtered through a pad of Celite and rinsed with EtOAc. The filtrate was diluted with water and EtOAc and the phases were separated. The aqueous phase was extracted EtOAc (2×10 mL). The organic phases were combined, washed with brine, dried over sodium sulfate, filtered and concentrated under vacuum. The residue was purified via flash-chromatography column (Biotage 40 g column, 0 to 40% EtOAc in Hexanes) to deliver the title compound as a brown oil (1.5 g, 75% yield). LCMS calculated for $C_{24}H_{30}F_4O_5SSi$ (M+H)$^+$: m/z=359.2, Found: 359.1.

Step 2. 7-fluoro-3-(methoxymethoxy)-8-((triisopropylsilyl)ethynyl)naphthalen-1-ol

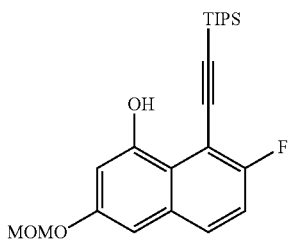

To a 40 mL vial charged with a magnetic stir bar was added 7-fluoro-8-((triisopropylsilyl) ethynyl)naphthalene-1, 3-diol (1 g, 2.79 mmol), dichloromethane (9 ml), and DIPEA (1.461 ml, 8.37 mmol). The mixture was cooled to 0° C. before MOM-Cl (0.318 ml, 4.18 mmol) was added dropwise via syringe. The reaction was stirred for 45 mins at 0° C. After the indicated time, the reaction was diluted with water (10 mL), the phases were separated and the aqueous layer was extracted with DCM (2×10 mL). The combined organic layers were dried over sodium sulfate, filtered and concentrated under vacuum. The residue was purified via flash-chromatography column (40 g Biotage column, 0 to 30% EtOAc in Hexanes) to deliver the title compound as a brown oil (0.93 g, 83% yield). LCMS calculated for $C_{23}H_{31}FO_3Si$ (M+H)$^+$: m/z=403.2, Found: 403.1.

Step 3. 7-fluoro-3-(methoxymethoxy)-8-((triisopropylsilyl)ethynyl)naphthalen-1-yl trifluoromethanesulfonate

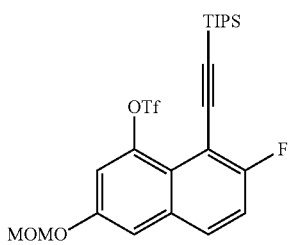

To a 40 mL vial charged with a magnetic stir bar was added 7-fluoro-3-(methoxymethoxy)-8-((triisopropylsilyl) ethynyl)naphthalen-1-ol (1.07 g, 2.66 mmol), DIPEA (1.393 ml, 7.97 mmol), and dichloromethane (13 ml). The mixture was cooled to −40° C. before Tf$_2$O (0.674 ml, 3.99 mmol) was added dropwise via syringe. The reaction was stirred for 45 mins at −40° C. After the indicated time, the reaction was diluted with water (10 mL), the phases were separated and the aqueous layer was extracted DCM (2×10 mL). The combined organic layers were dried over sodium sulfate, filtered and concentrated under vacuum. The residue was purified via flash-chromatography column (40 g Biotage column, 0 to 20% EtOAc in Hexanes) to deliver the title compound as a yellow oil (1.21 g, 85% yield). LCMS calculated for $C_{24}H_{30}F_4O_5SSi$ (M+H)$^+$: m/z=535.2, Found: 535.1.

Step 4. ((2-fluoro-6-(methoxymethoxy)-8-(4,4,5,5-tetramethyl-1,3,2-dioxaborolan-2-yl)naphthalen-1-yl)ethynyl)triisopropylsilane

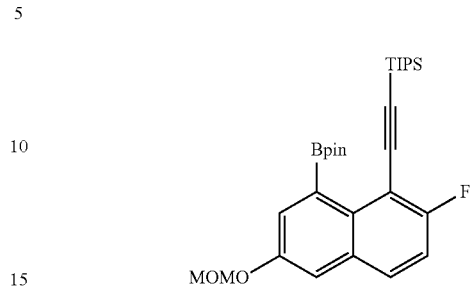

To a 40 mL vial charged with a magnetic stir bar was added 7-fluoro-3-(methoxymethoxy)-8-((triisopropylsilyl) ethynyl)naphthalen-1-yl trifluoromethanesulfonate (0.94 g, 1.758 mmol), toluene (9 ml) potassium acetate (0.604 g, 6.15 mmol), bis(pinacolato)diboron (0.893 g, 3.52 mmol), Pd(dppf)Cl$_2$·CH$_2$Cl$_2$ (144 mg, 0.176 mmol) and the mixture was degassed with N$_2$ for 10 mins then heated to 110° C. for 2 hrs. After the indicated time, the reaction was filtered to remove solids and washed with EtOAc. The filtrate was diluted with EtOAc and water. The phases were separated and the aqueous phase was extracted with EtOAc (2×20 mL). The organic phases were combined, washed with brine, dried over sodium sulfate, filtered and concentrated under vacuum. The residue was purified via flash-chromatography column (40 g Biotage column, 0 to 20% EtOAc in Hexanes) to deliver the desired title compound as a light yellow powder (0.54 g, 60% yield). LCMS calculated for $C_{29}H_{42}BFO_4Si$ (M+H)$^+$: m/z=513.3, Found: 513.2.

Step 5. 2-(8-ethyl-7-fluoro-3-(methoxymethoxy) naphthalen-1-yl)-4,4,5,5-tetramethyl-1,3,2-dioxaborolane

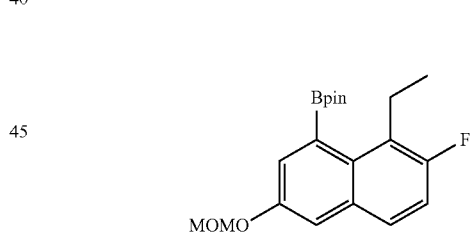

To a 40 mL vial charged with a magnetic stir bar was added ((2-fluoro-6-(methoxymethoxy)-8-(4,4,5,5-tetramethyl-1,3,2-dioxaborolan-2-yl)naphthalen-1-yl)ethynyl)triisopropylsilane (0.78 g, 1.522 mmol), DMF (3 ml) and cesium fluoride (0.694 g, 4.57 mmol). The mixture was stirred for 2 h at rt. After the indicated time, the reaction was quenched with water (10 mL), and the aqueous layer was extracted with EtOAc (3×10 mL). The combined organic phases were washed with brine, dried over sodium sulfate, filtered and concentrated under vacuum. The residue was re-dissolved in MeOH (10 ml) and Pd on carbon (0.162 g, 0.152 mmol, 10% wt) was added, the resulting mixture was stirred at rt under H$_2$ balloon for 2 hours. When the reaction was complete, the mixture was filtered through Celite and rinsed with MeOH. The filtrate was concentrated under vacuum and purified via flash-chromatography column (40 g Biotage column, 0 to 20% EtOAc in Hexanes) to deliver the desired title compound as a colorless waxy solid (0.25 g, 46% yield). LCMS calculated for $C_{20}H_{26}BFO_4$ $(M+H)^+$: m/z=361.2, Found: 361.1.

Step 6. tert-butyl 3-(6-chloro-4-cyano-3-(3-(dimethylamino)-3-methylazetidin-1-yl)-5-fluoro-2,7-naphthyridin-1-yl)-3,8-diazabicyclo[3.2.1]octane-8-carboxylate

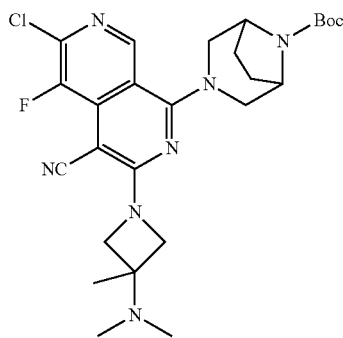 [SMILES: CN(C)C1(C)CN(c2nc(N3CC4CCC(C3)N4C(=O)OC(C)(C)C)c3cnc(Cl)c(F)c3c2C#N)C1]

To a 40 mL vial charged with a magnetic stir bar was added tert-butyl 3-(3,6-dichloro-4-cyano-5-fluoro-2,7-naphthyridin-1-yl)-3,8-diazabicyclo[3.2.1]octane-8-carboxylate (Example 15, Step 1; 1 g, 2.211 mmol), N,N-3-trimethylazetidin-3-amine dihydrochloride (0.496 g, 2.65 mmol), dioxane (7 ml) and DIPEA (1.545 ml, 8.84 mmol). The mixture was heated at 60° C. for 4 h. After the indicated time, the reaction mixture was concentrated under vacuum and purified via flash-chromatography column (40 g Biotage column, 0 to 30% MeOH in DCM) to deliver the title compound as a brown solid (0.98 g, 84% yield). LCMS calculated for $C_{26}H_{33}ClFN_7O_2$ $(M+H)^+$: m/z=530.2, Found: 530.2.

Step 7. 1-(3,8-diazabicyclo[3.2.1]octan-3-yl)-3-(3-(dimethylamino)-3-methylazetidin-1-yl)-6-(8-ethyl-7-fluoro-3-hydroxynaphthalen-1-yl)-5-fluoro-2,7-naphthyridine-4-carbonitrile To a 5 mL vial charged with a magnetic stir bar was added tert-butyl 3-(6-chloro-4-cyano-3-(3-(dimethylamino)-3-methylazetidin-1-yl)-5-fluoro-2,7-naphthyridin-1-yl)-3,8-diazabicyclo[3.2.1]octane-8-carboxylate (0.053 g, 0.1 mmol), 2-(8-ethyl-7-fluoro-3-(methoxymethoxy)naphthalen-1-yl)-4,4,5,5-tetramethyl-1,3,2-dioxaborolane (0.043 g, 0.120 mmol), $K_2CO_3$ (0.041 g, 0.300 mmol), XPhos Pd G4 (0.017 g, 0.020 mmol), dioxane (1 ml) and water (0.250 ml). The mixture was degassed with $N_2$ for 10 mins and then heated at 100° C. for 6 h. After the indicated time, the reaction was diluted with EtOAc and water. The phases were separated and the aqueous phase was extracted with EtOAc (2×10 mL). The organic phases were combined, washed with brine, dried over sodium sulfate, filtered and concentrated in vacuum. The residue was then dissolved in 1 mL DCM and 0.5 mL TFA and stirred at rt for 1 h. The mixture was then concentrated in vacuum and the resulting residue was purified on Prep HPLC (ACN/$H_2O$/TFA) to give the title compound as a TFA salt. LCMS calculated for $C_{26}H_{33}ClFN_7O_2$ $(M+H)^+$: m/z=584.3. Found: 584.2.

Example A. GDP-GTP Exchange Assay

The inhibitor potency of the exemplified compounds was determined in a fluorescence based guanine nucleotide exchange assay, which measures the exchange of bodipy-GDP (fluorescently labeled GDP) for GppNHp (Non-hydrolyzable GTP analog) to generate the active state of KRAS in the presence of SOS1 (guanine nucleotide exchange factor). Inhibitors were serially diluted in DMSO and a volume of 0.1 μL was transferred to the wells of a black low volume 384-well plate. 5 μL/well volume of bodipy-loaded KRAS G12C diluted to 5 nM in assay buffer (25 mM Hepes pH 7.5, 50 mM NaCl, 10 mM MgCl2 and 0.01% Brij-35) was added to the plate and pre-incubated with inhibitor for 2 hours at ambient temperature. Appropriate controls (enzyme with no inhibitor or with a G12C inhibitor (AMG-510)) were included on the plate. The exchange was initiated by the addition of a 5 μL/well volume containing 1 mM GppNHp and 300 nM SOS1 in assay buffer. The 10 μL/well reaction concentration of the bodipy-loaded KRAS G12C, GppNHp, and SOS1 were 2.5 nM, 500 uM, and 150 nM, respectively. The reaction plates were incubated at ambient temperature for 2 hours, a time estimated for complete GDP-GTP exchange in the absence of inhibitor. For the KRAS G12D and G12V mutants, similar guanine nucleotide exchange assays were used with 2.5 nM as final concentration for the bodipy loaded KRAS proteins and with 4 hours and 3 hours incubation after adding GppNHp-SOS1 mixture for G12D and G12V respectively. A cyclic peptide described to selectively bind G12D mutant (Sakamoto et al., BBRC 484.3 (2017), 605-611) or internal compounds with confirmed binding were used as positive controls in the assay plates. Fluorescence intensities were measured on a PheraStar plate reader instrument (BMG Labtech) with excitation at 485 nm and emission at 520 nm.

Either GraphPad prism or XLfit was used to analyze the data. The $IC_{50}$ values were derived by fitting the data to a four parameter logistic equation producing a sigmoidal dose-response curve with a variable Hill coefficient. Prism equation: Y=Bottom+(Top−Bottom)/(1+10^((Log $IC_{50}$−X)*Hill slope)); XLfit equation: Y=(A+((B−A)/(1+ ((X/C)^D)))) where X is the logarithm of inhibitor concentration and Y is the response.

The KRAS_G12D and G12V exchange assay $IC_{50}$ data are provided in Table 1 below. The symbol "†" indicates $IC_{50}$≤100 nM, "††" indicates $IC_{50}$>100 nM but ≤1 μM; and "†††" indicates $IC_{50}$ is >1 μM but ≤5 μM, "††††" indicates $IC_{50}$ is >5 μM but ≤10 μM.

TABLE 1

| | G12D Exchange $IC_{50}$ |
|---|---|
| Example 1 | † |
| Example 2 | †† |
| Example 3 | †† |
| Example 4 | †††† |
| Example 5 | †† |
| Example 6 | †† |
| Example 7 | †† |
| Example 8 | †† |
| Example 9 | †† |
| Example 10 | †† |
| Example 11 | †† |
| Example 12 | † |
| Example 13 | † |
| Example 14 | † |
| Example 15 | † |
| Example 16 | † |

Example B: Luminescent Viability Assay

MIA PaCa-2 (KRAS G12C; ATCC® CRL-1420), A427 (KRAS G12D; ATCC® HTB53) and NCI-H838 (KRAS WT; ATCC® CRL-5844) cells are cultured in RPMI 1640 media supplemented with 10% FBS (Gibco/Life Technologies). The cells are seeded (5×10³ cells/well/in 50 uL) into black, clear bottomed 96-well Greiner tissue culture plates and cultured overnight at 37° C., 5% $CO_2$. After overnight culture, 50 uL per well of serially diluted test compounds (2× final concentration) are added to the plates and incubated for 3 days. At the end of the assay, 100 ul/well of CellTiter-Glo reagent (Promega) is added. Luminescence is read after 15 minutes with a TopCount (PerkinElmer). $IC_{50}$ determination is performed by fitting the curve of percent inhibition versus the log of the inhibitor concentration using the GraphPad Prism 7 software.

Example C: Cellular pERK HTRF Assay

MIA PaCa-2 (KRAS G12C; ATCC® CRL-1420), A427 (KRAS G12D; ATCC® HTB53), HPAF-II (KRAS G12D; ATCC® CRL-1997) and NCI-H838 (KRAS WT; ATCC® CRL-5844) cells are purchased from ATCC and maintained in RPMI 1640 media supplemented with 10% FBS (Gibco/Life Technologies). The cells are plated at 5000 cells per well (8 uL) into Greiner 384-well low volume, flat-bottom, tissue culture treated white plates and incubated overnight at 37° C., 5% $CO_2$. The next morning, test compound stock solutions are diluted in media at 3× the final concentration, and 4 uL are added to the cells. The plate is mixed by gentle rotation for 30 seconds (250 rpm) at room temperature. The cells are incubated with the KRAS G12C and G12D compounds for 4 hours or 2 hours respectively at 37° C., 5% $CO_2$.

4 uL of 4× lysis buffer with blocking reagent (1:25) (Cisbio) are added to each well and plates are rotated gently (300 rpm) for 30 minutes at room temperature. 4 uL per well of Cisbio anti Phospho-ERK ½ d2 is mixed with anti Phospho-ERK ½ Cryptate (1:1) are added to each well, mixed by rotation and incubated overnight in the dark at room temperature. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 7 software.

Example D: Whole Blood pERK1/2 HTRF Assay

MIA PaCa-2 cells (KRAS G120; ATCC® CRL-1420) and HPAF-II (KRAS G12D; ATCC® CRL-1997) are maintained in RPMI 1640 with 10% FBS (Gibco/Life Technologies). The cells are seeded into 96 well tissue culture plates (Corning #3596) at 25000 cells per well in 100 uL media and cultured for 2 days at 37° C., 5% $CO_2$ so that they are approximately 80% confluent at the start of the assay. Whole Blood are added to the 1 uL dots of compounds (prepared in DMSO) in 96 well plates and mixed gently by pipetting up and down so that the concentration of the compound in blood is 1× of desired concentration. The media is aspirated from the cells and 50 uL per well of whole blood with G12C or G12D compound is added and incubated for 4 or 2 hours respectively at 37° C., 5% $CO_2$. After dumping the blood, the plates are gently washed twice by adding PBS to the side of the wells and dumping the PBS from the plate onto a paper towel, tapping the plate to drain well. 50 ul/well of 1× lysis buffer #1 (Cisbio) with blocking reagent (1:25) (Cisbio) is then added and incubated at room temperature for 30 minutes with shaking (250 rpm). Following lysis, 16 uL of lysate is transferred into 384-well Greiner small volume white plate using an Assist Plus (Integra Biosciences, NH).

4 uL of 1:1 mixture of anti Phospho-ERK ½ d2 and anti Phospho-ERK ½ Cryptate (Cisbio) is added to the wells using the Assist Plus and incubated at room temperature overnight in the dark. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 7 software.

Example E: Ras Activation Elisa

The 96-Well Ras Activation ELISA Kit (Cell Bioiabs Inc; #STA441) uses the Raft RBD (Rho binding domain) bound to a 96-well plate to selectively pull down the active form of Ras from cell lysates. The captured GTP-Ras is then detected by a pan-Ras antibody and HRP-conjugated secondary antibody.

MIA PaCa-2 cells (KRAS G12C; ATCC® CRL-1420) and HPAF-II (KRAS G12D; ATCC® CRL-1997) are maintained in RPMI 1640 with 10% FBS (Gibco/Life Technologies). The cells are seeded into 96 well tissue culture plates (Corning #3596) at 25000 cells per well in 100 uL media and cultured for 2 days at 37° C., 5% $CO_2$ so that they are approximately 80% confluent at the start of the assay. The cells are treated with compounds for either 2 hours or overnight at 37° C., 5% $CO_2$. At the time of harvesting, the cells are washed with PBS, drained well and then lysed with 50 uL of the 1× Lysis buffer (provided by the kit) plus added Halt Protease and Phosphatase inhibitors (1:100) for 1 hour on ice.

The Raf-1 RBD is diluted 1:500 in Assay Diluent (provided in kit) and 100 μL of the diluted Raf-1 RBD is added to each well of the Raf-1 RBD Capture Plate. The plate is covered with a plate sealing film and incubated at room temperature for 1 hour on an orbital shaker. The plate is washed 3 times with 250 μL 1× Wash Buffer per well with thorough aspiration between each wash. 50 μL of Ras lysate sample (10-100 μg) is added per well in duplicate. A "no cell lysate" control is added in a couple of wells for background determination. 50 μL of Assay Diluent is added to all wells immediately to each well and the plate is incubated at room temperature for 1 hour on an orbital shaker. The plate is washed 5 times with 250 μL 1× Wash Buffer per well with thorough aspiration between each wash. 100 μL of the diluted Anti-pan-Ras Antibody is added to each well and the plate is incubated at room temperature for 1 hour on an orbital shaker. The plate is washed 5 times as previously. 100 μL of the diluted Secondary Antibody, HRP Conjugate is added to each well and the plate is incubated at room temperature for 1 hour on an orbital shaker. The plate is washed 5 times as previously and drained well. 100 μL of Chemiluminescent Reagent (provided in the kit) is added to each well, including the blank wells. The plate is incubated at room temperature for 5 minutes on an orbital shaker before the luminescence of each microwell is read on a plate luminometer. The % inhibition is calculated relative to the DMSO control wells after a background level of the "no lysate control" is subtracted from all the values. $IC_{50}$ determination is performed by fitting the curve of inhibitor percent inhibition versus the log of the inhibitor concentration using the GraphPad Prism 7 software.

Example F: Inhibition of RAS-RAF and PI3K-AKT Pathways

The cellular potency of compounds was determined by measuring phosphorylation of KRAS downstream effectors extracellular-signal-regulated kinase (ERK), ribosomal S6 kinase (RSK), AKT (also known as protein kinase B, PKB) and downstream substrate S6 ribosomal protein.

To measure phosphorylated extracellular-signal-regulated kinase (ERK), ribosomal S6 kinase (RSK), AKT and S6 ribosomal protein, cells (details regarding the cell lines and types of data produced are further detailed in Table 2 were seeded overnight in Corning 96-well tissue culture treated plates in RPMI medium with 10% FBS at $4 \times 10^4$ cells/well. The following day, cells were incubated in the presence or absence of a concentration range of test compounds for 4 hours at 37° C., 5% $CO_2$. Cells were washed with PBS and lysed with 1× lysis buffer (Cisbio) with protease and phosphatase inhibitors. 10 μg of total protein lysates was subjected to SDS-PAGE and immunoblot analysis using following antibodies: phospho-ERK1/2-Thr202/Tyr204 (#9101L), total-ERK1/2 (#9102L), phosphor-AKT-Ser473 (#4060L), phospho-p90RSK-Ser380 (#11989S) and phospho-S6 ribosomal protein-Ser235/Ser236 (#2211S) are from Cell Signaling Technologies (Danvers, Mass.).

TABLE 2

| Cell Line | Histology | KRAS alteration | Readout |
|---|---|---|---|
| H358 | Lung | G12C | pERK, pAKT |
| MIA PaCa-2 | Pancreas | G12C | pERK, pAKT |
| HPAF II | Pancreas | G12D | pERK, pAKT |
| SU.86.86 | Pancreas | G12D | pERK, pAKT |
| PaTu 8988s | Pancreas | G12V | pERK, pAKT |
| H441 | Lung | G12V | pERK, pAKT |

Example G: In Vivo Efficacy Studies

Mia-Paca-2 human pancreatic cancer cells were obtained from the American Type Culture Collection and maintained in RPMI media supplemented with 10% FBS. For efficacy studies experiments, $5 \times 10^6$ Mia-Paca-2 cells were inoculated subcutaneously into the right hind flank of 6- to 8-week-old BALB/c nude mice (Charles River Laboratories, Wilmington, Mass., USA). When tumor volumes were approximately 150-250 mm3, mice were randomized by tumor volume and compounds were orally administered. Tumor volume was calculated using the formula $(L \times W^2)/2$, where L and W refer to the length and width dimensions, respectively. Tumor growth inhibition was calculated using the formula $(1-(V_T/V_C)) \times 100$, where $V_T$ is the tumor volume of the treatment group on the last day of treatment, and $V_C$ is the tumor volume of the control group on the last day of treatment. Two-way analysis of variance with Dunnett's multiple comparisons test was used to determine statistical differences between treatment groups (GraphPad Prism). Mice were housed at 10-12 animals per cage, and were provided enrichment and exposed to 12-hour light/dark cycles. Mice whose tumor volumes exceeded limits (10% of body weight) were humanely euthanized by $CO_2$ inhalation. Animals were maintained in a barrier facility fully accredited by the Association for Assessment and Accreditation of Laboratory Animal Care, International. All of the procedures were conducted in accordance with the US Public Service Policy on Human Care and Use of Laboratory Animals and with Incyte Animal Care and Use Committee Guidelines.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:
1. A compound having Formula I:

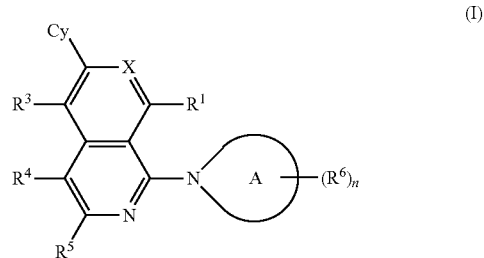

or a pharmaceutically acceptable salt thereof,
wherein:
$R^1$ is selected from H, D, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, and $BR^{h1}R^{i1}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;
X is N or $CR^2$;
$R^2$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$alkylene, $C_{6-10}$ aryl-$C_{1-3}$alkylene, 5-10 membered heteroaryl-$C_{1-3}$alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, and $BR^{h2}R^{i2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$alkylene, $C_{6-10}$ aryl-$C_{1-3}$alkylene and 5-10 membered heteroaryl-$C_{1-3}$ alkylene are each optionally substituted with 1, 2, 3, or 4 substituents independently selected from $R^{20}$;
Cy is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^3$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$alkylene, $C_{6-10}$ aryl-$C_{1-3}$alkylene, 5-10 membered heteroaryl-$C_{1-3}$alkylene, halo, D, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NOR^{a3})R^{b3}$, $C(=NR^{e3})NR^{c3}R^{d3}$, $NR^{c3}C(=NR^{e3})NR^{c3}R^{d3}$, $NR^{c3}C(=NR^{e3})R^{b3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, and $BR^{h3}R^{i3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$alkylene and 5-10 membered heteroaryl-$C_{1-3}$alkylene are each optionally substituted with 1, 2, 3, or 4 substituents independently selected from $R^{30}$;

$R^4$ is selected from $C_{1-6}$alkyl, $C_{2-6}$alkenyl, $C_{2-6}$alkynyl, $C_{1-6}$haloalkyl, $C_{3-10}$cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$alkylene, $C_{6-10}$ aryl-$C_{1-3}$alkylene, 5-10 membered heteroaryl-$C_{1-3}$alkylene, halo, D, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NOR^{a4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $BR^{h4}R^{i4}$; wherein said $C_{1-6}$alkyl, $C_{2-6}$alkenyl, $C_{2-6}$alkynyl, $C_{3-10}$cycloalkyl, 4-10 membered heterocycloalkyl, $C_{6-10}$ aryl, 5-10 membered heteroaryl, $C_{3-10}$cycloalkyl-$C_{1-3}$alkylene, 4-10 membered heterocycloalkyl-$C_{1-3}$alkylene, $C_{6-10}$ aryl-$C_{1-3}$alkylene and 5-10 membered heteroaryl-$C_{1-3}$ alkylene are each optionally substituted with 1, 2, 3, or 4 substituents independently selected from $R^{40}$;

$R^5$ is selected from $C_{1-6}$alkyl, $C_{2-6}$alkenyl, $C_{2-6}$ alkynyl, $C_{1-6}$ haloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$alkylene, $C_{6-10}$ aryl-$C_{1-3}$alkylene, 5-10 membered heteroaryl-$C_{1-3}$alkylene, halo, D, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NOR^{a5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $BR^{h5}R^{i5}$; wherein said $C_{1-6}$alkyl, $C_{2-6}$alkenyl, $C_{2-6}$alkynyl, 4-10 membered heterocycloalkyl, $C_{6-10}$ aryl, 5-10 membered heteroaryl, $C_{3-10}$ cycloalkyl-$C_{1-3}$alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{50}$;

ring A is selected from 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group;

$R^6$ is selected from $C_{1-6}$alkyl, $C_{2-6}$alkenyl, $C_{2-6}$alkynyl, $C_{1-6}$haloalkyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$alkylene, 4-10 membered heterocycloalkyl-$C_{1-3}$alkylene, $C_{6-10}$ aryl-$C_{1-3}$alkylene, 5-10 membered heteroaryl-$C_{1-3}$alkylene, halo, D, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOR^{a6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $BR^{h6}R^{i6}$; wherein said $C_{1-6}$alkyl, $C_{2-6}$alkenyl, $C_{2-6}$alkynyl, $C_{3-10}$cycloalkyl, 4-10 membered heterocycloalkyl, $C_{6-10}$ aryl, 5-10 membered heteroaryl, $C_{3-10}$cycloalkyl-$C_{1-3}$alkylene, 4-10 membered heterocycloalkyl-$C_{1-3}$alkylene, $C_{6-10}$alkylene and 5-10 membered heteroaryl-$C_{1-3}$alkylene are each optionally substituted with 1, 2, 3, or 4 substituents independently selected from $R^{60}$;

n is 0, 1, 2, 3, or 4;

each $R^{10}$ is independently selected from $C_{1-6}$alkyl, $C_{2-6}$alkenyl, $C_{2-6}$alkynyl, $C_{1-6}$haloalkyl, $C_{3-10}$cycloalkyl, 4-10 membered heterocycloalkyl, $C_{6-10}$ aryl, 5-10 membered heteroaryl, $C_{3-10}$ cycloalkyl-$C_{1-3}$alkylene, 4-10 membered heterocycloalkyl-$C_{1-3}$alkylene, $C_{6-10}$ aryl-$C_{1-3}$ alkylene, 5-10 membered heteroaryl-$C_{1-3}$alkylene, halo, D, CN, $NO_2$, $OR^{a10}$, $SR^{a10}$, $C(O)R^{b10}$, $C(O)NR^{c10}R^{d10}$, $C(O)OR^{a10}$, $OC(O)R^{b10}$, $OC(O)NR^{c10}R^{d10}$, $NR^{c10}R^{d10}$, $NR^{c10}C(O)R^{b10}$, $NR^{c10}C(O)OR^{a10}$, $NR^{c10}C(O)NR^{c10}R^{d10}$, $C(=NR^{e10}R^{b10}$, $C(=NOR^{a10})R^{b10}$, $C(=NR^{e10})NR^{c10}R^{d10}$, $NR^{c10}C(=NR^{e10})NR^{c10}R^{d10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, $S(O)_2NR^{c10}R^{d10}$, and $BR^{h10}R^{i10}$; wherein said $C_{1-6}$ alkyl, $C_{2-6}$ alkenyl, $C_{2-6}$ alkynyl, $C_{3-10}$cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene, 5-10 membered heteroaryl-$C_{1-3}$ alkylene, halo, D, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)^2R^{b11}$, $S(O)_2NR^{c11}R^{d11}$, and $BR^{h11}R^{i11}$; wherein said $C_{1-6}$ alkyl, $C_{2-6}$alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, and $BR^{h12}R^{i12}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a20}$, $SR^{a20}$, $C(O)R^{b20}$, $C(O)NR^{c20}R^{d20}$, $C(O)OR^{a20}$, $OC(O)R^{b20}$, $OC(O)NR^{c20}R^{d20}$, $NR^{c20}R^{d20}$, $NR^{c20}C(O)R^{b20}$, $NR^{c20}C(O)OR^{a20}$, $NR^{c20}C(O)NR^{c20}R^{d20}$, $NR^{c20}S(O)R^{b20}$, $NR^{c20}S(O)_2R^{b20}$, $NR^{c20}S(O)_2NR^{c20}R^{d20}$, $S(O)R^{b20}$, $S(O)NR^{c20}R^{d20}$, $S(O)_2R^{b20}$, $S(O)_2NR^{c20}R^{d20}$, and $BR^{h20}R^{i20}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_2$-6 alkenyl, $C_2$-6 alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, and $BR^{h21}R^{i21}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a22}$, $SR^{a22}$, $C(O)R^{b22}$, $C(O)NR^{c22}R^{d22}$, $C(O)OR^{a22}$, $OC(O)R^{b22}$, $OC(O)NR^{c22}R^{d22}$, $NR^{c22}R^{d22}$, $NR^{c22}C(O)R^{b22}$, $NR^{c22}C(O)OR^{a22}$, $NR^{c22}C(O)NR^{c22}R^{d22}$, $NR^{c22}S(O)R^{b22}$, $NR^{c22}S(O)_2R^{b22}$, $NR^{c22}S(O)^2NR^{c22}R^{d22}$, $S(O)R^{b22}$, $S(O)NR^{c22}R^{d22}$, $S(O)_2R^{b22}$, $S(O)_2NR^{c22}R^{d22}$, and $BR^{h22}R^{i22}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a30}$, $SR^{a30}$, $C(O)R^{b30}$, $C(O)NR^{c30}R^{d30}$, $C(O)OR^{a30}$, $OC(O)R^{b30}$, $OC(O)NR^{c30}R^{d30}$, $NR^{c30}R^{d30}$, $NR^{c30}C(O)R^{b30}$, $NR^{c30}C(O)OR^{a30}$, $NR^{c30}C(O)NR^{c30}R^{d30}$, $NR^{c30}S(O)R^{b30}$, $NR^{c30}S(O)_2R^{b30}$, $NR^{c30}(O)_2NR^{c30}R^{d30}$, $S(O)R^{b30}$, $S(O)NR^{c30}R^{d30}$, $S(O)_2R^{b30}$, $S(O)_2NR^{c30}R^{i30}$; and $BR^{h30}R^{i30}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{31}$;

each $R^{31}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene, 5-10 membered heteroaryl-$C_{1-3}$ alkylene, halo, D, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)OR^{a31}$, $NR^{c31}C(O)NR^{c31}R^{d31}$, $NR^{c31}S(O)R^{b31}$, $NR^{c31}S(O)_2R^{b31}$, $NR^{c}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, and $BR^{h31}R^{i31}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{32}$;

each $R^{32}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a32}$, $SR^{a32}$, $C(O)R^{b32}$, $C(O)NR^{c32}R^{d32}$, $C(O)OR^{a32}$, $OC(O)R^{b32}$, $OC(O)NR^{c32}R^{d32}$, $NR^{c32}R^{d32}$, $NR^{c32}C(O)R^{b32}$, $NR^{c32}C(O)OR^{a32}$, $NR^{c32}C(O)NR^{c32}R^{d32}$, $NR^{c32}S(O)R^{b32}$, $NR^{c32}S(O)_2R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, and $BR^{h32}R^{i32}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{40}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a40}$, $SR^{a40}$, $C(O)R^{b40}$, $C(O)NR^{c40}R^{d40}$, $C(O)OR^{a40}$, $OC(O)R^{b40}$, $OC(O)NR^{c40}R^{d40}$, $NR^{c40}R^{d40}$, $NR^{c40}C(O)R^{b40}$, $NR^{c40}C(O)OR^{a40}$, $NR^{c40}C(O)NR^{c40}R^{d40}$, $NR^{c40}S(O)R^{b40}$, $NR^{c40}S(O)_2R^{b40}$, $NR^{c40}S(O)_2NR^{c40}R^{d40}$, $S(O)R^{b40}$, $S(O)NR^{c40}R^{d40}$, $S(O)_2R^{b40}$, $S(O)_2NR^{c40}R^{d40}$, and $BR^{h40}R^{i40}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{41}$;

each $R^{41}$ is independently selected from $C_{1-6}$ alkyl, $C_2$-6 alkenyl, $C_2$-6 alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $NR^{c41}S(O)R^{b41}$, $NR^{c41}S(O)_2R^{b41}$, $NR^{c41}S(O)_2NR^{c41}R^{d41}$, $S(O)R^{b41}$, $S(O)NR^{c41}R^{d41}$, $S(O)_2R^{b41}$, $S(O)_2NR^{c41}R^{d41}$, and $BR^{h41}R^{i41}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{42}$;

each $R^{42}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a42}$, $SR^{a42}$, $C(O)R^{b42}$, $C(O)NR^{c42}R^{d42}$, $C(O)OR^{a42}$, $OC(O)R^{b42}$, $OC(O)NR^{c42}R^{d42}$, $NR^{c42}R^{d42}$, $NR^{c42}C(O)R^{b42}$, $NR^{c42}C(O)OR^{a42}$, $NR^{c42}C(O)NR^{c42}R^{d42}$, $NR^{c42}S(O)R^{b42}$, $NR^{c42}S(O)_2R^{b42}$, $NR^{c42}S(O)_2NR^{c42}R^{d42}$, $S(O)R^{b42}$, $S(O)NR^{c42}R^{d42}$, $S(O)_2R^{b42}$, $S(O)_2NR^{c42}R^{d42}$, and $BR^{h42}R^{i42}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a50}$, $SR^{a50}$, $C(O)R^{b50}$, $C(O)NR^{c50}R^{d50}$, $C(O)OR^{a50}$, $OC(O)R^{b50}$, $OC(O)NR^{c50}R^{d50}$, $NR^{c50}R^{d50}$, $NR^{c50}C(O)R^{b50}$, $NR^{c50}C(O)OR^{a50}$, $NR^{c50}C(O)NR^{c50}R^{d50}$, $NR^{c50}S(O)R^{b50}$, $NR^{c50}S(O)_2R^{b50}$ $S(O)_2NR^{c50}R^{d50}$, $S(O)R^{b50}$, $S(O)NR^{c50}R^{d50}$, $S(O)_2R^{b50}$, $S(O)_2NR^{c50}R^{d50}$, and $BR^{h50}R^{i50}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{51}$;

each $R^{51}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a51}$, $SR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, and $BR^{h51}R^{i51}$; wherein said $C_{1-6}$ alkyl, $C_{2-6}$ alkenyl, $C_{2-6}$ alkynyl, $C_{3-6}$ cycloalkyl, $C_{6-10}$ aryl, 5-6 membered heteroaryl and 4-7 membered heterocycloalkyl, are each optionally substituted with 1, 2, 3, or 4 substituents independently selected from $R^{52}$;

each $R^{52}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a52}$, $SR^{a52}$, $C(O)R^{b52}$, $C(O)NR^{c52}R^{d52}$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)R^{b52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, and $BR^{h62}R^{i52}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{60}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a60}$, $SR^{a60}$, $C(O)R^{b60}$, $C(O)NR^{c60}R^{d60}$, $C(O)OR^{a60}$, $OC(O)R^{b60}$, $OC(O)NR^{c60}R^{d60}$, $NR^{c60}R^{d60}$, $NR^{c60}C(O)R^{b60}$, $NR^{c60}C(O)OR^{a60}$, $NR^{c60}C(O)NR^{c60}R^{d60}$, $NR^{c60}S(O)R^{b60}$, $NR^{c60}S(O)_2R^{b60}$, $NR^{c60}S(O)_2NR^{c60}R^{d60}$, $S(O)R^{b60}$, $S(O)NR^{c60}R^{d60}$, $S(O)_2R^{b60}$, $S(O)_2NR^{c60}R^{d60}$, and $BR^{h60}R^{i60}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^g$;

each $R^{a1}$, $R^{b1}$, $R^{c1}$, and $R^{d1}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

or any $R^{c1}$ and $R^{d1}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{h1}$ and $R^{i1}$ is independently selected from OH, $C_{1-6}$ alkoxy, and $C_{1-6}$ haloalkoxy; or any $R^{h1}$ and $R^{i1}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a2}$, $R^{b2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{20}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3, or 4 substituents independently selected from $R^{20}$;

each $R^{e2}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h2}$ and $R^{i2}$ is independently selected from OH, $C_{1-6}$ alkoxy, and $C_{1-6}$ haloalkoxy; or any $R^{h2}$ and $R^{i2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

or any $R^{c3}$ and $R^{d3}$ attached to the same N atom, together with the N atom to which they are attached, form a 4-, 5-, 6- or 7-membered heterocycloalkyl group optionally substituted with 1, 2, 3, or 4 substituents independently selected from $R^{30}$;

each $R^{e3}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h3}$ and $R^{i3}$ is independently selected from OH, $C_{1-6}$ alkoxy, and $C_{1-6}$ haloalkoxy; or any $R^{h3}$ and $R^{i3}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a4}$, $R^{b4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{e4}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h4}$ and $R^{i4}$ is independently selected from OH, $C_{1-6}$ alkoxy, and $C_{1-6}$ haloalkoxy; or any $R^{h4}$ and $R^{i4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{50}$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^{50}$;

each $R^{e5}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h5}$ and $R^{i5}$ is independently selected from OH, $C_{1-6}$ alkoxy, and $C_{1-6}$ haloalkoxy; or any $R^{h5}$ and $R^{i5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a6}$, $R^{b6}$, $R^{c6}$, and $R^{d6}$ is independently selected from H, $C_{1-6}$ alkyl, $C_{2-6}$ alkenyl, $C_{2-6}$, alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{60}$;

each $R^{e6}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h6}$ and $R^{i6}$ is independently selected from OH, $C_{1-6}$ alkoxy, and $C_{1-6}$ haloalkoxy; or any $R^{h6}$ and $R^{i6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c10}$ and $R^{d10}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{e10}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h10}$ and $R^{i10}$ is independently selected from OH, $C_{1-6}$ alkoxy, and $C_{1-6}$ haloalkoxy; or any $R^{h10}$ and $R^{i10}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a11}$, $R^{b11}$, $R^{c11}$ and $R^{d11}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c11}$ and $R^{d11}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{h11}$ and $R^{i11}$ is independently selected from OH, $C_{1-6}$ alkoxy, and $C_{1-6}$ haloalkoxy; or any $R^{h11}$ and $R^{i11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a12}$, $R^{b12}$, $R^{c12}$ and $R^{d12}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h12}$ and $R^{i12}$ is independently selected from OH, $C_{1-6}$ alkoxy, and $C_{1-6}$ haloalkoxy; or any $R^{h12}$ and $R^{i12}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{21}$;

or any $R^{c20}$ and $R^{d20}$ attached to the same N atom, together with the N atom to which they are attached, form a 4-, 5-, 6- or 7-membered heterocycloalkyl group optionally substituted with 1, 2, 3, or 4 substituents independently selected from $R^{21}$;

each $R^{h20}$ and $R^{i20}$ is independently selected from OH, $C_{1-6}$ alkoxy, and $C_{1-6}$ haloalkoxy; or any $R^{h20}$ and $R^{i20}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a21}$, $R^{b21}$, $R^{c21}$ and $R^{d21}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

or any $R^{c21}$ and $R^{d21}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{h21}$ and $R^{i21}$ is independently selected from OH, $C_{1-6}$ alkoxy, and $C_{1-6}$ haloalkoxy; or any $R^{h21}$ and $R^{i21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a22}$, $R^{b22}$, $R^{c22}$ and $R^{d22}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h22}$ and $R^{i22}$ is independently selected from OH, $C_{1-6}$ alkoxy, and $C_{1-6}$ haloalkoxy; or any $R^{h22}$ and $R^{i22}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a30}$, $R^{b30}$, $R^{c30}$ and $R^{d30}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{31}$;

or any $R^{c30}$ and $R^{d30}$ attached to the same N atom, together with the N atom to which they are attached, form a 4-, 5-, 6- or 7-membered heterocycloalkyl group optionally substituted with 1, 2, 3, or 4 substituents independently selected from $R^{31}$;

each $R^{h30}$ and $R^{i30}$ is independently selected from OH, $C_{1-6}$ alkoxy, and $C_{1-6}$ haloalkoxy; or any $R^{h30}$ and $R^{i30}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a31}$, $R^{b31}$, $R^{c31}$ and $R^{d31}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{32}$;

or any $R^{c31}$ and $R^{d31}$ attached to the same N atom, together with the N atom to which they are attached, form a 4-, 5-, 6- or 7-membered heterocycloalkyl group optionally substituted with 1, 2 or 3 substituents independently selected from $R^{32}$;

each $R^{h31}$ and $R^{i31}$ is independently selected from OH, $C_{1-6}$ alkoxy, and $C_{1-6}$ haloalkoxy; or any $R^{h31}$ and $R^{i31}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a32}$, $R^{b32}$, $R^{c32}$ and $R^{d32}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c32}$ and $R^{d32}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h32}$ and $R^{i32}$ is independently selected from OH, $C_{1-6}$ alkoxy, and $C_{1-6}$ haloalkoxy; or any $R^{h32}$ and $R^{i32}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a40}$, $R^{b40}$, $R^{c40}$ and $R^{d40}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{41}$;

or any $R^{c40}$ and $R^{d40}$ attached to the same N atom, together with the N atom to which they are attached, form a 4-, 5-, 6- or 7-membered heterocycloalkyl group optionally substituted with 1, 2, 3, or 4 substituents independently selected from $R^{41}$;

each $R^{h40}$ and $R^{i40}$ is independently selected from OH, $C_{1-6}$ alkoxy, and $C_{1-6}$ haloalkoxy; or any $R^{h40}$ and $R^{i40}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a41}$, $R^{b41}$, $R^{c41}$ and $R^{d41}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{42}$;

or any $R^{c41}$ and $R^{d41}$ attached to the same N atom, together with the N atom to which they are attached, form a 4-, 5-, 6- or 7-membered heterocycloalkyl group optionally substituted with 1, 2 or 3 substituents independently selected from $R^{42}$;

each $R^{h41}$ and $R^{i41}$ is independently selected from OH, $C_{1-6}$ alkoxy, and $C_{1-6}$ haloalkoxy; or any $R^{h41}$ and $R^{i41}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a42}$, $R^{b42}$, $R^{c42}$ and $R^{d42}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c42}$ and $R^{d42}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h42}$ and $R^{i42}$ is independently selected from OH, $C_{1-6}$ alkoxy, and $C_{1-6}$ haloalkoxy; or any $R^{h42}$ and $R^{i42}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a50}$, $R^{b50}$, $R^{c50}$ and $R^{d50}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{51}$;

or any $R^{c50}$ and $R^{d50}$ attached to the same N atom, together with the N atom to which they are attached, form a 4-, 5-, 6- or 7-membered heterocycloalkyl group optionally substituted with 1, 2 or 3 substituents independently selected from $R^{51}$;

each $R^{h50}$ and $R^{i50}$ is independently selected from OH, $C_{1-6}$ alkoxy, and $C_{1-6}$ haloalkoxy; or any $R^{h50}$ and $R^{i50}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a51}$, $R^{b51}$, $R^{c51}$ and $R^{d51}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{52}$;

or any $R^{c51}$ and $R^{d51}$ attached to the same N atom, together with the N atom to which they are attached, form a 4-, 5-, 6- or 7-membered heterocycloalkyl group optionally substituted with 1, 2, 3, or 4 substituents independently selected from $R^{52}$;

each $R^{h51}$ and $R^{i51}$ is independently selected from OH, $C_{1-6}$ alkoxy, and $C_{1-6}$ haloalkoxy; or any $R^{h51}$ and $R^{i51}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a52}$, $R^{b52}$, $R^{c52}$ and $R^{d52}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c52}$ and $R^{d52}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h52}$ and $R^{i52}$ is independently selected from OH, $C_{1-6}$ alkoxy, and $C_{1-6}$ haloalkoxy; or any $R^{h52}$ and $R^{i52}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a60}$, $R^{b60}$, $R^{c60}$ and $R^{d60}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^g$;

or any $R^{c60}$ and $R^{d60}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h60}$ and $R^{i60}$ is independently selected from OH, $C_{1-6}$ alkoxy, and $C_{1-6}$ haloalkoxy; or any $R^{h60}$ and $R^{i60}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^g$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$alkyl)aminocarbonyloxy, $C_{1-6}$ alkylsulfonylamino, aminosulfonyl, $C_{1-6}$ alkylaminosulfonyl, di($C_{1-6}$alkyl)aminosulfonyl, aminosulfonylamino, $C_{1-6}$ alkylaminosulfonylamino, di($C_{1-6}$alkyl)aminosulfonylamino, aminocarbonylamino, $C_{1-6}$ alkylaminocarbonylamino, and di($C_{1-6}$ alkyl)aminocarbonylamino.

2. The compound of claim 1, or a pharmaceutically acceptable salt thereof, wherein $R^1$ is selected from H, D, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, and $BR^{h1}R^{i1}$;

X is N or $CR^2$;

$R^2$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, and $BR^{h2}R^{i2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{20}$;

Cy is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^3$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NOR^{a3})R^{b3}$, $C(=NR^{e3})NR^{c3}R^{d3}$, $NR^{c3}C(=NR^{e3})NR^{c3}R^{d3}$, $NR^{c3}C(=NR^{e3})R^{b3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)^2R^{b3}$, $S(O)_2NR^{c3}R^{d3}$, and $BR^{h3}R^{i3}$; wherein said $C_{1-6}$ alkyl, $C_{2-6}$ alkenyl, $C_{2-6}$ alkynyl, $C_{3-10}$cycloalkyl, 4-10 membered heterocycloalkyl, $C_{6-10}$ aryl, 5-10 membered heteroaryl, $C_{3-10}$cycloalkyl-$C_{1-3}$alkylene, 4-10 membered heterocycloalkyl-$C_{1-3}$alkylene, $C_{6-10}$ aryl-$C_{1-3}$alkylene and 5-10 membered heteroaryl-$C_{1-3}$ alkylene are each optionally substituted with 1, 2, 3, or 4 substituents independently selected from $R^{30}$;

$R^4$ is selected from $C_{1-6}$ alkyl, $C_{2-6}$ alkenyl, $C_{2-6}$ alkynyl, $C_{1-6}$ haloalkyl, $C_{3-10}$cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$alkylene, 5-10 membered heteroaryl-$C_{1-3}$ alkylene, halo, D, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NOR^{a4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $BR^{h4}R^{i4}$; wherein said $C_{1-6}$ alkyl, $C_{2-6}$ alkenyl, $C_{2-6}$ alkynyl, $C_{3-10}$cycloalkyl, 4-10 membered heterocycloalkyl, $C_{6-10}$ aryl, 5-10 membered heteroaryl, $C_{3-10}$cycloalkyl-$C_{1-3}$alkylene, 4-10 membered heterocycloalkyl-$C_{1-3}$alkylene, $C_{6-10}$ aryl-$C_{1-3}$alkylene and 5-10 membered heteroaryl-$C_{1-3}$ alkylene are each optionally substituted with 1, 2, 3, or 4 substituents independently selected from $R^{40}$;

$R^5$ is selected from $C_{1-6}$ alkyl, $C_{2-6}$ alkenyl, $C_{2-6}$ alkynyl, $C_{1-6}$ haloalkyl, 4-10 membered heterocycloalkyl, $C_{6-10}$ aryl, 5-10 membered heteroaryl, $C_{3-10}$cycloalkyl-$C_{1-3}$alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NOR^{a5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $BR^{h5}R^{i5}$; wherein said $C_{1-6}$ alkyl, $C_{2-6}$ alkenyl, $C_{2-6}$ alkynyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{50}$;

ring A is selected from 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group;

$R^6$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOR^{a6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $BR^{h6}R^{i6}$;

wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{60}$;

n is 0, 1, 2, 3, or 4;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a10}$, $SR^{a10}$, $C(O)R^{b10}$, $C(O)NR^{c10}R^{d10}$, $C(O)OR^{a10}$, $OC(O)R^{b10}$, $OC(O)NR^{c10}R^{d10}$, $NR^{c10}R^{d10}$, $NR^{c10}C(O)R^{b10}$, $NR^{c10}C(O)OR^{a10}$, $NR^{c10}C(O)NR^{c10}R^{d10}$, $C(=NR^{e10})R^{10}$, $C(=NOR^{a10})R^{b10}$, $C(=NR^{e10})NR^{c10}R^{d10}$, $NR^{c10}C(=NR^{e10})NR^{c10}R^{d10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, $S(O)_2NR^{c10}R^{d10}$, and $BR^{h10}R^{i10}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, and $BR^{h11}R^{i11}$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$alkylene, 5-10 membered heteroaryl-$C_{1-3}$ alkylene, halo, D, CN, $NO_2$, $OR^{a20}$, $SR^{a20}$, $C(O)R^{b20}$, $C(O)NR^{c20}R^{d20}$, $C(O)OR^{a20}$, $OC(O)R^{b20}$, $OC(O)NR^{c20}R^{d20}$, $NR^{c20}R^{d20}$, $NR^{c20}C(O)R^{b20}$, $NR^{c20}C(O)OR^{a20}$, $NR^{c20}C(O)NR^{c20}R^{d20}$, $NR^{c20}S(O)R^{b20}$, $NR^{c20}S(O)_2R^{b20}$, $NR^{c20}S(O)_2NR^{c20}R^{d20}$, $S(O)R^{b20}$, $S(O)NR^{c20}R^{d20}$, $S(O)_2R^{b20}$, $S(O)_2NR^{c20}R^{d20}$, and $BR^{h20}R^{i20}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$alkylene, 5-10 membered heteroaryl-$C_{1-3}$ alkylene, halo, D, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$; $S(O)_2R^{b21}$; $S(O)_2NR^{c21}R^{d21}$, and $BR^{h21}R^{i21}$;

each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$alkylene, 5-10 membered heteroaryl-$C_{1-3}$ alkylene, halo, D, CN, $NO_2$, $OR^{a30}$, $SR^{a30}$, $C(O)R^{b30}$, $C(O)NR^{c30}R^{d30}$, $C(O)OR^{a30}$, $OC(O)R^{b30}$, $OC(O)NR^{c30}R^{d30}$, $NR^{c30}R^{d30}$, $NR^{c30}C(O)R^{b30}$, $NR^{c30}C(O)OR^{a30}$, $NR^{c30}C(O)NR^{c30}R^{d30}$, $NR^{c30}S(O)R^{b30}$, $NR^{c30}S(O)_2R^{b30}$, $NR^{c30}S(O)_2NR^{c30}R^{b30}$, $S(O)R^{b30}$, $S(O)NR^{c30}R^{d30}$, $S(O)_2R^{b30}$, $S(O)_2NR^{c30}R^{d30}$, and $BR^{h30}R^{i30}$;

each $R^{40}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$alkylene, 5-10 membered heteroaryl-$C_{1-3}$ alkylene, halo, D, CN, $NO_2$, $OR^{a40}$, $SR^{a40}$, $C(O)R^{b40}$, $C(O)NR^{c40}R^{d40}$, $C(O)OR^{a40}$, $OC(O)R^{b40}$, $OC(O)NR^{c40}R^{d40}$, $NR^{c40}R^{d40}$, $NR^{c40}C(O)R^{b40}$, $NR^{c40}C(O)OR^{a40}$, $NR^{c40}C(O)NR^{c40}R^{d40}$, $NR^{c40}S(O)R^{b40}$, $NR^{c40}S(O)_2R^{b40}$, $NR^{c40}S(O)_2NR^{c40}R^{d40}$, $S(O)R^{b40}$, $S(O)NR^{c40}R^{d40}$, $S(O)_2R^{b40}$, $S(O)_2NR^{c40}R^{d40}$, and $BR^{h40}R^{i40}$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a50}$, $SR^{a50}$, $C(O)R^{b50}$, $C(O)NR^{c50}R^{d50}$, $C(O)OR^{a50}$, $OC(O)R^{b50}$, $OC(O)NR^{c50}R^{d50}$, $NR^{c50}R^{d50}$, $NR^{c50}C(O)R^{b50}$, $NR^{c50}C(O)OR^{a50}$, $NR^{c50}C(O)NR^{c50}R^{d50}$, $NR^{c50}S(O)R^{b50}$, $NR^{c50}S(O)_2R^{b50}$, $NR^{c50}S(O)_2NR^{c50}R^{d50}$, $S(O)R^{b50}$, $S(O)NR^{c50}R^{d50}$, $S(O)_2R^{b50}$, $S(O)_2NR^{c50}R^{d50}$, and $BR^{h50}R^{i50}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{51}$;

each $R^{51}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a51}$, $SR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, and $BR^{h51}R^{i51}$; wherein said $C_{1-6}$ alkyl, $C_{2-6}$ alkenyl, $C_{2-6}$ alkynyl, $C_{3-6}$ cycloalkyl, $C_{6-10}$ aryl, 5-6 membered heteroaryl and 4-7 membered heterocycloalkyl, are each optionally substituted with 1, 2, 3, or 4 substituents independently selected from $R^{52}$;

each $R^{52}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a52}$, $SR^{a52}$, $C(O)R^{b52}$, $C(O)NR^{c52}R^{d52}$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)R^{b52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, and $BR^{h52}R^{i52}$;

each $R^{60}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a60}$, $SR^{a60}$, $C(O)R^{b60}$, $C(O)NR^{c60}R^{d60}$, $C(O)OR^{a60}$, $OC(O)R^{b60}$, $OC(O)NR^{c60}R^{d60}$, $NR^{c60}R^{d60}$, $NR^{c60}C(O)R^{b60}$, $NR^{c60}C(O)OR^{a60}$, $NR^{c60}C(O)NR^{c60}R^{d60}$, $NR^{c60}S(O)R^{b60}$, $NR^{c60}S(O)_2R^{b60}$, $NR^{c60}S(O)_2NR^{c60}R^{d60}$, $S(O)R^{b60}$, $S(O)NR^{c60}R^{d60}$, $S(O)_2R^{b60}$, $S(O)_2NR^{c60}R^{d60}$, and $BR^{h60}R^{i60}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^g$;

each $R^{a1}$, $R^{b1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

or any $R^{c1}$ and $R^{d1}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{h1}$ and $R^{i1}$ is independently selected from OH, $C_{1-6}$ alkoxy, and $C_{1-6}$ haloalkoxy; or any $R^{h1}$ and $R^{i1}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a2}$, $R^{b2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{20}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3, or 4 substituents independently selected from $R^{20}$;

each $R^{e2}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h2}$ and $R^{i2}$ is independently selected from OH, $C_{1-6}$ alkoxy, and $C_{1-6}$ haloalkoxy; or any $R^{h2}$ and $R^{i2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

or any $R^{c3}$ and $R^{d3}$ attached to the same N atom, together with the N atom to which they are attached, form a 4-, 5-, 6- or 7-membered heterocycloalkyl group optionally substituted with 1, 2, 3, or 4 substituents independently selected from $R^{30}$;

each $R^{e3}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h3}$ and $R^{i3}$ is independently selected from OH, $C_{1-6}$ alkoxy, and $C_{1-6}$ haloalkoxy; or any $R^{h3}$ and $R^{i3}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a4}$, $R^{b4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{e4}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h4}$ and $R^{i4}$ is independently selected from OH, $C_{1-6}$ alkoxy, and $C_{1-6}$ haloalkoxy; or any $R^{h4}$ and $R^{i4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{50}$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^{50}$;

each $R^{e5}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h5}$ and $R^{i5}$ is independently selected from OH, $C_{1-6}$ alkoxy, and $C_{1-6}$ haloalkoxy; or any $R^{h5}$ and $R^{i5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a6}$, $R^{c6}$, and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

each $R^{b6}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{60}$;

each $R^{e6}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h6}$ and $R^{i6}$ is independently selected from OH, $C_{1-6}$ alkoxy, and $C_{1-6}$ haloalkoxy; or any $R^{h6}$ and $R^{i6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c10}$ and $R^{d10}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{e10}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h10}$ and $R^{i10}$ is independently selected from OH, $C_{1-6}$ alkoxy, and $C_{1-6}$ haloalkoxy; or any $R^{h10}$ and $R^{i10}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a11}$, $R^{b11}$, $R^{c11}$ and $R^{d11}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c11}$ and $R^{d11}$ attached to the same N atom, together with the N atom to which they are attached, form a 4-, 5-, 6- or 7-membered heterocycloalkyl group;

each $R^{h11}$ and $R^{i11}$ is independently selected from OH, $C_{1-6}$ alkoxy, and $C_{1-6}$ haloalkoxy; or any $R^{h11}$ and $R^{i11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{21}$;

or any $R^{c20}$ and $R^{d20}$ attached to the same N atom, together with the N atom to which they are attached, form a 4-, 5-, 6- or 7-membered heterocycloalkyl group optionally substituted with 1, 2, 3, or 4 substituents independently selected from $R^{21}$;

each $R^{h20}$ and $R^{i20}$ is independently selected from OH, $C_{1-6}$ alkoxy, and $C_{1-6}$ haloalkoxy; or any $R^{h20}$ and $R^{i20}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a21}$, $R^{b21}$, $R^{c21}$ and $R^{d21}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c21}$ and $R^{d21}$ attached to the same N atom, together with the N atom to which they are attached, form a 4-, 5-, 6- or 7-membered heterocycloalkyl group;

each $R^{h21}$ and $R^{i21}$ is independently selected from OH, $C_{1-6}$ alkoxy, and $C_{1-6}$ haloalkoxy; or any $R^{h21}$ and $R^{i21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a30}$, $R^{b30}$, $R^{c30}$ and $R^{d30}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c30}$ and $R^{d30}$ attached to the same N atom, together with the N atom to which they are attached, form a 4-, 5-, 6- or 7-membered heterocycloalkyl group;

each $R^{h30}$ and $R^{i30}$ is independently selected from OH, $C_{1-6}$ alkoxy, and $C_{1-6}$ haloalkoxy; or any $R^{h30}$ and $R^{i30}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a40}$, $R^{b40}$, $R^{c40}$ and $R^{d40}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c40}$ and $R^{d40}$ attached to the same N atom, together with the N atom to which they are attached, form a 4-, 5-, 6- or 7-membered heterocycloalkyl group;

each $R^{h40}$ and $R^{i40}$ is independently selected from OH, $C_{1-6}$ alkoxy, and $C_{1-6}$ haloalkoxy; or any $R^{h40}$ and $R^{i40}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a50}$, $R^{b50}$, $R^{c50}$ and $R^{d50}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{51}$;

or any $R^{c50}$ and $R^{d50}$ attached to the same N atom, together with the N atom to which they are attached, form a 4-, 5-, 6- or 7-membered heterocycloalkyl group optionally substituted with 1, 2 or 3 substituents independently selected from $R^{51}$;

each $R^{h50}$ and $R^{i50}$ is independently selected from OH, $C_{1-6}$ alkoxy, and $C_{1-6}$ haloalkoxy; or any $R^{h50}$ and $R^{i50}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a51}$, $R^{b51}$, $R^{c51}$ and $R^{d51}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{52}$;

or any $R^{c51}$ and $R^{d51}$ attached to the same N atom, together with the N atom to which they are attached, form a 4-, 5-, 6- or 7-membered heterocycloalkyl group optionally substituted with 1, 2, 3, or 4 substituents independently selected from $R^{52}$;

each $R^{h51}$ and $R^{i51}$ is independently selected from OH, $C_{1-6}$ alkoxy, and $C_{1-6}$ haloalkoxy; or any $R^{h51}$ and $R^{i51}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a52}$, $R^{b52}$, $R^{c52}$ and $R^{d52}$, is independently selected from H, $C_{1-6}$ alkyl, $C_{2-6}$ alkenyl, $C_{2-6}$ alkynyl and $C_{1-6}$ haloalkyl;

or any $R^{c52}$ and $R^{d52}$ attached to the same N atom, together with the N atom to which they are attached, form a 4-, 5-, 6- or 7-membered heterocycloalkyl group;

each $R^{h52}$ and $R^{i52}$ is independently selected from OH, $C_{1-6}$ alkoxy, and $C_{1-6}$ haloalkoxy; or any $R^{h52}$ and $R^{i52}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a60}$, $R^{b60}$, $R^{c60}$ and $R^{d60}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^g$;

or any $R^{c60}$ and $R^{d60}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h60}$ and $R^{i60}$ is independently selected from OH, $C_{1-6}$ alkoxy, and $C_{1-6}$ haloalkoxy; or any $R^{h60}$ and $R^{i60}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^g$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

3. The compound of claim 1, or a pharmaceutically acceptable salt thereof, wherein
$R^1$ is selected from H, D, $C_{1-6}$ alkyl, $C_{1-6}$ haloalkyl, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$;

X is N or $CR^2$;

$R^2$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{20}$;

Cy is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^3$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$alkylene, 5-10 membered heteroaryl-$C_{1-3}$alkylene, halo, D, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$;

$R^4$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$alkylene, 5-10 membered heteroaryl-$C_{1-3}$alkylene, halo, D, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$;

$R^5$ is selected from $C_{1-6}$ alkyl, $C_{2-6}$ alkenyl, $C_{2-6}$ alkynyl, $C_{1-6}$ haloalkyl, 4-10 membered heterocycloalkyl, $C_{6-10}$ aryl, 5-10 membered heteroaryl, $C_{3-10}$cycloalkyl- $C_{1-3}$alkylene, 4-10 membered heterocycloalkyl-$C_{1-3}$ alkylene, $C_{6-10}$ aryl-$C_{1-3}$alkylene, 5-10 membered heteroaryl-$C_{1-3}$ alkylene, halo, D, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $NR^{c5}S(O)_2R^{b5}$, $NR^{c5}S(O)_2NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$alkylene and 5-10 membered heteroaryl-$C_{1-3}$ alkylene are each optionally substituted with 1, 2, 3, or 4 substituents independently selected from $R^{50}$;

ring A is selected from 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group;

$R^6$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)_2R^{b6}$, $NR^{c6}S(O)_2NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{60}$;

n is 0, 1, 2, 3, or 4;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene, 5-10 membered heteroaryl-$C_{1-3}$ alkylene, halo, D, CN, $OR^{a10}$, $SR^{a10}$, $C(O)R^{b10}$, $C(O)NR^{c10}R^{d10}$, $C(O)OR^{a10}$, $OC(O)R^{b10}$, $OC(O)NR^{c10}R^{d10}$, $NR^{c10}R^{d10}$, $NR^{c10}C(O)R^{b10}$, $NR^{c10}C(O)OR^{a10}$, $NR^{c10}C(O)NR^{c10}R^{d10}$, $NR^{c10}S(O)_2R^{b10}$, $NR^{c10}S(O)_2NR^{c10}R^{d10}$, $S(O)_2R^{b10}$, and $S(O)_2NR^{c10}R^{d10}$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene, 5-10 membered heteroaryl-$C_{1-3}$ alkylene, halo, D, CN, $OR^{a20}$, $SR^{a20}$, $C(O)R^{b20}$, $C(O)NR^{c20}R^{d20}$, $C(O)OR^{a20}$, $OC(O)R^{b20}$, $OC(O)NR^{c20}R^{d20}$, $NR^{c20}R^{d20}$, $NR^{c20}C(O)R^{b20}$, $NR^{c20}C(O)OR^{a20}$, $NR^{c20}C(O)NR^{c20}R^{d20}$, $NR^{c20}S(O)_2R^{b20}$, $NR^{c20}S(O)_2NR^{c20}R^{d20}$, $S(O)_2R^{b20}$, and $S(O)_2NR^{c20}R^{d20}$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene, 5-10 membered heteroaryl-$C_{1-3}$ alkylene, halo, D, CN, $OR^{a50}$, $SR^{a50}$, $C(O)R^{b50}$, $C(O)NR^{c50}R^{d50}$, $C(O)OR^{a50}$, $OC(O)R^{b50}$, $OC(O)NR^{c50}R^{d50}$, $NR^{c50}R^{d50}$, $NR^{c50}C(O)R^{b50}$, $NR^{c50}C(O)OR^{a50}$, $NR^{c50}C(O)NR^{c50}R^{d50}$, $NR^{c50}S(O)_2R^{b50}$, $NR^{c50}S(O)_2NR^{c50}R^{d50}$, $S(O)_2R^{b50}$, and $S(O)_2NR^{c50}R^{d50}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{51}$;

each $R^{51}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene, 5-10 membered heteroaryl-$C_{1-3}$ alkylene, halo, D, CN, $OR^{a51}$, $SR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)_2R^{b51}$, $NR^{c51}S(O)_2NR^{c51}R^{d51}$, $S(O)_2R^{b51}$, and $S(O)_2NR^{c51}R^{d61}$;

each $R^{60}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a60}$, $SR^{a60}$, $C(O)R^{b60}$, $C(O)NR^{c60}R^{d60}$, $C(O)OR^{a60}$, $OC(O)R^{b60}$, $OC(O)NR^{c60}R^{d60}$, $NR^{c60}R^{d60}$, $NR^{c60}C(O)R^{b60}$, $NR^{c60}C(O)OR^{a60}$, $NR^{c60}C(O)NR^{c60}R^{d60}$, $NR^{c60}S(O)_2R^{b60}$, $NR^{c60}S(O)_2NR^{c60}R^{d60}$, $S(O)_2R^{b60}$, and $S(O)_2NR^{c60}R^{d60}$;

each $R^{a1}$, $R^{b1}$, $R^{c1}$, and $R^{d1}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl;

or any $R^{c1}$ and $R^{d1}$ attached to the same N atom, together with the N atom to which they are attached, form a 4-, 5-, 6- or 7-membered heterocycloalkyl group;

each $R^{a2}$, $R^{b2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{20}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3, or 4 substituents independently selected from $R^{20}$;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c3}$ and $R^{d3}$ attached to the same N atom, together with the N atom to which they are attached, form a 4-, 5-, 6- or 7-membered heterocycloalkyl group;

each $R^{a4}$, $R^{b4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c4}$ and $R^{d4}$ attached to the same N atom, together with the N atom to which they are attached, form a 4-, 5-, 6- or 7-membered heterocycloalkyl group;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{50}$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^{50}$;

each $R^{a6}$, $R^{c6}$, and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

each $R^{b6}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{60}$;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c10}$ and $R^{d10}$ attached to the same N atom, together with the N atom to which they are attached, form a 4-, 5-, 6- or 7-membered heterocycloalkyl group;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c20}$ and $R^{d20}$ attached to the same N atom, together with the N atom to which they are attached, form a 4-, 5-, 6- or 7-membered heterocycloalkyl group;

each $R^{a50}$, $R^{b50}$, $R^{c50}$ and $R^{d50}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{51}$;

or any $R^{c50}$ and $R^{d50}$ attached to the same N atom, together with the N atom to which they are attached, form a 4-, 5-, 6- or 7-membered heterocycloalkyl group optionally substituted with 1, 2 or 3 substituents independently selected from $R^{51}$;

each $R^{a51}$, $R^{b51}$, $R^{c51}$ and $R^{d51}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c51}$ and $R^{d51}$ attached to the same N atom, together with the N atom to which they are attached, form a 4-, 5-, 6- or 7-membered heterocycloalkyl group;

each $R^{a60}$, $R^{b60}$; $R^{c60}$ and $R^{d60}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; and or any $R^{c60}$ and $R^{d60}$ attached to the same N atom, together with the N atom to which they are attached, form a 4-, 5-, 6- or 7-membered heterocycloalkyl group.

4. The compound of claim 1, or a pharmaceutically acceptable salt thereof, wherein $R^1$ is selected from H, D, $C_{1-6}$ alkyl, $C_{1-6}$ haloalkyl, halo, and CN;

X is $CR^2$;

$R^2$ is selected from H, $C_{1-6}$ alkyl, $C_{1-6}$ haloalkyl, $C_{3-10}$ cycloalkyl-$C_{1-3}$alkylene, 4-10 membered heterocycloalkyl-$C_{1-3}$alkylene, halo, D, CN, $OR^{a2}$, $C(O)NR^{c2}R^{d2}$, and $NR^{c2}R^{d2}$; wherein said $C_{1-6}$ alkyl, $C_{3-10}$ cycloalkyl-$C_{1-3}$ alkylene, and 4-10 membered heterocycloalkyl-$C_{1-3}$ alkylene, are each optionally substituted with 1, 2, or 3 substituents independently selected from $R^{20}$;

Cy is selected from $C_{6-10}$ aryl and 5-10 membered heteroaryl; wherein the 5-10 membered heteroaryl each has at least one ring-forming carbon atom and 1, 2, 3, or 4 ring-forming heteroatoms independently selected from N and O; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, or 3 substituents independently selected from $R^{10}$;

$R^3$ is selected from H, $C_{1-6}$ alkyl, $C_{1-6}$ haloalkyl, halo, D, and CN;

$R^4$ is selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a4}$, and $NR^{c4}R^{d4}$;

$R^5$ is selected from $C_{1-6}$ alkyl, $C_{1-6}$ haloalkyl, 4-10 membered heterocycloalkyl, $C_{6-10}$ aryl, 5-10 membered heteroaryl, halo, D, $OR^{a5}$, and $NR^{c5}R^{d5}$; wherein said $C_{1-6}$ alkyl, 4-10 membered heterocycloalkyl, $C_{6-10}$ aryl, and 5-10 membered heteroaryl, are each optionally substituted with 1, 2, or 3 substituents independently selected from $R^{50}$;

ring A is selected from 4-10 membered heterocycloalkyl; wherein the 4-10 membered heterocycloalkyl has at least one ring-forming carbon atom and 1, 2, 3, or 4 ring-forming heteroatoms independently selected from N and O; wherein a ring-forming carbon atom of 4-10 membered heterocycloalkyl is optionally substituted by oxo to form a carbonyl group;

$R^6$ is selected from $C_{1-6}$ alkyl, $C_{1-6}$ haloalkyl, halo, D, CN, $OR^{a6}$, and $NR^{c6}R^{d6}$; wherein said $C_{1-6}$ alkyl is optionally substituted with 1, 2, or 3 substituents independently selected from $R^{60}$;

n is 0, 1, or 2;

each $R^{10}$ is independently selected from $C_{1-6}$ alkyl, $C_{1-6}$ haloalkyl, halo, D, CN, $OR^{a10}$, and $NR^{c10}R^{d10}$;

each $R^{20}$ is independently selected from $C_{1-6}$ alkyl, $C_{1-6}$ haloalkyl, halo, D, CN, $OR^{a20}$, and $NR^{c20}R^{d20}$;

each $R^{50}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a50}$, and $NR^{c50}R^{d50}$; wherein said $C_{1-6}$ alkyl, $C_{3-10}$ cycloalkyl, and 4-10 membered heterocycloalkyl, are each optionally substituted with 1, 2, or 3 substituents independently selected from $R^{51}$;

each $R^{51}$ is independently selected from $C_{1-6}$ alkyl, $C_{1-6}$ haloalkyl, halo, D, CN, $OR^{a51}$, and $NR^{c51}R^{d51}$;

each $R^{60}$ is independently selected from $C_{1-6}$ alkyl, $C_{1-6}$ haloalkyl, halo, D, CN, $OR^{a60}$, and $NR^{c60}R^{d60}$;

each $R^{a2}$, $R^{c2}$ and $R^{d2}$ is independently selected from H, $C_{1-6}$ alkyl, and $C_{1-6}$ haloalkyl; wherein said $C_{1-6}$ alkyl, is optionally substituted with 1, 2, or 3 substituents independently selected from $R^{20}$;

each $R^{a4}$, $R^{b4}$, $R^{c4}$ and $R^{d4}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c4}$ and $R^{d4}$ attached to the same N atom, together with the N atom to which they are attached, form a 4-, 5-, or 6-membered heterocycloalkyl group;

each $R^{a5}$, $R^{c5}$, and $R^{d5}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, or 3 substituents independently selected from $R^{50}$;

or any $R^{c5}$ and $R^{d5}$ attached to the same N atom, together with the N atom to which they are attached, form a 4-, 5-, or 6-membered heterocycloalkyl group optionally substituted with 1, 2 or 3 substituents independently selected from $R^{50}$;

each $R^{a6}$, $R^{c6}$, and $R^{d6}$ is independently selected from H, $C_{1-6}$ alkyl, and $C_{1-6}$ haloalkyl; wherein said $C_{1-6}$ alkyl, is optionally substituted with 1, 2, or 3 substituents independently selected from $R^{60}$;

each $R^{a10}$, $R^{c10}$ and $R^{d10}$ is independently selected from H, $C_{1-6}$ alkyl, and $C_{1-6}$ haloalkyl;

each $R^{a20}$, $R^{c10}$ and $R^{d20}$ is independently selected from H, $C_{1-6}$ alkyl, and $C_{1-6}$ haloalkyl;

each $R^{a50}$, $R^{c50}$ and $R^{d50}$, is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, or 3 substituents independently selected from $R^{51}$;

or any $R^{c50}$ and $R^{d50}$ attached to the same N atom, together with the N atom to which they are attached, form a 4-, 5-, or 6-membered heterocycloalkyl group optionally substituted with 1, 2 or 3 substituents independently selected from $R^{51}$;

each $R^{a51}$, $R^{c51}$ and $R^{d51}$, is independently selected from H, $C_{1-6}$ alkyl, and $C_{1-6}$ haloalkyl; and each $R^{a60}$, $R^{c60}$ and $R^{d60}$ is independently selected from H, $C_{1-6}$ alkyl, and $C_{1-6}$ haloalkyl.

5. The compound of claim 1, or a pharmaceutically acceptable salt thereof, wherein $R^1$ is selected from H, D, $C_{1-6}$ alkyl, $C_{1-6}$ haloalkyl, halo, and CN;

X is N or $CR^2$;

$R^2$ is selected from H, $C_{1-6}$ alkyl, $C_{1-6}$ haloalkyl, $C_{3-10}$ cycloalkyl-$C_{1-3}$ alkylene, 4-10 membered heterocycloalkyl-$C_{1-3}$ alkylene, halo, D, CN, $OR^{a2}$, C(O)$NR^{c2}R^{d2}$, and $NR^{c2}R^{d2}$; wherein said $C_{1-6}$ alkyl, $C_{3-10}$ cycloalkyl-$C_{1-3}$ alkylene, and 4-10 membered heterocycloalkyl-$C_{1-3}$ alkylene, are each optionally substituted with 1, 2, or 3 substituents independently selected from $R^{20}$;

Cy is selected from $C_{6-10}$ aryl and 5-10 membered heteroaryl; wherein the 5-10 membered heteroaryl each has at least one ring-forming carbon atom and 1, 2, 3, or 4 ring-forming heteroatoms independently selected from N and O; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, or 3 substituents independently selected from $R^{10}$;

$R^3$ is selected from H, $C_{1-6}$ alkyl, $C_{1-6}$ haloalkyl, halo, D, and CN;

$R^4$ is selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a4}$, and $NR^{c4}R^{d4}$;

$R^5$ is selected from $C_{1-6}$ alkyl, $C_{1-6}$ haloalkyl, 4-10 membered heterocycloalkyl, $C_{6-10}$ aryl, 5-10 membered heteroaryl, halo, D, $OR^{a5}$, and $NR^{c5}R^{d5}$; wherein said $C_{1-6}$ alkyl, 4-10 membered heterocycloalkyl, $C_{6-10}$ aryl, and 5-10 membered heteroaryl, are each optionally substituted with 1, 2, or 3 substituents independently selected from $R^{50}$;

ring A is selected from 4-10 membered heterocycloalkyl; wherein the 4-10 membered heterocycloalkyl has at least one ring-forming carbon atom and 1, 2, 3, or 4 ring-forming heteroatoms independently selected from N and O; wherein a ring-forming carbon atom of 4-10 membered heterocycloalkyl is optionally substituted by oxo to form a carbonyl group;

$R^6$ is selected from $C_{1-6}$ alkyl, $C_{1-6}$ haloalkyl, halo, D, CN, $OR^{a6}$, and $NR^{c6}R^{d6}$; wherein said $C_{1-6}$ alkyl, is optionally substituted with 1, 2, or 3 substituents independently selected from $R^{60}$;

n is 0, 1, or 2;

each $R^{10}$ is independently selected from $C_{1-6}$ alkyl, $C_{1-6}$ haloalkyl, halo, D, CN, $OR^{a10}$, and $NR^{c10}R^{d10}$;

each $R^{20}$ is independently selected from $C_{1-6}$ alkyl, $C_{1-6}$ haloalkyl, halo, D, CN, $OR^{a20}$, and $NR^{c20}R^{d20}$;

each $R^{50}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a50}$, and $NR^{c50}R^{d50}$; wherein said $C_{1-6}$ alkyl, $C_{3-10}$ cycloalkyl, and 4-10 membered heterocycloalkyl, are each optionally substituted with 1, 2, or 3 substituents independently selected from $R^{51}$;

each $R^{51}$ is independently selected from $C_{1-6}$ alkyl, $C_{1-6}$ haloalkyl, halo, D, CN, $OR^{a51}$, and $NR^{c51}R^{d51}$;

each $R^{60}$ is independently selected from $C_{1-6}$ alkyl, $C_{1-6}$ haloalkyl, halo, D, CN, $OR^{a60}$, and $NR^{c60}R^{d60}$;

each $R^{a2}$, $R^{c2}$ and $R^{d2}$ is independently selected from H, $C_{1-6}$ alkyl, and $C_{1-6}$ haloalkyl; wherein said $C_{1-6}$ alkyl, is optionally substituted with 1, 2, or 3 substituents independently selected from $R^{20}$;

each $R^{a4}$, $R^{b4}$, $R^{c4}$ and $R^{d4}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c4}$ and $R^{d4}$ attached to the same N atom, together with the N atom to which they are attached, form a 4-, 5-, or 6-membered heterocycloalkyl group;

each $R^{a5}$, $R^{c5}$, and $R^{d5}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, or 3 substituents independently selected from $R^{50}$;

or any $R_{c5}$ and $R^{d5}$ attached to the same N atom, together with the N atom to which they are attached, form a 4-, 5-, or 6-membered heterocycloalkyl group optionally substituted with 1, 2 or 3 substituents independently selected from $R^{50}$;

each $R^{a6}$, $R^{c6}$, and $R^{d6}$ is independently selected from H, $C_{1-6}$ alkyl, and $C_{1-6}$ haloalkyl; wherein said $C_{1-6}$ alkyl, is optionally substituted with 1, 2, or 3 substituents independently selected from $R^{60}$;

each $R^{a10}$, $R^{c10}$ and $R^{d10}$ is independently selected from H, $C_{1-6}$ alkyl, and $C_{1-6}$ haloalkyl;

each $R^{a20}$, $R^{c20}$ and $R^{d20}$ is independently selected from H, $C_{1-6}$ alkyl, and $C_{1-6}$ haloalkyl;

each $R^{a50}$, $R^{c50}$ and $R^{d50}$, is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, or 3 substituents independently selected from $R^{51}$;

or any $R^{c50}$ and $R^{d50}$ attached to the same N atom, together with the N atom to which they are attached, form a 4-, 5-, or 6-membered heterocycloalkyl group optionally substituted with 1, 2 or 3 substituents independently selected from $R^{51}$;

each $R^{a51}$, $R^{c51}$ and $R^{d51}$, is independently selected from H, $C_{1-6}$ alkyl, and $C_{1-6}$ haloalkyl; and each $R^{a60}$, $R^{c60}$ and $R^{d60}$ is independently selected from H, $C_{1-6}$ alkyl, and $C_{1-6}$ haloalkyl.

6. The compound of claim 1, wherein the compound of Formula I is a compound of Formula II:

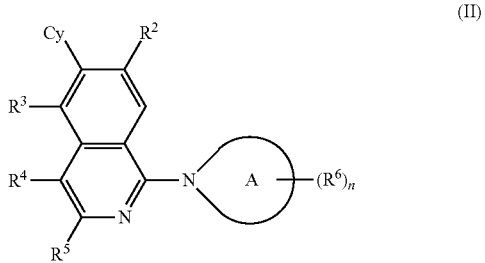

(II)

or a pharmaceutically acceptable salt thereof.

7. The compound of claim 1, wherein $R^1$ is selected from H, $C_{1-6}$ alkyl, $C_{1-6}$ haloalkyl, halo, and CN.

8. The compound of claim 1, wherein X is $CR^2$.

9. The compound of claim 1, wherein X is N.

10. The compound of claim 1, wherein $R^2$ is selected from H, $C_{1-6}$ alkyl, $C_{1-6}$ haloalkyl, halo, D, and CN; wherein said $C_{1-6}$ alkyl is optionally substituted with 1 or 2 substituents independently selected from $R^{20}$.

11. The compound of claim 1, wherein Cy is selected from $C_{6-10}$ aryl and 5-10 membered heteroaryl; wherein the 5-10 membered heteroaryl each has at least one ring-forming carbon atom and 1, 2, 3, or 4 ring-forming heteroatoms independently selected from N and O; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1 or 2 substituents independently selected from $R^{10}$.

12. The compound of claim 1, wherein $R^3$ is selected from H, $C_{1-6}$ alkyl, $C_{1-6}$ haloalkyl, and halo.

13. The compound of claim 1, wherein $R^4$ is selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, and CN.

14. The compound of claim 1, wherein $R^5$ is selected from 4-6 membered heterocycloalkyl, $C_{6-10}$ aryl, and $OR^{a5}$; wherein said 4-6 membered heterocycloalkyl and $C_{6-10}$ aryl, are each optionally substituted with 1 or 2 substituents independently selected from $R^{50}$.

15. The compound of claim 1, wherein ring A is selected from 4-8 membered heterocycloalkyl; wherein the 4-8 membered heterocycloalkyl has at least one ring-forming carbon atom and 1, 2, 3, or 4 ring-forming heteroatoms independently selected from N and O.

16. The compound of claim 1, wherein $R^6$ is selected from $C_{1-6}$ alkyl, $C_{1-6}$ haloalkyl, halo, D, CN, $OR^{a6}$, and $NR^{c6}R^{d6}$; wherein said $C_{1-6}$ alkyl is optionally substituted with 1, 2, or 3 substituents independently selected from $R^{60}$.

17. The compound of claim 1, wherein each $R^{10}$ is independently selected from $C_{1-6}$ alkyl, $C_{1-6}$ haloalkyl, halo, D, CN, $OR^{a10}$, and $NR^{c10}R^{d10}$.

18. The compound of claim 1, wherein each $R^{20}$ is independently selected from $C_{1-6}$ alkyl, $C_{1-6}$ haloalkyl, halo, and CN.

19. The compound of claim 1, wherein each $R^{a5}$ is independently selected from H, $C_{1-6}$ alkyl, $C_{1-6}$ haloalkyl, and 4-10 membered heterocycloalkyl; wherein said $C_{1-6}$ alkyl, and 4-10 membered heterocycloalkyl are each optionally substituted with 1, 2, or 3 substituents independently selected from $R^{50}$.

20. The compound of claim 1, wherein each $R^{50}$ is independently selected from $C_{1-6}$ alkyl, 4-10 membered heterocycloalkyl, and $N(C_{1-6}$ alkyl$)_2$; wherein said $C_{1-6}$ alkyl and 4-10 membered heterocycloalkyl, are each optionally substituted with 1, 2, or 3 substituents independently selected from $C_{1-6}$ alkyl and $N(C_{1-6}$ alkyl$)_2$.

21. The compound of claim 1, wherein each $R^{51}$ is independently selected from $C_{1-6}$ alkyl, $C_{1-6}$ haloalkyl, halo, D, CN, O $R^{a51}$, and $NR^{c51}R^{d51}$.

22. The compound of claim 1, wherein each $R^{60}$ is independently selected from $C_{1-6}$ alkyl, $C_{1-6}$ haloalkyl, halo, D, CN, O $R^{a60}$, and $NR^{c60}R^{d60}$.

23. The compound of claim 1, wherein the compound of Formula I is selected from 1-(3,8-diazabicyclo[3.2.1]octan-8-yl)-3-(3-(dimethylamino)azetidin-1-yl)-5-fluoro-6-(3-hydroxynaphthalen-1-yl)isoquinoline-4-carbonitrile;

3-(1-(3,8-diazabicyclo[3.2.1]octan-8-yl)-4-chloro-3-(3-(dimethylamino)azetidin-1-yl)-5-fluoro-6-(3-hydroxynaphthalen-1-yl)isoquinolin-7-yl)propanenitrile;

3-(1-(3,8-diazabicyclo[3.2.1]octan-8-yl)-3-(3-(dimethyl-amino)azetidin-1-yl)-5-fluoro-6-(3-hydroxynaphtha-len-1-yl)-4-methylisoquinolin-7-yl)propanenitrile;

3-(1-(3,8-diazabicyclo[3.2.1]octan-8-yl)-3-(3-(dimethyl-amino)azetidin-1-yl)-5-fluoro-6-(3-hydroxynaphtha-len-1-yl)-4-phenylisoquinolin-7-yl)propanenitrile;

3-(1-(3,8-diazabicyclo[3.2.1]octan-8-yl)-4-cyclopropyl-3-(3-(dimethylamino)azetidin-1-yl)-5-fluoro-6-(3-hy-droxynaphthalen-1-yl)isoquinolin-7-yl)propanenitrile;

1-(3,8-diazabicyclo[3.2.1]octan-8-yl)-7-(2-cyanoethyl)-3-(3-(dimethylamino)azetidin-1-yl)-5-fluoro-6-(3-hy-droxynaphthalen-1-yl)isoquinoline-4-carbonitrile;

1-(3,8-diazabicyclo[3.2.1]octan-8-yl)-7-(2-cyanoethyl)-5-fluoro-6-(3-hydroxynaphthalen-1-yl)-3-(((S)-1-methylpyrrolidin-2-yl)methoxy)isoquinoline-4-carbo-nitrile;

1-(3,8-diazabicyclo[3.2.1]octan-8-yl)-7-(2-cyanoethyl)-5-fluoro-6-(3-hydroxynaphthalen-1-yl)-3-((1-meth-ylpiperidin-4-yl)oxy)isoquinoline-4-carbonitrile;

1-(3,8-diazabicyclo[3.2.1]octan-8-yl)-7-(2-cyanoethyl)-3-(3-((dimethylamino)methyl)phenyl)-5-fluoro-6-(3-hydroxynaphthalen-1-yl)isoquinoline-4-carbonitrile;

1-((1R,4R)-2,5-diazabicyclo[2.2.2]octan-2-yl)-7-(2-cya-noethyl)-3-(3-(dimethylamino)azetidin-1-yl)-5-fluoro-6-(3-hydroxynaphthalen-1-yl)isoquinoline-4-carboni-trile;

1-((2S,4S)-4-amino-2-(hydroxymethyl)pyrrolidin-1-yl)-7-(2-cyanoethyl)-3-(3-(dimethylamino)azetidin-1-yl)-5-fluoro-6-(3-hydroxynaphthalen-1-yl)isoquinoline-4-carbonitrile;

7-(2-cyanoethyl)-1-(3-(cyanomethyl)pyrrolidin-1-yl)-3-(3-(dimethylamino)azetidin-1-yl)-5-fluoro-6-(3-hy-droxynaphthalen-1-yl)isoquinoline-4-carbonitrile;

1-((S)-3-aminopyrrolidin-1-yl)-7-(2-cyanoethyl)-3-(3-(dimethylamino)azetidin-1-yl)-5-fluoro-6-(3-hy-droxynaphthalen-1-yl)isoquinoline-4-carbonitrile; and 1-((2R,4S)-4-amino-2-methylpyrrolidin-1-yl)-7-(2-cya-noethyl)-3-(3-(dimethylamino)azetidin-1-yl)-5-fluoro-6-(3-hydroxynaphthalen-1-yl)isoquinoline-4-carboni-trile;

or a pharmaceutically acceptable salt thereof.

24. The compound of claim 1, wherein the compound of Formula I is selected from:

1-(3,8-diazabicyclo[3.2.1]octan-3-yl)-5-fluoro-3-(((2R, 7aS)-2-fluorotetrahydro-1H-pyrrolizin-7a(5H)-yl) methoxy)-6-(3-hydroxynaphthalen-1-yl)-2,7-naphthy-ridine-4-carbonitrile; and 1-(3,8-diazabicyclo[3.2.1]octan-3-yl)-3-(3-(dimethyl-amino)-3-methylazetidin-1-yl)-6-(8-ethyl-7-fluoro-3-hydroxynaphthalen-1-yl)-5-fluoro-2,7-naphthyridine-4-carbonitrile;

or a pharmaceutically acceptable salt thereof.

25. The compound of claim 1, wherein the compound of Formula I is 1-((2R,4S)-4-amino-2-methylpyrrolidin-1-yl)-7-(2-cyanoethyl)-3-(3-(dimethylamino)azetidin-1-yl)-5-fluoro-6-(3-hydroxynaphthalen-1-yl)isoquinoline-4-carbo-nitrile, or a pharmaceutically acceptable salt thereof.

26. A pharmaceutical composition comprising the compound of claim 1, or a pharmaceutically acceptable salt thereof, and at least one pharmaceutically acceptable carrier or excipient.

27. A method of inhibiting KRAS activity, said method comprising contacting the compound of claim 1, or a pharmaceutically acceptable salt thereof, with KRAS.

28. The method of claim 27, wherein the contacting comprises administering the compound to a patient.

29. A method of treating a disease or disorder associated with activity of KRAS, said method comprising administering to a patient in need thereof a therapeutically effective amount of the compound of claim 1, or a pharmaceutically acceptable salt thereof.

30. The method of claim 29, wherein the disease or disorder is an immunological or inflammatory disorder.

31. The method of claim 30, wherein the immunological or inflammatory disorder is Ras-associated lymphoprolifera-tive disorder or juvenile myelomonocytic leukemia caused by somatic mutations of KRAS.

32. A method for treating a cancer in a patient, said method comprising administering to the patient a therapeu-tically effective amount of the compound of claim 1, or a pharmaceutically acceptable salt thereof.

33. The method of claim 32, wherein the cancer is selected from carcinomas, hematological cancers, sarcomas, and glioblastoma.

34. The method of claim 33, wherein the cancer is a hematological cancer selected from myeloproliferative neo-plasms, myelodysplastic syndrome, chronic and juvenile myelomonocytic leukemia, acute myeloid leukemia, acute lymphocytic leukemia, and multiple myeloma.

35. The method of claim 33, wherein the cancer is a carcinoma selected from pancreatic carcinoma, colorectal carcinoma, lung carcinoma, bladder carcinoma, gastric car-cinoma, esophageal carcinoma, breast carcinoma, head and neck carcinoma, cervical carcinoma, skin carcinoma, and thyroid carcinoma.

36. A method of treating a disease or disorder associated with activity of a KRAS protein harboring a G12D mutation, said method comprising administering to a patient in need thereof a therapeutically effective amount of the compound of claim 1, or a pharmaceutically acceptable salt thereof.

* * * * *